United States Patent
Zhang et al.

(10) Patent No.: US 7,750,017 B2
(45) Date of Patent: Jul. 6, 2010

(54) HETEROCYCLES

(75) Inventors: Chengzhi Zhang, Orange, CT (US); Roger Smith, Madison, CT (US); Jason Duquette, San Mateo, CA (US); Qian Zhao, Wallingford, CT (US); Jacques Dumas, Bethany, CT (US); Georgiy Bondar, West Haven, CT (US); Yingfu Li, Hamden, CT (US); Dongping Fan, North Haven, CT (US)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 277 days.

(21) Appl. No.: 11/665,313

(22) PCT Filed: Oct. 14, 2005

(86) PCT No.: PCT/US2005/036791

§ 371 (c)(1),
(2), (4) Date: Apr. 13, 2007

(87) PCT Pub. No.: WO2006/044524

PCT Pub. Date: Apr. 27, 2006

(65) Prior Publication Data

US 2008/0132497 A1 Jun. 5, 2008

Related U.S. Application Data

(60) Provisional application No. 60/619,066, filed on Oct. 15, 2004.

(51) Int. Cl.
*A61K 31/505* (2006.01)
*C07D 491/00* (2006.01)
*C07D 471/00* (2006.01)
*C07D 487/00* (2006.01)

(52) U.S. Cl. .................................... 514/267; 544/250
(58) Field of Classification Search ................ 514/267; 544/250

See application file for complete search history.

(56) References Cited

U.S. PATENT DOCUMENTS 5,679,683 A 10/1997 Bridges et al. ............. 514/267
2003/0229051 A1* 12/2003 Bridges et al. ............. 514/80

FOREIGN PATENT DOCUMENTS

WO 9713760 4/1997

OTHER PUBLICATIONS

BF El-Rayes, et al., Targeting the Epidermal Growth Factor Receptor, British J. of Cancer, 91, 418-424 (2004).*
Showalter, et al., "Tyrosine Kinase Inhibitors. 16.6,5,6-Tricyclic Benzothieno [3,2-d]pyrimidines and Pyrimido[5,4-b]- and—[4,5-b]indoles as Potent Inhibitors of the Epidermal Growth Factor Receptor Tyrosine Kinase", J. Med. Chem., 42: 5464-5474 (1999).

* cited by examiner

*Primary Examiner*—James O Wilson
*Assistant Examiner*—Erich A Leeser
(74) *Attorney, Agent, or Firm*—Edwards Angell Palmer & Dodge LLP; Nicholas J. DiCeglie, Jr.; Barry Kramer

(57) ABSTRACT

This invention relates to novel compounds and processes for their preparation, methods of treating diseases, particularly hyperproliferative diseases such as cancer, comprising administering said compounds, and methods of making pharmaceutical compositions for the treatment or prevention of disorders, particularly hyperproliferative diseases such as cancer.

10 Claims, No Drawings

HETEROCYCLES

This application claims benefit of U.S. Provisional Application Ser. No. 60/619,066; filed on Oct. 15, 2004, the content of which is incorporated herein by reference in its entirety.

This invention relates to novel compounds and processes for their preparation, methods of treating diseases, particularly hyperproliferative diseases such as cancer, comprising administering said compounds, and methods of making pharmaceutical compositions for the treatment or prevention of disorders, particularly hyperproliferative diseases such as cancer.

Epidermal growth factor receptors (EGFRs) comprise a family consisting of four known tyrosine kinase receptors, HER1 (EGFR, ErbB1), HER2 (neu, ErbB2), HER3 (ErbB3) and HER4 (ErbB4). These receptors are activated by a number of ligands including EGF, TGFα, epiregulin, amphiregulin and heregulins (neuregulins). The HER family receptors generate cell signaling cascades that transduce extracellular stimulation into intracellular events that control various cellular functions including proliferation, differentiation and apoptosis. These receptors are elevated in a large number of solid tumors and this increase has been associated with the disruption of normal cellular control resulting in more aggressive tumors and a poor disease prognosis. Inhibitors of epidermal growth factor receptors have resulted in stabilization or regression of tumor growth in a broad range of tumor types (Holbro, T., Civenni, G., and Hynes, N. Exp Cell Res. 284: 99-110, 2003). It is believed that the compounds in this invention provide their anti-proliferative effect through the inhibition of the tyrosine kinase activities of epidermal growth factor receptors (in particular ErbB1 and ErbB2).

U.S. Pat. No. 5,679,683 (Pfizer) and WO 97/13760 (Glaxo Wellcome) describe tricyclic compounds capable of inhibiting tyrosine kinases of the epidermal growth factor receptor family.

U.S. Pat. No. 6,482,948 (Nippon Soda), U.S. Pat. No. 6,130,223, U.S. Pat. No. 6,495,557, WO 00/78767, WO 01/019369, WO 01/021620, US 2003/153585, US 2003/022906, US 2004/058940, US 2004/077664 and WO 02/072100 (Merck GmbH) disclose tricyclic compounds as PDE inhibitors.

WO 03/057149 (Bayer) describes heteropyrimidines and hetero-4-pyrimidones for the treatment of $PDE7_B$-mediated diseases.

The present invention relates to a compound of formula

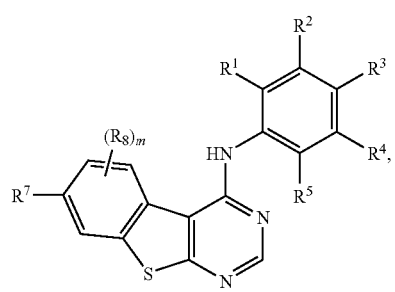

(I)

wherein m is 0, 1 or 2;

$R^1$ is selected from the group consisting of hydrogen, alkyl, and halo;

$R^2$ is selected from the group consisting of hydrogen, alkyl, and halo; and $R^3$ is *—$O(CH_2)_n$Ar, wherein Ar is phenyl, thienyl, furyl, pyrrolyl, thiazolyl, oxazolyl, imidazolyl, pyridyl, pyrimidyl or pyridazinyl, wherein Ar can optionally be substituted with 0, 1 or 2 substituents independently selected from the group consisting of halo, cyano, amino, methyl, ethyl, propyl, hydroxy, methoxy, ethoxy, propoxy, trifluoromethyl and trifluoromethoxy, and wherein n is 0 or 1, or $R^2$ and $R^3$, together with the carbon atoms to which they are attached, form a pyrrole or pyrazole ring, wherein said pyrrole or pyrazole ring can optionally be substituted with 0, 1 or 2 substituents independently selected from the group consisting of alkyl, benzyl, halogenated benzyl, pyridylmethyl, pyridylmethoxy, and halogenated pyridylmethoxy;

$R^4$ is selected from the group consisting of hydrogen, methyl, ethyl, and halo;

$R^5$ is selected from the group consisting of hydrogen, methyl, and halo;

$R^7$ is selected from the group consisting of halo, hydroxy, alkyl, and alkenyl; or $R^7$ is alkoxy, wherein said alkoxy can optionally be substituted with 0, 1 or 2 substituents independently selected from the group consisting of hydroxy, alkoxy, alkoxycarbonyl, amino, alkylamino, morpholinyl, piperidinyl, pyrrolidinyl, piperazinyl, and alkylpiperazinyl, or $R^7$ is alkylamino, wherein said alkylamino can optionally be substituted with 0, 1 or 2 substituents independently selected from the group consisting of hydroxy, alkoxy, hydroxyalkylamino, alkoxyalkylamino, and morpholinyl, piperidinyl, pyrrolidinyl, piperazinyl, and alkylpiperazinyl, or $R^7$ is alkyl selected from the group consisting of methyl, ethyl, n-propyl, i-propyl, n-butyl, i-butyl and t-butyl, wherein said alkyl is substituted with 1, 2, 3 or 4 independently selected substituents $R^{7-1}$, wherein $R^{7-1}$ is selected from the group consisting of halo, oxo, hydroxy, alkoxy, amino, hydroxycarbonyl, and alkoxycarbonyl, or $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or $R^{7-1}$ is alkoxy, wherein said alkoxy can optionally be substituted with 0, 1 or 2 substituents independently selected from the group consisting of hydroxy, alkoxy, amino, alkoxycarbonyl, morpholinyl, pyrrolyl, and pyrrolidinyl, or $R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, oxo, hydroxy, alkoxy, amino, alkylamino, hydroxyalkyl, alkoxyalkyl, carboxyl, and alkoxycarbonyl, or $R^{7-1}$ is a group *—$C(O)NR^{7-2}R^{7-3}$, wherein $R^{7-2}$ is morpholinyl, azabicyclo[2.2.2]oct-3-yl or alkyl, wherein alkyl can optionally be substituted with 0, 1 or 2 substituents selected from the group consisting of hydroxy, alkoxy, hydroxyalkyloxy, alkylamino, methylsulfonyl, piperidinyl and morpholinyl, and wherein $R^{7-3}$ is hydrogen or alkyl, or $R^{7-1}$ is a group *—C(O)NR$^{7-2}$R$^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0, 1 or 2 substituents independently selected from the group consisting of alkyl, hydroxyalkyl, alkoxyalkyl, and alkylamino, or $R^7$ is alkenyl selected from the group consisting of ethenyl, propenyl, or n-butenyl, wherein said alkenyl is substituted with 1, 2 or 3 independently selected substituents $R^{7-4}$, wherein $R^{7-4}$ is selected from the group consisting of halo, hydroxy, oxo, hydroxycarbonyl, alkoxycarbonyl, and alkylamino, wherein alkylamino can be substituted with alkoxy, methylsulfonyl, or alkylamino, or $R^{7-4}$ is a heterocycle selected from the group consisting of pyrrolidinyl, piperazinyl, and morpholinyl, wherein said heterocycle can optionally be substituted with 0, 1 or 2 substituents independently selected from the group consisting of hydroxy, alkoxy, alkyl and alkylamino, or $R^7$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of methyl, ethyl, propyl, halo, oxo, hydroxy, methoxy, ethoxy, propoxy, hydroxyalkyl, alkoxyalkyl, amino and alkylamino;

$R^8$ is selected from the group consisting of halo, cyano, amino, methyl, ethyl, propyl, hydroxy, methoxy, ethoxy, propoxy, trifluoromethyl and trifluoromethoxy;

with the proviso that at least one of $R^1$, $R^2$, $R^4$, and $R^5$ must be other than hydrogen;

or a pharmaceutically acceptable salt thereof.

The compounds according to the invention can also be present in the form of their salts, solvates or solvates of the salts.

Depending on their structure, the compounds according to the invention can exist in stereoisomeric forms (enantiomers or diastereomers). The invention therefore relates to the enantiomers or diastereomers and to their respective mixtures. Such mixtures of enantiomers or diastereomers can be separated into stereoisomerically unitary constituents in a known manner.

The invention also relates to tautomers of the compounds, depending on the structure of the compounds.

DEFINITIONS

Unless otherwise stated, the following definitions apply for the technical expressions used throughout this specification and claims.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of claim 1" is meant to include the simultaneous treatment of more than one disease as well as the administration of more than one compound of claim 1.

A * symbol next to a bond denotes the point of attachment in the molecule.

In general, the nomenclature follows a substitutive pattern, i.e. in more complex substituents, that part which is substituted at the point of connection, appears last. For example, if the expression is used "a molecule is substituted with hydroxyethylamino", then said molecule is substituted with an amino group, which in turn is substituted with an ethyl group, which in turn is substituted with an hydroxy group (HO—CH$_2$CH$_2$—NH-molecule).

Unless otherwise stated, multiple different substituents are allowed on the same or different atoms of the moiety which is substituted, as long as such substitution pattern is chemically meaningful. For example, when the expression is used "R is ethyl, wherein said ethyl is substituted with 1, 2, 3 or 4 independently selected substituents $R^x$, wherein Rx is selected from the group consisting of fluoro, oxo, and hydroxy", then both ethyl carbon atoms can be substituted with any such combination of fluoro, oxo, and hydroxy, including for example, *—CH$_2$CF$_3$, *—C(O)CH$_3$, *—CHFCH$_2$OH, and *—CH$_2$C(O)OH.

Unless otherwise marked as mutually exclusive, in a listing of alternatives from which a selection can be made, the term "or" is does not mutually exclude such alternatives, but rather is used to structure the listing. For example, when the expression is used:

"R is ethyl, wherein said ethyl is substituted with 2 independently selected substituents $R^x$, wherein $R^x$ is selected from the group consisting of fluoro and chloro, or $R^x$ is amino, wherein said amino can optionally be substituted with 0 or 1 substituents independently selected from the group consisting of methyl and ethyl, or $R^x$ is a heterocycle selected from the group consisting of pyrrolidinyl, imidazolyl, morpholinyl, and piperidinyl, wherein said heterocycle can optionally be substituted with 0 or 1 substituents independently selected from the group consisting of methyl and ethyl", then the 2 substituents $R^x$, which have to be present on R, can be any combination of fluoro, chloro, optionally substituted amine, and optionally substituted heterocycle. In other words, the conjunction "or" does not exclude selection from these alternatives, but is only meant to facilitate comprehension.

Salts for the purposes of the invention are preferably pharmacologically acceptable salts of the compounds according to the invention. For example, see S. M. Berge, et al. "Pharmaceutical Salts," *J. Pharm. Sci.* 1977, 66, 1-19.

Pharmacologically acceptable salts of the compounds (I) include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Pharmacologically acceptable salts of the compounds (I) also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention are those forms of the compounds that coordinate with solvent molecules to form a complex in the solid or liquid state. Hydrates are a specific form of solvates, where the solvent is water.

Halo represents fluorine, chlorine, bromine or iodine.

Alkyl represents a linear or branched alkyl radical having generally 1 to 6, or, in another embodiment, 1 to 4, or in yet another embodiment 1 to 3 carbon atoms, illustratively representing methyl, ethyl, n-propyl, isopropyl, tert-butyl, n-pentyl and n-hexyl.

Alkenyl represents a linear or branched alkyl radical having one or more double bonds and 2 to 6, or, in another embodiment, 2 to 4, or in yet another embodiment 2 or 3 carbon atoms, illustratively representing ethylene or allyl.

Alkoxy represents a straight-chain or branched hydrocarbon radical having 1 to 6, or, in another embodiment, 1 to 4, or in yet another embodiment 1 to 3 carbon atoms and bound via an oxygen atom, illustratively representing methoxy, ethoxy, propoxy, isopropoxy, butoxy, isobutoxy, pentoxy, isopentoxy, hexoxy, isohexoxy. The terms "alkoxy" and "alkyloxy" are often used synonymously.

Hydroxyalkyloxy represents an alkoxy group, wherein the alkyl moiety is substituted with an hydroxy group, such as $HO-CH_2CH_2O-*$.

Alkylamino represents an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Hydroxyalkylamino, alkoxyalkylamino and methylsulfonylalkylamino represent an alkylamino radical having an hydroxy, alkoxy or methylsulfonyl substituent respectively.

Alkoxycarbonyl represents a carbonyl radical being substituted with an alkoxy radical, illustratively representing methoxycarbonyl, ethoxycarbonyl, n-propoxycarbonyl, isopropoxycarbonyl, tert-butoxycarbonyl, n-pentoxycarbonyl and n-hexoxycarbonyl.

Aryl represents a mono- to tricyclic carbocyclic radical, which is aromatic at least in one ring and bound via an oxygen atom, having generally 6 to 14 carbon atoms, illustratively representing phenyl, naphthyl and phenanthrenyl.

Heteroaryl represents an monocyclic radical having 5 or 6 ring atoms and up to 5 or up to 4 hetero atoms selected from the group consisting of nitrogen, oxygen and sulfur. It can be attached via a ring carbon atom or a ring nitrogen atom. Illustrative examples are thienyl, furyl, pyrrolyl, thiazolyl, oxazolyl, imidazolyl, pyridyl, pyrimidyl, pyridazinyl, indolyl, and indazolyl.

Halogenated pyridylmethoxy represents a pyridylmethoxy group (*—OCH$_2$-pyr), which is halogenated on the pyridyl ring.

Alkylsulfonyl represents *—S(O)$_2$-alkyl.

In another embodiment, the present invention relates to a compound of formula (I), wherein m is 0;

$R^1$ is hydrogen;

$R^2$ is hydrogen;

$R^3$ is selected from the group consisting of benzyloxy, halogenated benzyloxy, methylated benzyloxy, pyridylmethoxy and thiazolylmethoxy; or $R^2$ and $R^3$, together with the carbon atoms to which they are attached, form a pyrazole ring, wherein said pyrazole ring can optionally be substituted with 0 or 1 substituents independently selected from the group consisting of benzyl and halogenated benzyl;

$R^4$ is fluoro, chloro or bromo;

$R^5$ is hydrogen;

$R^7$ is methoxy, ethoxy or propoxy, wherein said methoxy, ethoxy or propoxy can optionally be substituted with 0, 1 or 2 substituents independently selected from the group consisting of hydroxy, methoxy, ethoxy, propoxy, methoxycarbonyl, ethoxycarbonyl, amino, methylamino, dimethylamino ethylamino, methylethylamino, diethylamino, morpholinyl, piperidinyl, pyrrolidinyl, piperazinyl, and methylpiperazinyl, or $R^7$ is alkyl selected from the group consisting of methyl, ethyl, n-propyl, and n-butyl, wherein said alkyl is substituted with 1 or 2 substituents $R^{7-1}$, wherein $R^{7-1}$ is selected from the group consisting of fluoro, chloro, bromo, hydroxy, methoxy, methoxycarbonyl, and ethoxycarbonyl, or $R^{7-1}$ is ethylamino, methylethylamino, dimethylamino or diethylamino, wherein said ethylamino, methylethylamino, dimethylamino or diethylamino can optionally be substituted with 0, 1 or 2 substituents independently selected from the group consisting of hydroxy, methoxy, ethoxy, methylsulfonyl, and morpholinyl, or $R^{7-1}$ is a heterocycle selected from the group consisting of pyrrolidinyl, imidazolyl, morpholinyl, piperidinyl, piperazinyl, and thiomorpholinyl, wherein said heterocycle can optionally be substituted with 0, 1 or 2 substituents independently selected from the group consisting of methyl, oxo, hydroxy, amino, methylamino, ethylamino, methylethylamino, dimethylamino, diethylamino, hydroxymethyl, hydroxyethyl, methoxymethyl, methoxyethyl, and ethoxyethyl, or $R^{7-1}$ is a group *—C(O)NR$^{7-2}$R$^{7-3}$, wherein $R^{7-2}$ is morpholinyl, methyl, ethyl or propyl, wherein methyl, ethyl or propyl can optionally be substituted with 0, 1 or 2 substituents selected from the group consisting of hydroxy, alkoxy, hydroxyalkyloxy, alkylamino, methylsulfonyl, piperidinyl and morpholinyl, and wherein $R^{7-3}$ is hydrogen, methyl, ethyl or propyl, or $R^{7-1}$ is a group *—C(O)NR$^{7-2}$R$^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0, 1 or 2 substituents independently selected from the group consisting of methyl, ethyl, propyl, methoxymethyl, methoxyethyl, ethoxyethyl, methylamino, ethylamino, methylethylamino, dimethylamino, and diethylamino, or $R^7$ is alkenyl selected from the group consisting of ethenyl, propenyl, or n-butenyl, wherein said alkenyl is substituted with 1, 2 or 3 independently selected substituents $R^{7-4}$, wherein $R^{7-4}$ is selected from the group consisting of halo, hydroxy, oxo, hydroxycarbonyl, methoxycarbonyl, ethoxycarbonyl, methylamino, ethylamino, methylethylamino, dimethylamino, and diethylamino, wherein ethylamino, methylethylamino, and diethylamino can be substituted with methoxy, ethoxy, methylsulfonyl, methylamino, ethylamino, methylethylamino, dimethylamino, or diethylamino, or $R^{7-4}$ is a heterocycle selected from the group consisting of pyrrolidinyl, piperazinyl, and morpholinyl, wherein said heterocycle can optionally be substituted with 0, 1 or 2 substituents independently selected from the group consisting of hydroxy, alkoxy, alkyl and alkylamino;

or a pharmaceutically acceptable salt thereof.

In yet another embodiment, the present invention relates to a compound of formula (I), wherein m is 0;

$R^1$ is hydrogen;

$R^2$ is hydrogen;

$R^3$ is selected from the group consisting of benzyloxy, 3-fluorobenzyloxy, 3-chlorobenzyloxy, 3-bromobenzyloxy, and 3-methylbenzyloxy;

$R^4$ is chloro;

$R^5$ is hydrogen;

$R^7$ is propoxy, wherein said propoxy can optionally be substituted with 0, 1 or 2 substituents independently selected from the group consisting of hydroxy, methoxy, ethoxy, amino, dimethylamino, or diethylamino or $R^7$ is alkyl selected from the group consisting of methyl and ethyl, wherein said alkyl is substituted with 1 or 2 substituents $R^{7-1}$, wherein $R^{7-1}$ is selected from the group consisting of hydroxy, and methoxycarbonyl, or $R^{7-1}$ is ethylamino, methylethylamino, dimethylamino or diethylamino, wherein said ethylamino, methylethylamino or diethylamino can optionally be substituted with 1 or 2 substituents independently selected from the group consisting of hydroxy, methoxy, ethoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, hydroxymethyl, methoxymethyl, and methoxyethyl, or $R^{7-1}$ is a group *—C(O)NR$^{7-2}$R$^{7-3}$, wherein $R^{7-2}$ is morpholinyl or ethyl, wherein ethyl can optionally be substituted with 0 or 1 substituents selected from the group consisting of hydroxy, methoxy, ethoxy, hydroxymethyloxy, hydroxyethyloxy, dimethylamino, methylsulfonyl, piperidinyl and morpholinyl, and wherein $R^{7-3}$ is hydrogen or methyl, or $R^{7-1}$ is a group *—C(O)NR$^{7-2}$R$^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0 or 1 substituents independently selected from the group consisting of methyl, ethyl, propyl, methoxymethyl, methoxyethyl, ethoxyethyl, methylamino, and dimethylamino, or $R^7$ is propenyl, wherein said propenyl is substituted with 1 or 2 independently selected substituents $R^{7-4}$, wherein $R^{7-4}$ is selected from the group consisting of fluoro, chloro, oxo, hydroxycarbonyl, methoxycarbonyl, methylamino, and ethylamino, wherein ethylamino can be substituted with methylsulfonyl, dimethylamino, or diethylamino;

or a pharmaceutically acceptable salt thereof.

In yet another embodiment, the present invention relates to a compound of formula (I), wherein m is 0;

$R^1$ is hydrogen;

$R^2$ is hydrogen;

$R^3$ is 3-fluorobenzyloxy;

$R^4$ is chloro;

$R^5$ is hydrogen;

$R^7$ is propoxy, wherein said propoxy can optionally be substituted with 0, 1 or 2 hydroxy, or $R^7$ is alkyl selected from the group consisting of methyl and ethyl, wherein said alkyl is substituted with 1 or 2 substituents $R^{7-1}$, wherein $R^{7-1}$ is selected from the group consisting of fluoro, chloro, bromo, hydroxy, and methoxycarbonyl, or $R^{7-1}$ is ethylamino, methylethylamino, dimethylamino or diethylamino, wherein said ethylamino, methylethylamino, dimethylamino or diethylamino can optionally be substituted with 1 or 2 substituents independently selected from the group consisting of hydroxy, methoxy, ethoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, hydroxymethyl, methoxymethyl, and methoxyethyl, or $R^{7-1}$ is a group *—C(O)NR$^{7-2}$R$^{7-3}$, wherein $R^{7-2}$ is morpholinyl or ethyl, wherein ethyl can optionally be substituted with 0 or 1 substituents selected from the group consisting of hydroxy, methoxy, ethoxy, hydroxymethyloxy, hydroxyethyloxy, dimethylamino, methylsulfonyl, piperidinyl and morpholinyl, and wherein $R^{7-3}$ is hydrogen or methyl, or $R^{7-1}$ is a group *—C(O)NR$^{7-2}$R$^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0 or 1 substituents independently selected from the group consisting of methyl, ethyl, propyl, methoxymethyl, methoxyethyl, ethoxyethyl, methylamino, and dimethylamino, or $R^7$ is propenyl, wherein said propenyl is substituted with 1 or 2 independently selected substituents $R^{7-4}$, wherein $R^{7-4}$ is selected from the group consisting of fluoro, chloro, oxo, hydroxycarbonyl, methoxycarbonyl, methylamino, and ethylamino, wherein ethylamino can be substituted with methylsulfonyl, dimethylamino, or diethylamino;

or a pharmaceutically acceptable salt thereof.

In yet another embodiment, the present invention relates to a compound of formula (I), wherein m is 0;

$R^1$ is hydrogen;

$R^2$ is hydrogen;

$R^3$ is 3-fluorobenzyloxy;

$R^4$ is chloro;

$R^5$ is hydrogen;

$R^7$ is propoxy, wherein said propoxy can optionally be substituted with 1 or 2 hydroxy, or $R^7$ is ethyl, wherein said ethyl is substituted with 1 or 2 substituents $R^{7-1}$, wherein $R^{7-1}$ is hydroxy, or $R^{7-1}$ is ethylamino or diethylamino, wherein said ethylamino or diethylamino can optionally be substituted with 1 or 2 substituents independently selected from the group consisting of hydroxy, methoxy, and ethoxy, or $R^{7-1}$ is a heterocycle selected from the group consisting of N-pyrrolidinyl, N-morpholinyl, N-piperidinyl, and N-piperazinyl, wherein said heterocycle can optionally be substituted with 0, 1 or 2 substituents independently selected from the group consisting of methyl, oxo, hydroxy, amino, dimethylamino, hydroxymethyl, and methoxymethyl, or $R^{7-1}$ is a group *—C(O)NR$^{7-2}$R$^{7-3}$, wherein $R^{7-2}$ is morpholinyl or ethyl, wherein ethyl can optionally be substituted with 0 or 1 substituents selected from the group consisting of hydroxy, methoxy, ethoxy, hydroxymethyloxy, hydroxyethyloxy, and dimethylamino, and wherein $R^{7-3}$ is hydrogen or methyl, or a pharmaceutically acceptable salt thereof.

In yet another embodiment, the present invention relates to a compound of formula (I-1),

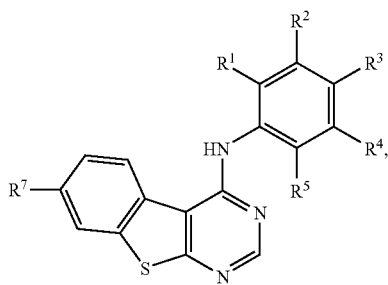

(I-1)

wherein $R^1$ is selected from the group consisting of hydrogen, methyl, and halo;

$R^2$ is selected from the group consisting of hydrogen, methyl, and halo;

$R^3$ is selected from the group consisting of benzyloxy, halogenated benzyloxy, alkylated benzyloxy, pyridoxy, alkylated pyridoxy, halogenated pyridoxy, pyridylmethoxy, and halogenated pyridylmethoxy, or $R^2$ and $R^3$, together with the carbon atoms to which they are attached, form an pyrazole ring, wherein said pyrazole ring can optionally be substituted with 0, 1 or 2 substituents independently selected from the group consisting of alkyl, benzyl, halogenated benzyl, pyridylmethoxy, and halogenated pyridylmethoxy;

$R^4$ is selected from the group consisting of hydrogen, methyl, ethyl, and halo;

$R^5$ is selected from the group consisting of hydrogen, methyl, and halo;

$R^7$ is selected from the group consisting of alkyl or alkenyl, or $R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$, wherein $R^{7-1}$ is selected from the group consisting of halo, hydroxy, alkoxy, alkoxycarbonyl, and amino, or $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or $R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, oxo, hydroxy, alkoxy, amino, alkylamino, hydroxyalkyl, alkoxyalkyl, carboxyl, and alkoxycarbonyl;

with the proviso that at least one of $R^1$, $R^2$, $R^4$, and $R^5$ must be other than hydrogen; or a salt, solvate or solvate of a salt thereof.

In yet another embodiment, the present invention relates to a compound of formula (I), wherein $R^1$ is hydrogen;

$R^2$ is hydrogen;

$R^3$ is selected from the group consisting of benzyloxy, halogenated benzyloxy, and methylated benzyloxy;

$R^4$ is fluoro, chloro or bromo;

$R^5$ is hydrogen;

$R^7$ is vinyl or allyl, or $R^7$ is alkyl selected from the group consisting of methyl, ethyl, n-propyl, and n-butyl, wherein said alkyl is substituted with 1 substituent $R^{7-1}$, wherein $R^{7-1}$ is selected from the group consisting of fluoro, chloro, bromo, hydroxy, methoxy, methoxycarbonyl, and ethoxycarbonyl, or $R^{7-1}$ is ethylamino, methylethylamino, dimethylamino or diethylamino, wherein said ethylamino, methylethylamino, dimethylamino or diethylamino can optionally be substituted with 0, 1 or 2 substituents independently selected from the group consisting of hydroxy, methoxy, ethoxy, methylsulfonyl, and morpholinyl, or $R^{7-1}$ is a heterocycle selected from the group consisting of pyrrolidinyl, imidazolyl, morpholinyl, piperidinyl, piperazinyl, and thiomorpholinyl, wherein said heterocycle can optionally be substituted with 0, 1 or 2 substituents independently selected from the group consisting of methyl, oxo, hydroxy, amino, methylamino, ethylamino, methylethylamino, dimethylamino, diethylamino, methoxymethyl, methoxyethyl, and ethoxyethyl;

or a salt, solvate or solvate of a salt thereof.

In yet another embodiment, the present invention relates to a compound of formula (I), wherein $R^1$ is hydrogen;

$R^2$ is hydrogen;

$R^3$ is selected from the group consisting of benzyloxy, 3-fluorobenzyloxy, 3-chlorobenzyloxy, 3-bromobenzyloxy, and 3-methylbenzyloxy;

$R^4$ is chloro;

$R^5$ is hydrogen;

$R^7$ is vinyl, or $R^7$ is alkyl selected from the group consisting of methyl and ethyl, wherein said alkyl is substituted with 1 substituent $R^{7-1}$, wherein $R^{7-1}$ is selected from the group consisting of fluoro, chloro, bromo, hydroxy, and methoxycarbonyl, or $R^{7-1}$ is ethylamino, methylethylamino or diethylamino, wherein said ethylamino, methylethylamino or diethylamino can optionally be substituted with 1 or 2 substituents independently selected from the group consisting of hydroxy, methoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, methoxymethyl, and methoxyethyl;

or a salt, solvate or solvate of a salt thereof.

In yet another embodiment, the present invention relates to a compound of formula (II),

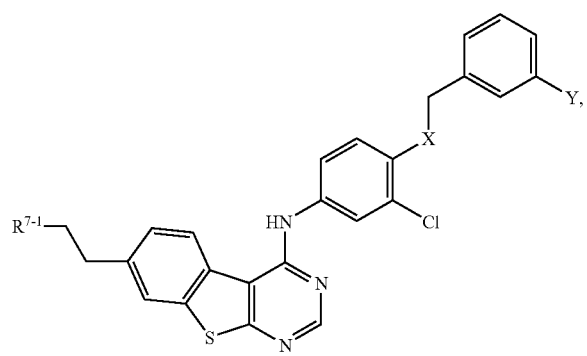

(II)

wherein

X is selected from the groups consisting of nitrogen, oxygen and sulfur;

Y is selected from the group consisting of fluoro, chloro, bromo, cyano, methyl and methoxy;

$R^{7-1}$ is selected from the group consisting of fluoro, chloro, bromo, hydroxy, and methoxycarbonyl, or $R^{7-1}$ is ethylamino, methylethylamino or diethylamino, wherein said ethylamino, methylethylamino or diethylamino can optionally be substituted with 1 or 2 substituents independently selected from the group consisting of hydroxy, methoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, methoxymethyl, and methoxyethyl;

or a salt, solvate or solvate of a salt thereof.

In yet another embodiment, the present invention relates to a compound of formula (II), wherein X is oxygen;

Y is fluoro;

$R^{7-1}$ is selected from the group consisting of fluoro, chloro, bromo, hydroxy, and methoxycarbonyl, or $R^{7-1}$ is ethylamino, methylethylamino or diethylamino, wherein said ethylamino, methylethylamino or diethylamino can optionally be substituted with 1 or 2 substituents independently selected from the group consisting of hydroxy, methoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, methoxymethyl, and methoxyethyl;

or a salt, solvate or solvate of a salt thereof.

In another embodiment, the present invention relates to a compound capable of being metabolized or hydrolized to a compound of formula (I) under physiological conditions. Such conditions include known drug biotransformation reactions such as oxidation, hydroxylation and conjugation as described in Goodman and Gilman's *The Pharmacological Basis of Therapeutics*, Section 1, Eighth Edition 1990, Pergamon Press.

In another embodiment, the present invention provides a process for preparing a compound of formula (I), wherein a compound of formula (III)

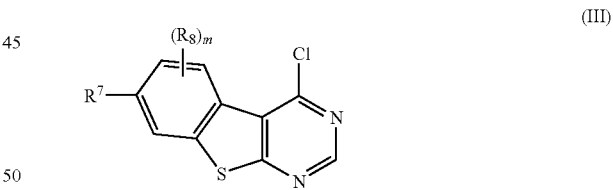

(III)

wherein $R^7$, $R^8$ and m have the meaning indicated above, is reacted with a compound of formula (7)

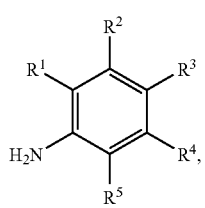

(7)

wherein $R^1$ to $R^5$ have the meaning indicated above.

In another embodiment, the present invention provides a process for preparing the compounds of formula (I), wherein a compound of formula (9)

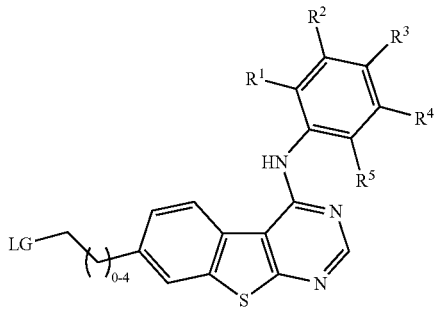

(9)

wherein $R^1$ to $R^5$ have the meaning indicated above and LG represents a leaving group such as bromine or mesylate, is reacted with a nucleophilic compound of formula: $R^{7-1}$, wherein ":" represents a free electron pair, such as imidazole, to yield a compound of formula

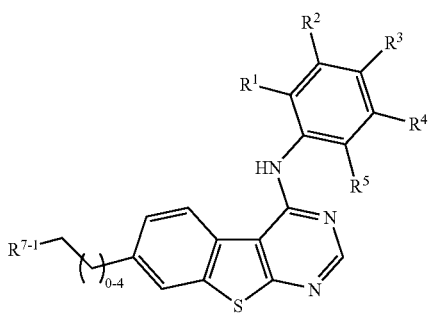

(9)

wherein $R^1$ to $R^5$ and $R^{7-1}$ have the meaning indicated above.

In another embodiment, the present invention provides a process for preparing the compounds of formula (I), wherein a compound of formula (20)

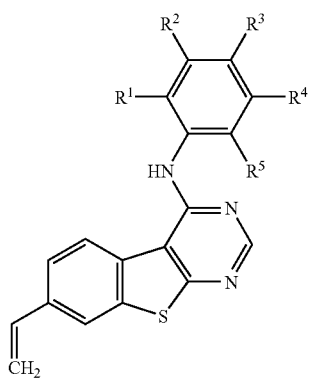

(20)

wherein $R^1$ to $R^5$ have the meaning indicated above, are reacted with an oxidizing agent such as osmium tetroxide to yield compounds of formula (21)

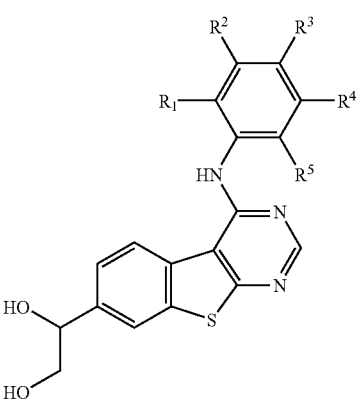

(21)

wherein $R^1$ to $R^5$ have the meaning indicated above.

In yet another embodiment, the present invention provides a process for preparing a compound of formula (I), wherein $R^7$ is alkoxy, comprising reacting a compound of formula (40)

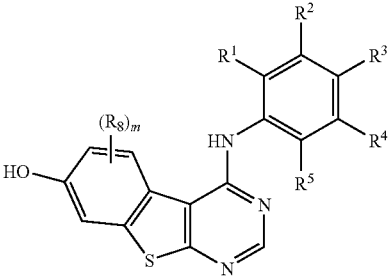

(40)

wherein m and $R^1$ to $R^8$ have the meaning indicated above, with an electrophile such as a substituted alkyl halide, sulfonate or epoxide.

Next to their pharmaceutical properties, compounds of formula (40) are important and valuable precursors for the synthesis of alkoxy type compounds of formula (I). For this reason, in yet another embodiment, the present invention a compound of formula (40), i.e. a compound of formula (I), wherein $R^7$ is hydroxy.

The compounds of formula (III), (7), (9), and (20) are known or can be prepared similarly to known processes or as described herein.

If not mentioned otherwise, the reactions are usually carried out in inert organic solvents which do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-dichloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

The preparation of the compounds according to the invention can be illustrated by means of the following synthetic schemes. In these schemes, unless specifically designated otherwise, $R^1$-$R^7$ are as defined for formula (I) above, R' and R" are a lower alkyl or substituted lower alkyl, LG is a leaving group such as halide or sulfonate.

For reasons of simplicity substituent $R^8$ is not depicted in the schemes below. If a substituent $R^8$ is desired, it can be introduced at various stages of the synthesis described below, for example as a very last step by halogenation, hydroxylation, and oxidation, or early in synthesis, for example by choosing appropriate starting materials (1).

Also for reasons of simplicity substituent $R^{7'}$ is used in schemes 4-7 to depict fragments of $R^7$. Such a fragment is meant to represent the respective definition of $R^7$ without any parts of $R^7$ which are already depicted in the scheme. For example, —$OR^{7'}$ as a whole is meant to represent an alkoxy-type substitutent $R^7$, wherein $R^{7'}$ is identical to $R^7$ except it does not contain the bridging oxygen.

Reaction Schemes 1-7 depict the synthesis of the compounds of Formula (I).

Reaction Scheme 1

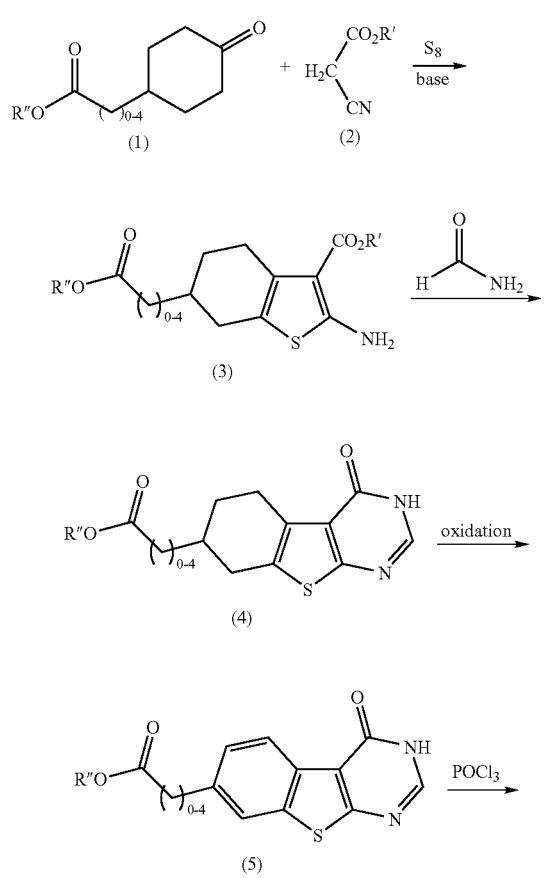

-continued

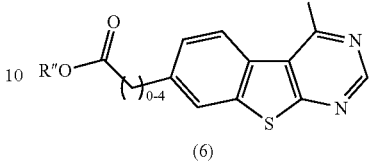

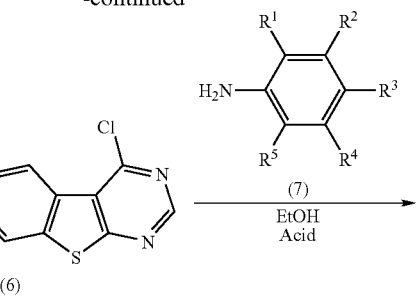

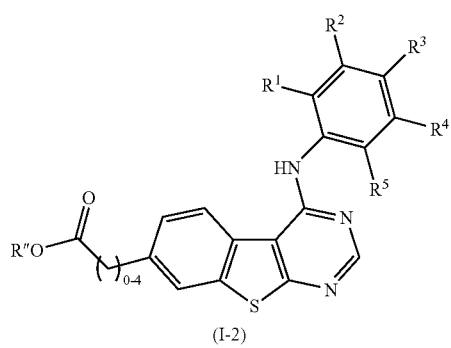

(R' and R" = lower alkyl)

The cyclohexanone (1) of Reaction Scheme 1, where R" is a lower alkyl, is commercially available or may can be synthesized by means well known in the art. Cyclohexanone (1) is coupled with an appropriate cyanoacetic ester (2) in the presence of elemental sulfur and a base such as morpholine, preferably at room temperature, to yield the aminothiophene ester of formula (3) according to the procedure of Gewald, *J. Heterocyclic Chem.*, 1999, 36, 333-345, which is incorporated herein by reference. The aminothiophene ester (3) is then converted to a compound of formula (4) by reaction with a formamide-containing reagent such as neat formamide, or formamidine acetate, in a polar solvent such as DMF, with heat, preferably to 100° C. or above. Oxidation of compound of formula (4) with reagent such as DDQ to yield compound of formula (5). Heating the compound of formula (5) with a reagent such as phosphorous oxychloride provides compound (6). Finally, compound (6) may be reacted with a variety of substituted anilines (7), each of which is readily available or can be synthesized by means well known in the art, in the presence of a catalytic amount of concentrated acid, such as HCl, and a protic solvents, such as ethanol, isopropyl alcohol to yield a compound of Formula (I-2) wherein the $R^7$ is as specified above.

Compound of formula (I) in scheme 1 can be further elaborated as described in Scheme 2. The ester functional group is reduced by hydride source such as DIBAL-H in aprotic solvents such as THF or diethyl ether to afford the alcohol of formula (8). Conversion of the hydroxyl group to leaving groups such as bromide or mesylate by means well known in the art to give compound of formula (9) which then reacts with amines to yield the compound of formula (I-1).

Reaction Scheme 2
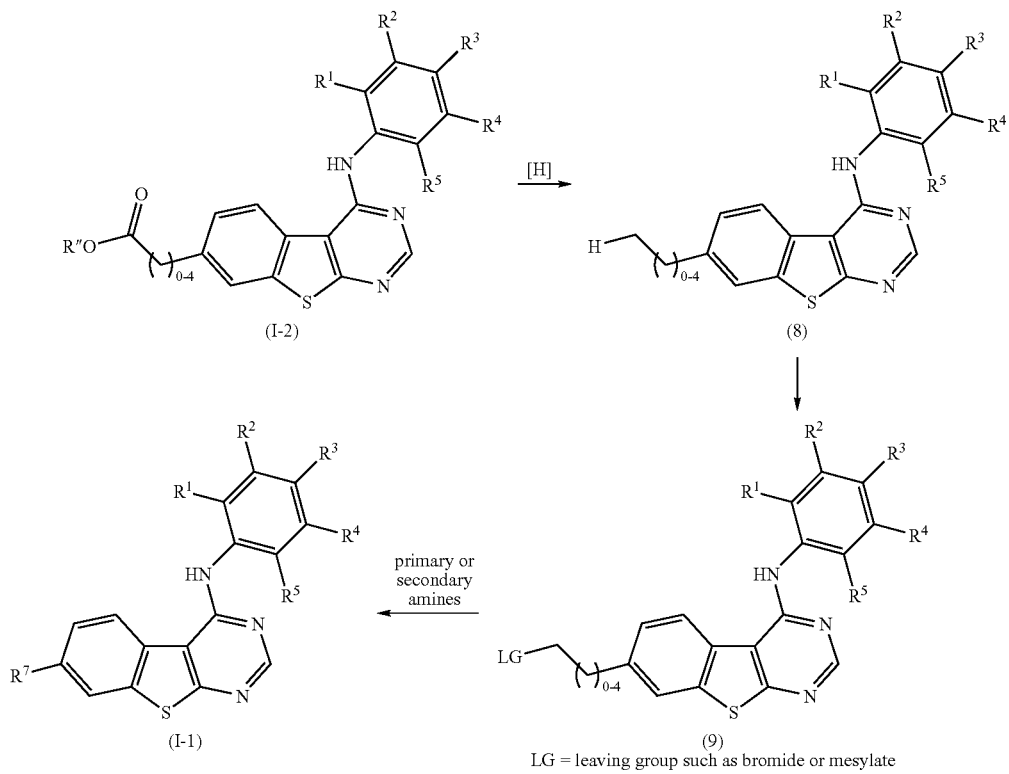
Reaction Scheme 3
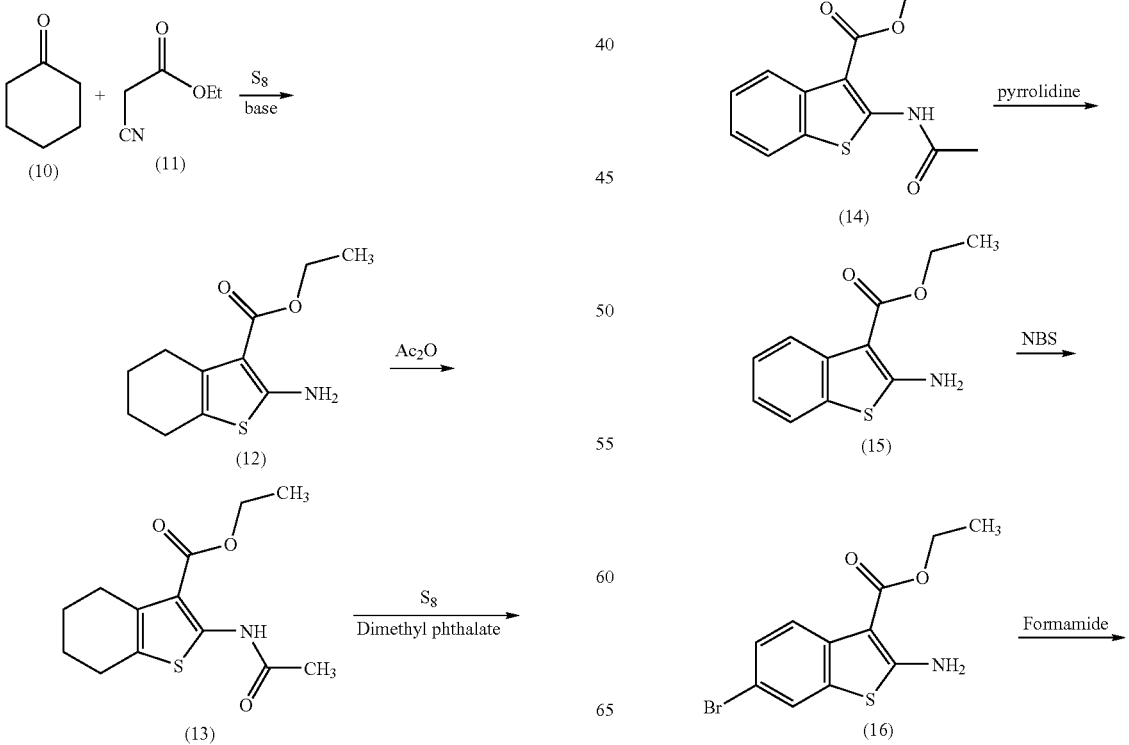

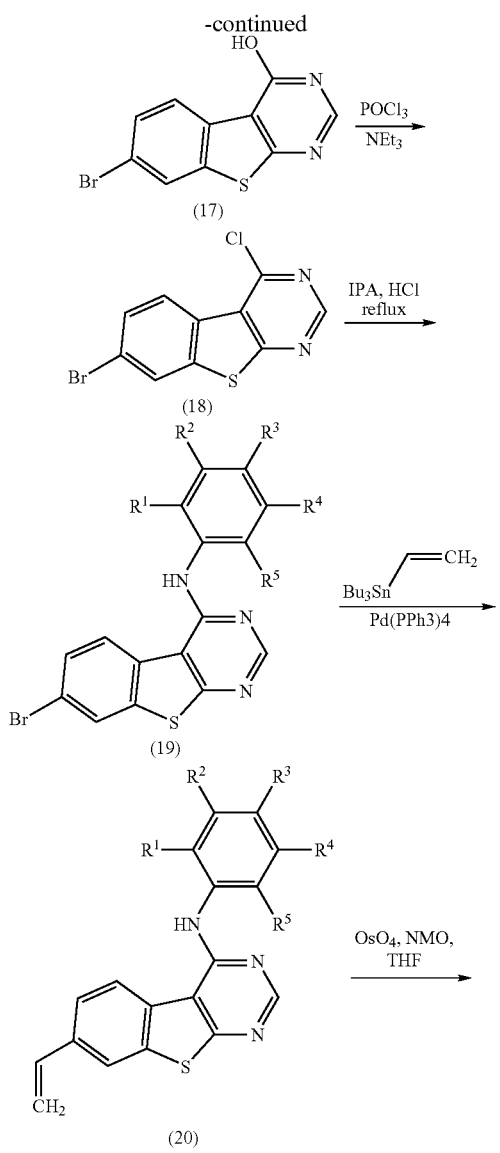

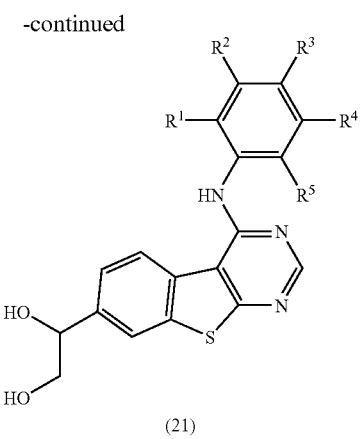

Another synthetic route to prepare compounds in this invention is outlined in Reaction Scheme 3. Followed a similar procedure of preparing 2-aminothiophene as described in Scheme 1, compound of formula (12) is obtained. Acylation followed by oxidation and de-acetylation gave compound (15) which is converted to compound (16) by bromination using NBS. Compound (16) is converted to compound (19) following the similar sequence described in Scheme 1. Palladium catalysed Stille reaction of compound (19) with tributyl vinyl tin to give compound (20) which is then converted to compound (21) by dihydroxylation using $OsO_4$/NMO.

Another synthetic route to prepare compounds in this invention is outlined in Reaction Scheme 4. Compound (19) is allowed to react with an acrylate under Palladium catalyzed Heck reaction conditions to give the versatile acrylate intermediate of formula (22). The acrylate (22) can be directly converted to acrylamide (23) under Lewis acid (such as $AlMe_3$) catalysis. Hydrogenation of compound of formula (23) affords the corresponding compound (26). Alternatively, compound of formula (26) can be synthesized from compound (22) via the reaction sequence of saponification, hydrogenation, and a standard amide formation reaction. The acrylate (22) can also be converted to an allylic alcohol of formula (27) which is then converted to a tri-hydroxyl compound (28) by dihydroxylation using $OsO_4$/NMO.

Reaction Scheme 4

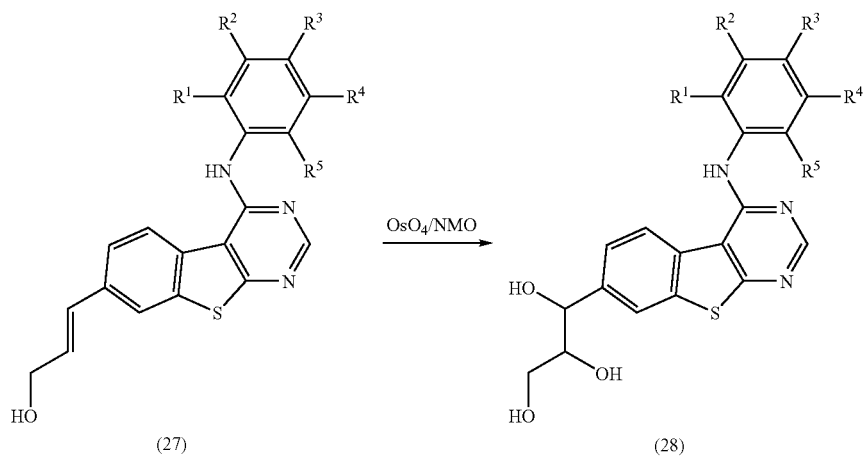

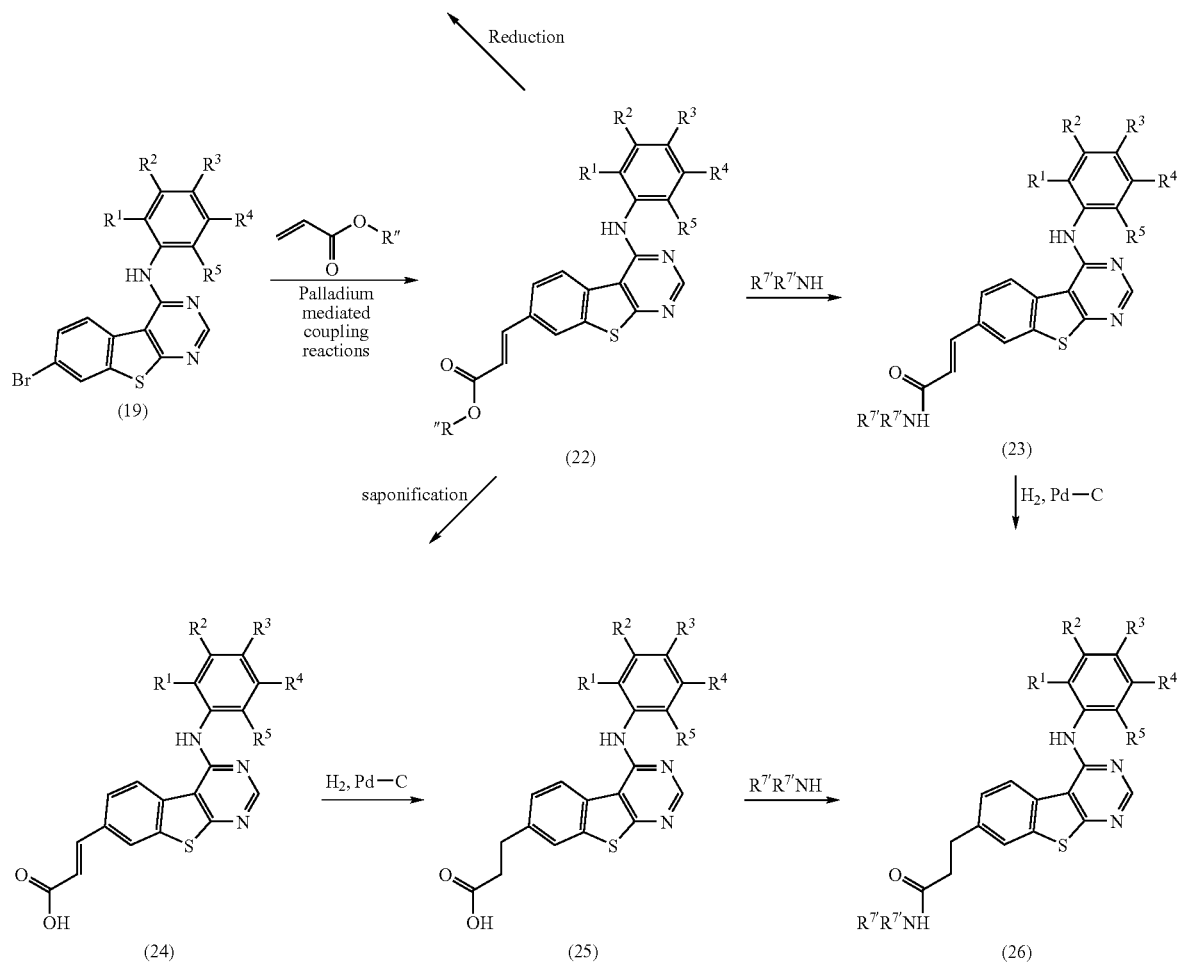
Reaction Scheme 5
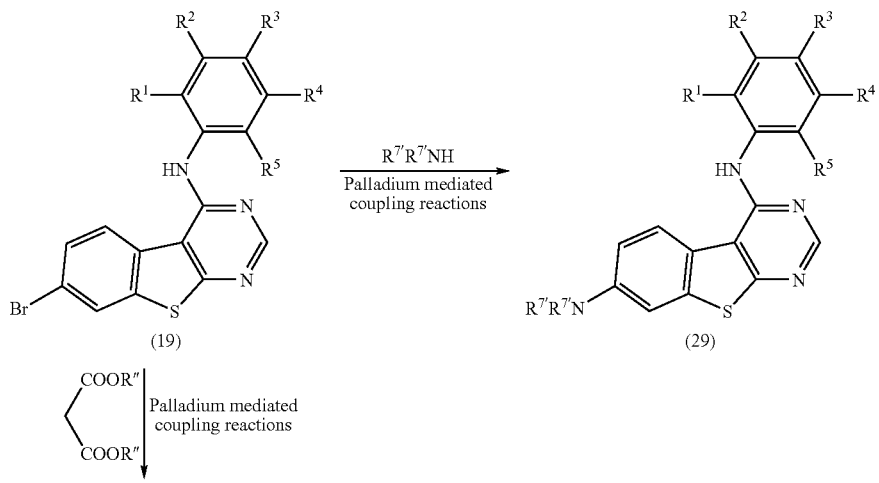

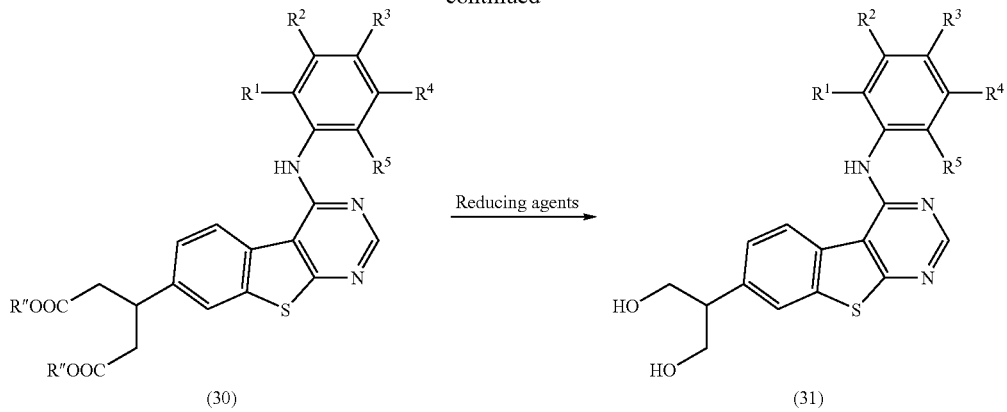

The synthetic route to prepare compounds such as of formulae (29), (30), and (31) in this invention is outlined in Reaction Scheme 5. The versatile compound (19) is allowed to react with an amine under Palladium catalyzed Buchwald reaction conditions to give compound of formula (29). The palladium mediated coupling of compound (19) with malonate gives compound (30) which is converted to compound of formula (31) upon treatment with a hydride source.

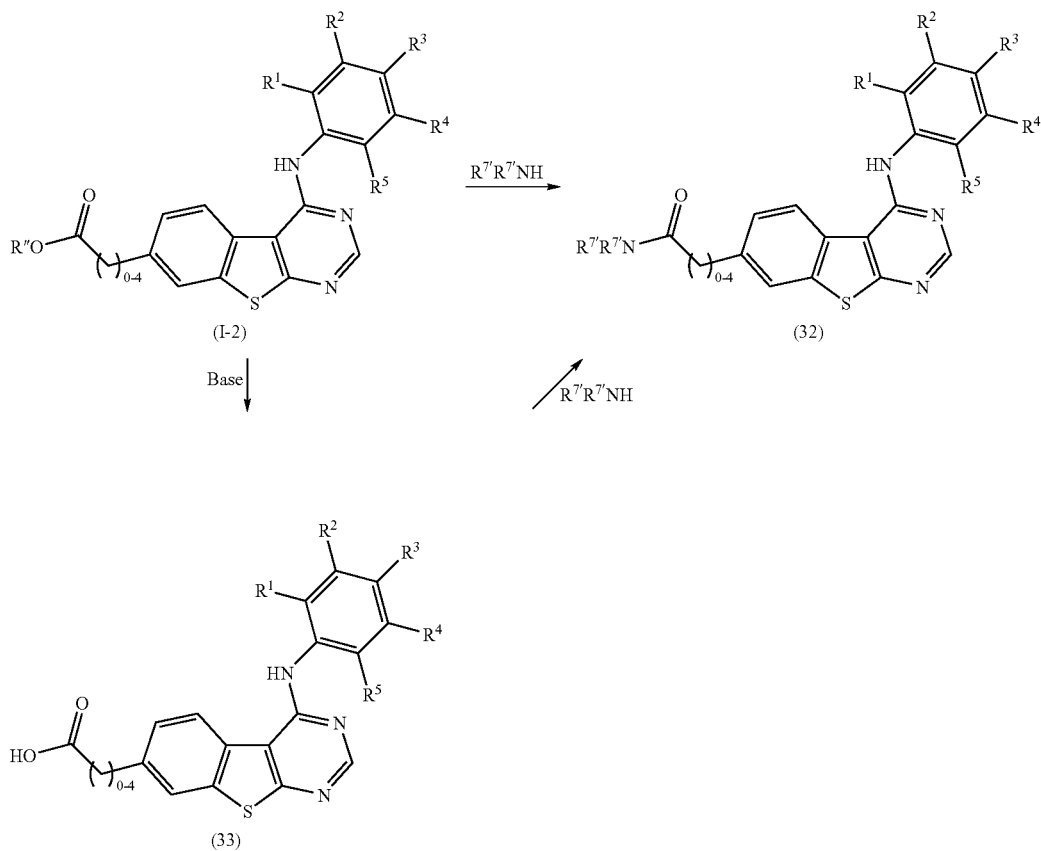

Scheme 6 is outlined the synthetic route for compounds of formula (32) and (33) in this invention. The ester of formula (I-2) in scheme 6 can be directly converted to amide (32) under Lewis acid (such as AlMe₃) catalysis. Alternatively, compound of formula (32) can be synthesized from compound (I-2) via the reaction sequence of saponification, and a standard amide formation reaction.

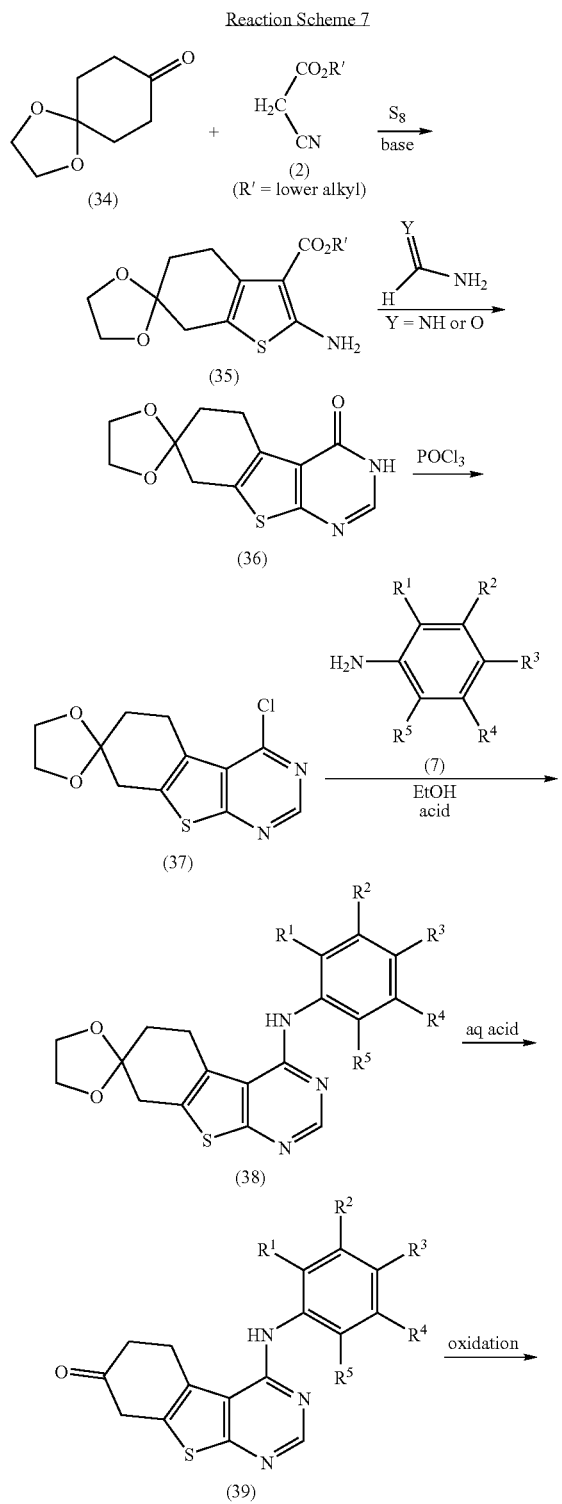

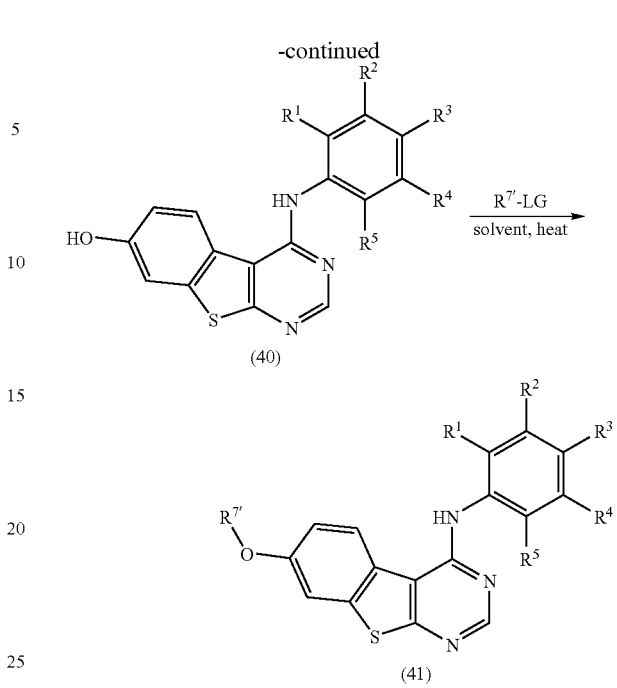

Lastly, compounds of formulae (40) and (41) in the invention can be prepared from the route outlined in Reaction Scheme 7. In this scheme, a mono-protected cyclohexane-1-4-dione of formula (34) is allowed to react with a cyanoacetic acid ester of formula (2) in the presence of sulfur and a base, to form the bicyclic aminothiophene carboxylic acid ester of formula (35). Reaction of this compound with either formamidine or formamide gives the tricyclic thiopyrimidone of formula (36). Reaction of the formula (36) compound with a halogenating agent such as POCl₃ gives the chloro derivative of formula (37). The tricyclic compound of formula (37) is allowed to react with a substituted aniline of formula (7) in the presence of a base and a polar solvent such as ethanol to give the intermediate of formula (38). Hydrolysis of (38) under aqueous acidic conditions provides the ketone of formula (39). Oxidation of (39) with using oxidizing reagent such as DDQ, DMSO, and tetramethylene sufoxide gives a phenol intermediate of formula (40). This intermediate is then reacted with an electrophile such as a substituted alkyl halide, sulfonate, and epoxide, to give the compound of formula (41).

The compounds according to the invention exhibit an unforeseeable, useful pharmacological and pharmacokinetic activity spectrum. They are therefore suitable for use as medicaments for the treatment or prophylaxis of disorders in humans and animals.

In another embodiment, the present invention provides a medicament containing at least one compound according to the invention. In another embodiment, the present invention provides a medicament containing at least one compound according to the invention together with one or more pharmacologically safe excipient or carrier substances, and also their use for the abovementioned purposes.

The active compound can act systemically and/or locally. For this purpose it can be administered in a suitable manner, such as for example by oral, parenteral, pulmonary, nasal, sublingual, lingual, buccal, rectal, dermal, transdermal, ophtalmic or otic administration or in the form of an implant or stent. The active compound can be administered in forms suitable for these modes of administration.

Suitable forms of oral administration are those according to the prior art which function by releasing the active compound rapidly and/or in a modified or controlled manner and which contain the active compound in a crystalline and/or amorphous and/or dissolved form, such as for example tablets (which are uncoated or coated, for example with enteric coatings or coatings which dissolve after a delay in time or insoluble coatings which control the release of the active compound), tablets or films/wafers which disintegrate rapidly in the oral cavity or films/lyophilisates, capsules (e.g. hard or soft gelatin capsules), dragées, pellets, powders, em uLions, suspensions and solutions. An overview of application forms is given in Remington's Pharmaceutical Sciences, 18$^{th}$ ed. 1990, Mack Publishing Group, Enolo.

Parenteral administration can be carried out by avoiding an absorption step (e.g. by intravenous, intraarterial, intracardial, intraspinal or intralumbar administration) or by including absorption (e.g. by intramuscular, subcutaneous, intracutaneous or intraperitoneal administration). Suitable parenteral administration forms are for example injection and infusion formulations in the form of solutions, suspensions, em uLions, lyophilisates and sterile powders. Such parenteral pharmaceutical compositions are described in Part 8, Chapter 84 of Remington's Pharmaceutical Sciences, 18$^{th}$ ed. 1990, Mack Publishing Group, Enolo.

Suitable forms of administration for the other modes of administration are for example inhalation devices (such as for example powder inhalers, nebulizers), nasal drops, solutions and sprays; tablets or films/wafers for lingual, sublingual or buccal administration or capsules, suppositories, ear and eye preparations, vaginal capsules, aqueous suspensions (lotions or shaking mixtures), lipophilic suspensions, ointments, creams, transdermal therapeutic systems, milky lotions, pastes, foams, dusting powders, implants or stents.

The active compounds can be converted into the above-mentioned forms of administration in a manner known to the skilled man and in accordance with the prior art using inert, non-toxic, pharmaceutically suitable auxiliaries. The latter include for example excipients (e.g. microcrystalline cellulose, lactose, mannitol, etc.), solvents (e.g. liquid polyethylene glycols), em uLifiers and dispersants or wetting agents (e.g. sodium dodecyl sulfate, polyoxysorbitan oleate etc.), binders (e.g. polyvinyl pyrrolidone), synthetic and/or natural polymers (e.g. albumin), stabilizers (e.g. antioxidants, such as, for example, ascorbic acid), dyes (e.g. inorganic pigments such as iron oxides) or taste- and/or odour-corrective agents.

In general it has proven advantageous for parenteral administration to administer daily quantities of approximately from 0.001 to 300 mg/kg body weight, and preferably approximately from 0.10 to 150 mg/kg body weight in order to obtain effective results.

It may however be necessary to deviate from the above-mentioned quantities, depending on the body weight, mode of administration, the individual patient response to the active compound, the type of preparation and the time or interval of administration.

If used as active compounds, the compounds according to the invention are preferably isolated in more or less pure form, that is more or less free from residues from the synthetic procedure. The degree of purity can be determined by methods known to the chemist or pharmacist (see Remington's Pharmaceutical Sciences, 18$^{th}$ ed. 1990, Mack Publishing Group, Enolo). Preferably the compounds are greater than 99% pure (w/w), while purities of greater than 95%, 90% or 85% can be employed if necessary.

The percentages in the tests and examples which follows are, unless otherwise stated, by weight (w/w); parts are by weight. Solvent ratios, dilution ratios and concentrations reported for liquid/liquid solutions are each based on the volume.

A. EXAMPLES

Abbreviations and Acronyms

When the following abbreviations are used throughout the disclosure, they have the following meaning:

| | |
|---|---|
| AcOH | Acetic acid |
| ACN | acetonitrile |
| anhyd | anhydrous |
| CDCl$_3$-d | chloroform-d |
| CD$_2$Cl$_2$-d$_4$ | methylene chloride-d$_4$ |
| CDI | 1,1'-dicarbonyldimidazole |
| Celite ® | registered trademark of Celite Corp. brand of diatomaceous earth |
| DCM | methylene chloride |
| DDQ | 2,3-dichloro-5,6-dicyano-1,4-benzoquinone |
| DIBAL-H | diisobutylaluminum hydride |
| DMF | N,N-dimethyl formamide |
| DMSO-d$_6$ | dimethylsulfoxide-d$_6$ |
| EDCI | 1-(3-Dimethylaminopropyl)-3-ethylcarbodiimide hydrochloride |
| EtOAc | ethyl acetate |
| EtOH | ethanol |
| equiv | equivalent(s) |
| h | hour(s) |
| $^1$H NMR | proton nuclear magnetic resonance |
| HCl | hydrochloric acid |
| Hex | hexanes |
| HOBT | 1-hydroxybenzotriazole hydrate |
| HPLC | high performance liquid chromatography |
| IPA | isopropyl alcohol |
| LCMS | liquid chromatography/mass spectroscopy |
| MeOH | methanol |
| min | minute(s) |
| MgSO$_4$ | Magnesium Sulfate |
| MS | mass spectrometry |
| MTBE | tert-butyl methyl ether |
| Na$_2$CO$_3$ | Sodium carbonate |
| NaHCO$_3$ | Sodium bicarbonate |
| NaOH | Sodium Hydroxide |
| Na$_2$SO$_4$ | Sodium Sulfate |
| NBS | N-bromosuccinimide |
| NMO | 4-methylmorpholine n-oxide |
| Pd/C (Pd—C) | palladium on carbon |
| R$_f$ | TLC retention factor |
| Rh/Al$_2$O$_3$ | Rhodium on alumina |
| Rochelle's salt | sodium potassium tartrate |
| rt | room temperature |
| RT | retention time (HPLC) |
| satd | saturated |
| TFA | trifluoroacetic acid |
| THF | tetrahydrofuran |
| TLC | thin layer chromatography |

General Analytical Procedures

The structure of representative compounds of this invention were confirmed using the following procedures.

Electron impact mass spectra (EI-MS) were obtained with a Hewlett Packard® 5989A mass spectrometer equipped with a Hewlett Packard® 5890 Gas Chromatograph with a J & W DB-5 column (0.25 uM coating; 30 m×0.25 mm). The ion source is maintained at 250° C. and spectra were scanned from 50-800 amu at 2 sec per scan.

High pressure liquid chromatography-electrospray mass spectra (LC-MS) 110 were obtained using either a:

(A) Hewlett-Packard® 1100 HPLC equipped with a quaternary pump, a variable wavelength detector set at 254 nm, a YMC pro C-18 column (2×23 mm, 120 A), and a Finnigan®

LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flow rate of 1.0 mL/min is used with an initial hold of 0.5 minutes and a final hold at 95% B of 0.5 minutes. Total run time is 6.5 minutes.

or (B) Gilson® HPLC system equipped with two Gilson 306 pumps, a Gilson 215 Autosampler, a Gilson® diode array detector, a YMC Pro C-18 column (2×23 mm, 120 A), and a Micromass LCZ single quadrupole mass spectrometer with z-spray electrospray ionization. Spectra were scanned from 120-800 amu over 1.5 seconds. ELSD (Evaporative Light Scattering Detector) data is also acquired as an analog channel. The eluents were A: 2% acetonitrile in water with 0.02% TFA and B: 2% water in acetonitrile with 0.018% TFA. Gradient elution from 10% B to 90% over 3.5 minutes at a flowrate of 1.5 mL/min is used with an initial hold of 0.5 minutes and a final hold at 90% B of 0.5 minutes. Total run time is 4.8 minutes. An extra switching valve is used for column switching and regeneration.

Routine one-dimensional NMR spectroscopy is performed either on 300 MHz Varian® Mercury-plus or on 400 MHz Varian® Mercury-plus spectrometers. The samples were dissolved in deuterated solvents obtained from Cambridge Isotope Labs®, and transferred to 5 mm ID Wilmad® NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$-$d_3$, 3.30 ppm for $CD_3OD$-$d_4$, 5.32 ppm for $CD_2Cl_2$-$d_4$ and 7.26 ppm for $CDCl_3$-d for $^1H$ spectra.

Preparation of Starting Materials

Preparation of
5-amino-1-N-(3-fluorobenzyl)indazole

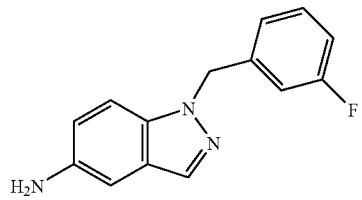

5-nitroindazole (15 g, 92 mmol, 1 eq), 3-fluorobenzylbromide (14.7 mL, 119.5 mmol, 1.3 eq) and potassium carbonate 25.4 g (184 mmol, 2 equiv) were suspended in 150 mL acetonitrile. The reaction mixture was stirred at 70° C. for 12 h, and then allowed to cool to rt. The resultant solid was filtered and washed with $CH_2Cl_2$, and the filtrate concentrated in vacuo. The crude mixture of regioisomeric products was purified by column chromatography (5:1 to 4:1 Hex/EtOAc), yielding 5-nitro-1-N-(3-fluorobenzyl)indazole (7.9 g, 32%) and 5-nitro-2-N-(3-fluorobenzyl) indazole (9.2 g, 37%) as yellow solids.

5-nitro-1-N-(3-fluorobenzyl)indazole (7.9 g, 29.1 mmol, 1 equiv) and iron (8.13 g, 145.6 mmol, 5 equiv) were mixed in 200 mL acetic acid and 50 mL EtOAc, and were stirred at rt for 36 h. The reaction mixture was filtered through a pad of Celite®. The filtrate was concentrated in vacuo to 10 mL volume. The contents were diluted with water (10 mL) and neutralized with saturated $Na_2CO_3$ solution. The solution was extracted with EtOAc (3×500 mL), the combined organic layers dried over $MgSO_4$, filtered, and concentrated in vacuo. The resulting crude material was purified by column chromatography eluting with hexanes/EtOAC (4:1 to 3:1) to give 5-amino-1-N-(3-fluorobenzyl)indazole (5.32 g, 76%) as a light brown solid. $^1$H-NMR (DMSO-$d_6$) δ 7.72 (s, 1H), 7.22-7.36 (m, 2H), 6.87-7.05 (m, 3H), 6.70-6.77 (m, 2H), 5.48 (s, 2H), 4.78 (br s, 2H); LCMS RT=1.66 min; [M+H]$^+$=242.2.

1-Pyridin-2-ylmethyl-1H-indazol-5-ylamine was prepared using the same method described above and the appropriate reagents; LC/MS RT=1.03 min; [M+H]$^+$=225.2.

Preparation of
3-Chloro-4-(thiazol-4-ylmethoxy)-phenylamine;
hydrochloride

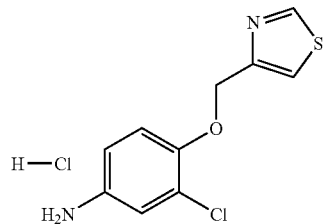

Step 1: Preparation of
3-Chloro-4-(thiazol-4-ylmethoxy)-phenylamine
hydrochloride

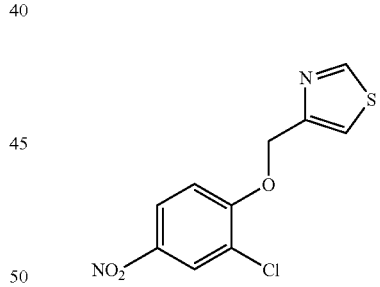

To a solution of 2-chloro-4-nitrophenol (1.00 g, 5.76 mmol) in acetonitrile (125 mL) were added 4-chloromethylthiazole hydrochloride (1.08 g, 6.34 mmol), Potassium carbonate (2.39 g, 17.29 mmol) and sodium iodide (1.73 g, 11.52 mmol). The reaction mixture was stirred at 60 C overnight. Water (60 mL) and DCM (10 mL) were added. After all solid material dissolved, layers formed were separated. The organic layer was washed with water and brine, dried over Na2SO4 and concentrated down to give the required material as a light yellow solid (1.29 mg, 83%). $^1$H-NMR (CD$_2$Cl$_2$) δ 8.87 (d, 1H), 8.32 (d, 1H), 8.16 (dd, 1H), 7.54-7.56 (m, 1H), 7.22 (d, 1H), 5.33-5.34 (m, 2H); LCMS RT=3.01 min; [M+H]$^+$=271.0.

Step 2:
3-Chloro-4-(thiazol-4-ylmethoxy)-phenylamine; hydrochloride

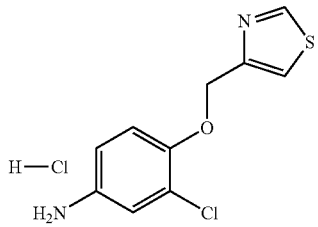

A mixture of A (1.00 g, 3.69 mmol), iron powder (2.06 g, 36.94 mmol), 2 M HCl (1.85 mL) and 85% ethanol (30 mL) was refluxed for 2.5 hours. The mixture was cooled down to room temperature, filtered through a pad of celite and concentrated under vacuum to give the required material as a dark brown solid (0.89 g, 87%). $^1$H-NMR (CD$_3$OD) δ 8.99 (d, 1H), 7.59-7.60 (m, 1H), 6.89 (d, 1H), 6.77 (d, 1H), 6.58 (dd, 1H), 5.15 (s, 2H); LCMS RT=1.28 min; [M+H]$^+$=241.0.

Example 1

Preparation of ethyl[4-({3-chloro-4-[(3-fluorobenzyl)oxy]phenyl}amino)[1]benzothieno[2,3-d]pyrimidin-7-yl]acetate

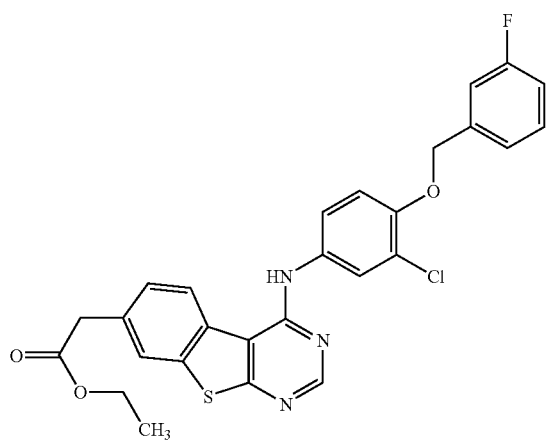

Step 1. Preparation of ethyl 1,4-dioxaspiro[4.5]dec-8-ylideneacetate

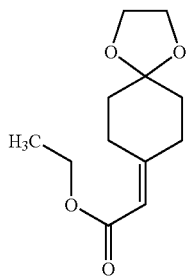

To a solution of THF (18 mL) under argon was added 0.38 g (47.8 mmol, 5 equiv) of LiH, followed by slow addition of 8.78 g (47.8 mmol, 5 equiv) of triethyl phosphonoacetate. The solution was stirred at rt for 1 h and 1.49 g (9.6 mmol, 1 equiv) of 1,4-dioxa-spiro[4.5]decan-8-one was added and the solution was heated at 65° C. for 16 h. Upon cooling the solution was treated with MeOH (10 mL) and water (5 mL) and concentrated in vacuo. The resulting yellow oil was purified by silica gel chromatography eluting with 4:1 Hex/EtOAc to yield 1.89 g (93%) of a clear oil. $^1$H-NMR (CDCl$_3$-d) δ 5.67 (s, 1H), 4.16 (t, 2H), 3.99 (m, 4H), 3.02 (m, 2H), 2.39 (m, 2H), 1.78 (m, 4H), 1.29 (t, 3H); LCMS RT=2.56 min, [M+H]$^+$=226.9.

Step 2. Preparation of ethyl 1,4-dioxaspiro[4.5]dec-8-ylacetate

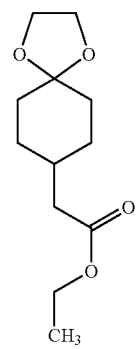

To a suspension of Pd/C (182 mg, 10% by weight) in EtOH (100 mL) was added a solution of) ethyl 1,4-dioxaspiro[4.5]dec-8-ylideneacetate (1.82 g, 8.0 mmol, 1 equiv in EtOH (5 mL) was added via syringe under argon. The flask was charged with hydrogen (3 times) and left stirring for 16 h. The flask was evacuated and charged with argon (3 times) and the solution was filtered through a pad of Celite® washing with EtOH (200 mL). The solution was evaporated under reduced pressure yielding 1.74 g (95%) of a clear oil. $^1$H-NMR (CDCl$_3$-d) δ 4.13 (q, 2H), 3.95 (m, 4H), 2.24 (m, 2H), 1.96 (m, 1H), 1.75 (m, 4H), 1.58 (m, 2H), 1.31 (m, 2H), 1.27 (t, 3H); TLC R$_f$=0.20 (1:9 EtOAc/Hex).

Step 3. Preparation of ethyl (4-oxocyclohexyl)acetate

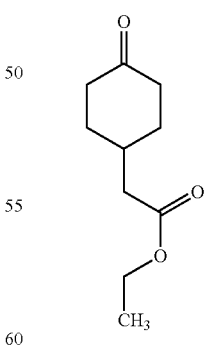

This material was prepared by either of two methods described below.

Method A.

To a solution of 10 g (43.8 mmol, 1 equiv) of ethyl 1,4-dioxaspiro[4.5]dec-8-ylacetate in acetone (720 mL) was added aqueous HCl (1N, 180 mL) The reaction was heated at reflux for 2 h. Upon cooling the solution was diluted with EtOAc (100 mL) and washed with water (100 mL). The water layer was back extracted with EtOAc (2×100 mL) and the organic layers were combined, dried (MgSO$_4$), filtered and concentrated to yield 7.57 g (94%) of a clear oil. $^1$H-NMR (CDCl$_3$-d) δ 4.16 (q, 2H), 2.40 (m, 4H), 2.32 (m, 2H), 2.28 (m, 1H), 2.10 (m, 2H), 1.49 (m, 2H), 1.28 (t, 3H); TLC R$_f$=0.32 (3:7 EtOAc/Hex).

Method B.

Ethyl(4-hydroxyphenyl)acetate (50 g, 277 mmol) was dissolved in 150 mL of ethanol in a Parr bottle with Rh/Al$_2$O$_3$ (1.00 g, 5 wt %, Aldrich Lot:07727AB). The suspension was hydrogenated on a Parr shaker at 60 psi. After 48 h, starting material was still present, so additional Rh/Al$_2$O$_3$ (4.00 g) was added. The suspension was hydrogenated for another 8 h, at which time a sample analyzed by $^1$H NMR indicated the reaction was complete. The reaction mixture was filtered through Celite® and rinsed with ethanol (450 mL). The reaction mixture was concentrated to afford a clear colorless oil (55.0 g, quantitative).

The resulting ethyl (4-hydroxycyclohexyl)acetate (45.0 g, 240 mmol) was dissolved in AcOH (160 mL) and slowly treated with NaOCl (171 mL, 10-13% available chlorine, ~1.7 M, ~290 mmol) to maintain the temperature below 30° C. Brine (500 mL) was added to the solution and the aqueous layer was extracted with EtOAc (3×500 mL). The organic layers were combined, washed with brine (500 mL), concentrated to an oil and chased with heptane. $^1$H NMR indicated ~1 equivalent of AcOH. The oil was redissolved in EtOAc (500 mL), washed with sat. NaHCO$_3$ (2×250 mL) and brine (200 mL). The organic layer was collected, dried (Na$_2$SO$_4$), filtered, and concentrated to yield 40.7 g (92%) of a clear colorless oil. $^1$H NMR (DMSO-d$_6$) δ4.05 (q, 2H), 2.39 (dt, 2H), 2.30 (d, 2H), 2.19-2.14 (m, 3H), 1.96-1.90 (m, 2H), 1.39 (dq, 2H), 1.18 (t, 3H). GCMS (EI) RT=9.3 min, [M]+=184.

Step 4. Preparation of ethyl 2-amino-6-(2-ethoxy-2-oxoethyl)-4,5,6,7-tetrahydro-1-benzothiophene-3-carboxylate

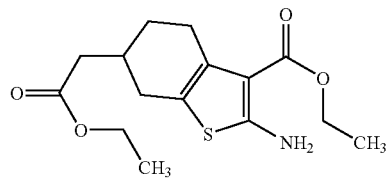

Ethyl(4-oxocyclohexyl)acetate (40.7 g, 221 mmol) was dissolved in ethanol (450 mL). Ethyl cyanoacetate (25.0 g, 221 mmol), morpholine (19.2 g, 221 mmol), and sulfur (7.08 g, 221 mmol) were added to the reaction flask in that order. The reaction was stirred at room temperature for 3 days, during which time the suspension turned into a clear solution. The reaction mixture was concentrated on a rotavap to 20% of the original volume. The solution was diluted with EtOAc (1 L), washed once with dilute brine (500 mL water:50 mL sat. brine), then with sat. brine (100 mL). The organic layer was dried with sodium sulfate, filtered, and concentrated to obtain a viscous light brown oil (69.9 g, quantitative). $^1$H NMR (CDCl$_3$-d) δ 5.96 (s, 2H), 4.25 (q, 2H), 4.15 (q, 2H), 2.87 (m, 1H), 2.65 (m, 2H), 2.32 (m, 4H), 1.91 (m, 1H), 1.46 (m, 1H), 1.34 (t, 3H)), 1.28 (t, 3H); LCMS RT=3.17 min, [M+H]+=312.0.

Step 5. Preparation of ethyl (4-oxo-3,4,5,6,7,8-hexahydro[1]benzothieno[2,3-d]pyrimidin-7-yl)acetate

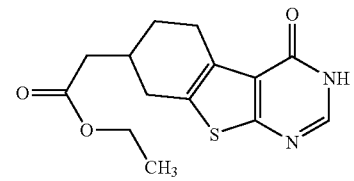

Formamide (310 mL) was added to ethyl 2-amino-6-(2-ethoxy-2-oxoethyl)-4,5,6,7-tetrahydro-1-benzothiophene-3-carboxylate (61.2 g, 197 mmol) and the biphasic mixture was heated at 180° C. in an oil bath overnight. The heat was turned off and the reaction solution was allowed to cool. At 60° C., the reaction mixture was seeded and lots of solid quickly precipitated. Upon reaching room temperature the reaction mixture was filtered (very slowly), and rinsed with water (2×150 mL). The damp solid was placed in a vacuum oven and dried at 50° C. overnight to yield a light tan solid (39.3 g, 68.4%). $^1$H NMR (DMSO-d$_6$) δ 12.31 (s, 1H), 7.99 (s, 1H), 4.09 (q, 2H), 3.06 (m, 1H), 2.87 (m, 1H), 2.75 (m, 1H), 2.40 (m, 3H), 2.19 (m, 1H), 1.89 (m, 1H), 1.47 (m, 1H), 1.19 (t, 3H); LCMS RT=2.40 min, [M+H]+=293.1.

Step 6. Preparation of (4-Oxo-3,4-dihydro-benzo[4,5]thieno[2,3-d]pyrimidin-7-yl)-acetic acid ethyl ester

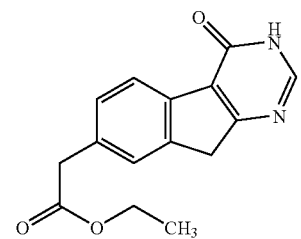

(4-Oxo-3,4,5,6,7,8-hexahydro[1]benzothieno[2,3-d]pyrimidin-7-yl)acetate (5 g, 17.10 mmol, from step 2) was added to DDQ (9.71 g, 42.76 mmol, 2.5 equiv) in 1,4-dioxane (50 mL) solution under argon. The reaction mixture was heated to 90° C. for 15 h. The mixture was then allowed to cool to rt and the brown solid precipitated from solution. The solid was filtered and washed with 1,4-dioxane (2×30 mL). The filtrate was concentrated in vacuo. Saturated aqueous NaHCO$_3$ (150 mL) was then slowly poured into the concentrated filtrate at 0° C. The mixture was stirred at 0° C. for 10 min then extracted with DCM (3×300 mL). The combined organic layer was washed with saturated aqueous NaHCO$_3$ (100 mL), brine (30 mL) and dried (Na$_2$SO$_4$), then concentrated in vacuo. Ethyl ether (2×15 mL) was used to triturated the product. After drying, 1.78 g (6.18 mmol, 35%) of the desired product was obtained as a brown solid and it was used without further purification. 1H-NMR (CD3OD) δ 8.46 (d, J=8.1 Hz, 1H), 8.18 (s, 1H), 7.84 (s, 1H), 7.43 (d, J=8.2 Hz, 1H), 4.14 (q, 2H), 3.79 (s, 2H), 1.25 (t, 3H), LCMS RT=2.52 min, [M+H]+=289

Step 7. Preparation of (4-Chloro-benzo[4,5]thieno[2,3-d]pyrimidin-7-yl)-acetic acid ethyl ester

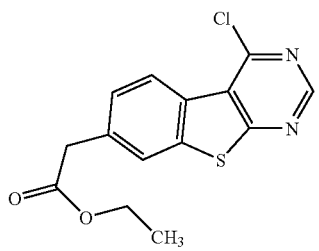

To a solution of (4-oxo-3,4-dihydro-benzo[4,5]thieno[2,3-d]pyrimidin-7-yl)-acetic acid ethyl ester (1.78 g, 6.17 mmol, 1 equiv, from step 3) in toluene (15 mL) were added diisopropylethylamine (1.18 mL, 6.79 mmol, 1.1 equiv) and phosphorous oxychloride (0.63 mL, 6.79 mmol, 1.1 equiv) at 0° C. under argon. The flask was equipped with a reflux condenser and heated at 80° C. for 5 h. The reaction mixture was cooled to rt and quenched with ice/saturated aqueous NaHCO$_3$. The resulting mixture was extracted with EtOAc (3×80 mL). The combined organic layers was dried over sodium sulfate and concentrated in vacuo. The crude material was purified by flash chromatography (20% EtOAc/hexane) to yield 1.12 g (3.6 mmol, 56%) of a light yellow solid. $^1$H-NMR (DMSO-d6) δ 9.01 (s, 1H), 8.64 (d, J=8.6 Hz, 1H), 8.15 (s, 1H), 7.61 (d, J=8.6 Hz, 1H), 4.10 (q, 2H), 3.92 (s, 2H), 1.20 (t, 3H), LCMS RT=3.19 min, [M+H]$^+$=307

Step 8. Preparation of 3-chloro-4-(3-fluoro-benzyloxy)-phenylamine

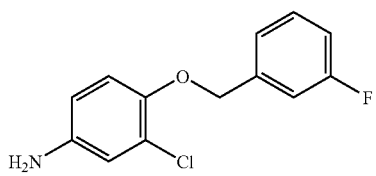

To 90 mL CH$_3$CN was added 2-chloro-4-nitrophenol (15 g, 86.4 mmol) followed by potassium carbonate (17.9 g, 129.6 mmol). To the stirring suspension was added via dropping funnel a 10 mL CH$_3$CN solution of 3-fluoro-benzylbromide (16.3 g, 86.4 mmol). The contents were stirred and heated at 70° C. for 18 h, after which time the bright yellow mixture was allowed to cool to rt. The yellow contents were poured onto water (200 mL) and stirred, upon which solid formation occurs. The solid was filtered and filter cake washed with additional water (50 mL). The collected solid was dried in vacuo, yielding 2-chloro-1-(3-fluoro-benzoyloxy)-4-nitrobenzene (23 g, 94%) as a white solid.

2-Chloro-1-(3-fluoro-benzoyloxy)-4-nitro-benzene (10 g, 35.5 mmol) was suspended in 50 mL acetic acid and 150 mL EtOAc in a 500 mL flask. Iron (9.9 g, 177.5 mmol) was added to this suspension, and the mixture stirred at rt overnight. The reaction mixture was filtered through a thin pad of Celite®. The filtrate was concentrated in vacuo and neutralized with saturated Na$_2$CO$_3$ aq solution, followed by EtOAc extraction. The organic layer was washed with brine, dried over Na$_2$SO$_4$, and concentrated in vacuo. The resulting crude material was purified by flash chromatography eluting with 15% EtOAc/hexanes yielding 3-chloro-4-(3-fluoro-benzyloxy)-phenylamine as a brown solid [8.5 g, 95%, TLC R$_f$=0.4, 30% EtOAc/Hex. (3:7)]. $^1$H-NMR (DMSO-d$_6$) δ 4.94 (s, 2H), 5.00 (s, 2H), 6.40 (dd, 1H), 6.60 (s, 1H), 6.87 (d, 1H), 7.10-7.18 (m, 1H), 7.20-7.28 (m, 2H), 7.37-7.44 (m, 1H).

Step 9. Preparation of ethyl[4-({3-chloro-4-[(3-fluorobenzyl)oxy]phenyl}amino)[1]benzothieno[2,3-d]pyrimidin-7-yl]acetate

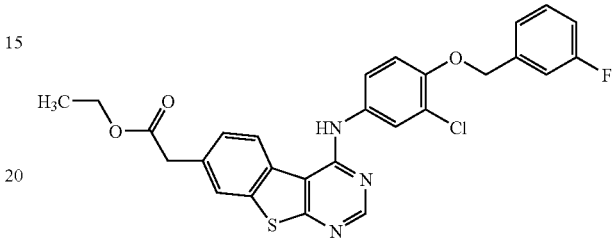

3-Chloro-4-(3-fluoro-benzyloxy)-phenylamine (919 mg, 3.65 mmol, 1 eq, from step 5) was added to (4-chloro-benzo[4,5]thieno[2,3-d]pyrimidin-7-yl)-acetic acid ethyl ester (1.12 g, 3.65 mmol, 1 eq, from step 4) in 15 mL of isopropyl alcohol. The reaction mixture was irradiated in a microwave reactor at 150° C. for 20 min. The mixture was allowed to cool to rt then concentrated in vacuo. Methanol was added to the residue and some yellow solid precipitate out from the solution. The solid was filtered, washed with methanol (3 mL) and EtOAc (3 mL) then dried on vacuum oven for 14 h to obtain 858 mg (1.6 mmol, 45%) of yellow solid as product. 1H-NMR (DMSO-d6) δ 9.01 (s, 1H), 8.52 (s, 1H), 8.51 (d, J=8.6 Hz, 1H), 8.00 (s, 1H), 7.75 (d, J=2.0 Hz, 1H), 7.54 (dd, J=2.5, 9.3 Hz, 1H), 7.51-7.43 (m, 2H), 7.31 (m, 2H), 7.24 (d, J=8.9 Hz, 1H), 7.17 (td, 1H), 5.27 (s, 2H), 4.10 (q, 2H), 3.85 (s, 2H), 1.20 (t, 3H); LCMS RT=4.06 min, [M+H]$^+$=522

Using the method described above and the appropriate starting materials, examples 81 and 134 were similarly prepared.

Example 2

Preparation of 2-[4-({3-chloro-4-[(3-fluorobenzyl)oxy]phenyl}amino)[1]benzothieno[2,3-d]pyrimidin-7-yl]ethanol

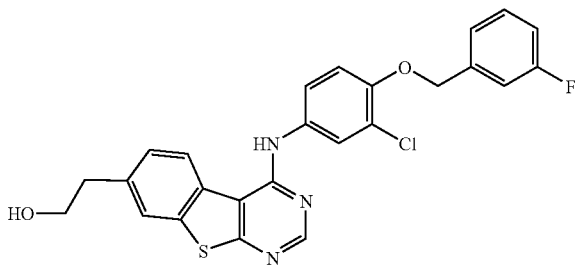

To a solution of ethyl[4-({3-chloro-4-[(3-fluorobenzyl)oxy]phenyl}amino)[1]benzothieno[2,3-d]pyrimidin-7-yl]acetate (858 mg, 1.64 mmol, 1 equiv) in THF (10 mL) was added 1M solution of diisobutylaluminum hydride in hexanes (6.6 mL, 6.57 mmol, 4 equiv) at 0° C. under nitrogen. The reaction was stirred at 0° C. for 1 h. The reaction mixture was quenched with Rochelle's salt followed by extraction with EtOAc (3×50 mL). The combined organic layers were washed with brine (100 mL) and water (100 mL), dried over sodium sulfate and concentrated in vacuo. The crude material was purified by flash chromatography (40% EtOAc/hexane then 100% EtOAc) to yield a light yellow (845 mg, 48%). 1H-NMR (CD$_3$OD) δ 8.35 (s, 1H), 8.18 (d, J=8.6 Hz, 1H), 7.76 (s, 1H), 7.71 (d, J=2.0 Hz, 1H), 7.43-7.34 (m, 3H), 7.27-7.20 (m, 2H), 7.03 (m, 2H), 5.12 (s, 2H), 3.83 (t, 2H), 2.95 (t, 2H); LCMS RT=3.56 min, [M+H]$^+$=480

Using the method described above and the appropriate starting materials, examples 82, 127, 132, and 133 were similarly prepared.

Example 3

Preparation of 7-(2-bromoethyl)-N-{3-chloro-4-[(3-fluorobenzyl)oxy]phenyl}[1]benzothieno[2,3-d]pyrimidin-4-amine

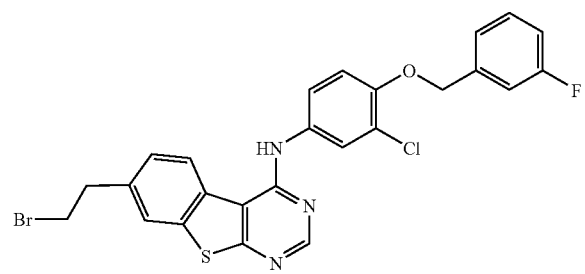

To a solution of 2-[4-({3-chloro-4-[(3-fluorobenzyl)oxy]phenyl}amino) [1]benzothieno[2,3-d]pyrimidin-7-yl]ethanol (700 mg, 1.46 mmol, 1 equiv) in THF (10 mL) were added triphenylphosphine (0.82 g, 3.12 mmol, 3 equiv) and carbon tetrabromide (1.03 g, 3.12 mmol, 3 equiv). The resulting solution was stirred at rt for 14 h and the solvent was evaporated under reduced pressure. The resulting crude material was purified by flash chromatography eluting with 9:1 CH$_2$Cl$_2$/EtOAc yielding a light yellow solid (688 mg, 1.27 mmol, 87%). $^1$H-NMR (CDCl$_3$) δ 8.60 (s, 1H), 7.96 (d, J=8.6 Hz, 1H), 7.81 (s, 1H), 7.75 (d, J=2.7 Hz, 1H), 7.50-7.44 (m, 3H), 7.39-7.34 (m, 1H), 7.23 (m, 2H), 7.03 (td, 1H), 7.00 (d, J=9.0 Hz, 1H), 5.12 (s, 2H), 3.68 (t, 2H), 3.36 (t, 2H); LCMS RT=4.26 min, [M+H]$^+$=541/544

Using the method described above and the appropriate starting materials, example 83 was similarly prepared.

Example 7

Preparation of [3-chloro-4-(3-fluoro-benzyloxy)-phenyl]-[7-(2-imidazol-1-yl-ethyl)-benzo[4,5]thieno[2,3-d]pyrimidin-4-yl]-amine

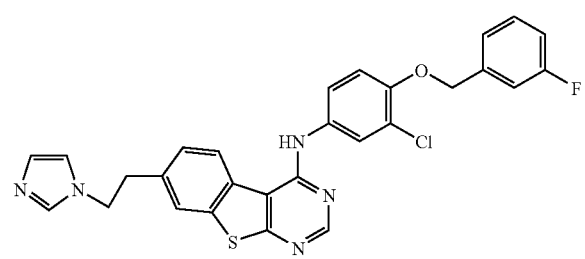

To a solution of 7-(2-bromoethyl)-N-{3-chloro-4-[(3-fluorobenzyl)oxy]phenyl}[1]benzothieno[2,3-d]pyrimidin-4-amine (40 mg, 0.07 mmol, 1 equiv) in DMF were added sodium iodide (11 mg, 0.07 mmol, 1 equiv), sodium carbonate (16 mg, 0.15 mmol, 2 equiv), and imidazole (10 mg, 0.15 mmol, 2 equiv). The resulting mixture was heated at 80° C. for 14 h. The reaction was cooled to rt and then concentrated in vacuo. The resulting crude material was purified by prep-TLC (10% methanol/DCM) and afforded a yellow solid (17.9 mg, 0.03 mmol, 45%). $^1$H-NMR (CD3OD) δ 8.40 (s, 1H), 8.24 (d, J=8.3 Hz, 1H), 7.71 (m, 2H), 7.45-7.36 (m, 3H), 7.28 (d, J=8.1 Hz, 2H), 7.23 (d, J=9.6 Hz, 1H), 7.10 (d, J=8.1 Hz, 1H), 7.09 (s, 1H), 7.04 (td, 1H), 6.92 (s, 1H), 5.12 (s, 2H), 4.35 (t, 2H), 3.23 (t, 2H); LCMS RT=3.22 min, [M+H]$^+$=530

Using the method described above and the appropriate starting materials, examples 4-12, 15-24, 84-93, and 128-129 were similarly prepared.

Example 13

Preparation of 7-bromo-N-{3-chloro-4-[(3-fluorobenzyl)oxy]phenyl}[1]benzothieno[2,3-d]pyrimidin-4-amine

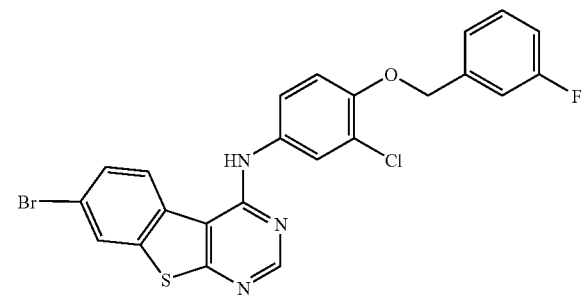

Step 1. Preparation of ethyl 2-amino-4,5,6,7-tetrahydro-1-benzothiophene-3-carboxylate

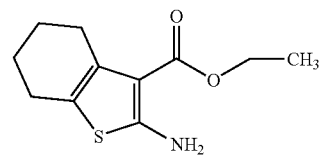

Cyclohexanone (200 g, 2.04 mol), ethyl cyanoacetate (231 g, 204 mol), diethylamine (149 g, 204 mol), sulfur (65.3 g, 2.04 mol) and ethanol were combined and stirred at room temperature over the weekend. The reaction mixture containing crystalline product was concentrated to ~50% of the original volume on a rotavap. The slurry was filtered and the collected solid was dried on the filter overnight to yield 381 g (83%). $^1$H NMR (DMSO-d$_6$) δ 7.18 (s, 2H), 4.12 (q, 2H), 2.57 (t, 2H), 2.40 (t, 2H), 1.66 (m, 4H), 1.23 (t, 3H); LCMS RT=3.36 min' [M+H]$^+$=226.0.

Step 2. Preparation of ethyl 2-(acetylamino)-4,5,6,7-tetrahydro-1-benzothiophene-3-carboxylate

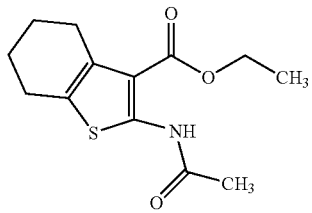

Ethyl 2-amino-4,5,6,7-tetrahydro-1-benzothiophene-3-carboxylate (100 g, 444 mmol) and acetic anhydride (227 g, 2.2 mol) were heated at reflux for ~15 minutes and then allowed to cool to room temperature overnight. The reaction mixture containing white solid was filtered. The solid was rinsed with water (2 L) and dried in a vacuum oven for several hours at ~45° C. to yield a white crystalline solid (96 g, 81%). $^1$H NMR (DMSO-$d_6$) δ 4.26 (q, 2H), 2.69 (t, 2H), 2.57 (t, 2H), 2.20 (s, 3H), 1.70 (m, 4H), 1.30 (t, 3H), LCMS RT=3.48 min, [M+H]$^+$=268.0.

Step 3. Preparation of ethyl 2-amino-1-benzothiophene-3-carboxylate

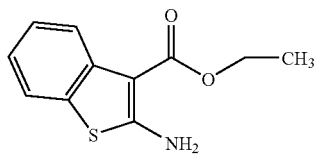

Ethyl 2-(acetylamino)-4,5,6,7-tetrahydro-1-benzothiophene-3-carboxylate (37.0 g, 138 mmol), sulfur (8.9 g, 277 mmol), and dimethyl phthalate (53.8 g, 277 mmol) were heated at 195° C. for ~8 h. The clear solution was allowed to cool overnight to room temperature. Upon returning, a solid cake had formed in the flask and the stirring had stopped. Several unsuccessful attempts were made to get the solid in an easily filtered form. The solid was re-slurried in ethanol (200 mL) and filtered. The solid was then heated in ethanol (500 mL), cooled, and filtered again. Finally, it was heated in toluene with a Dean-Stark trap and filtered. The solid was then dried in a vacuum oven to yield a light yellow solid (12.7 g). A second crop (5.9 g) was obtained by concentrating the toluene filtrate.

The two crops were then deacylated in separate runs by heating in toluene (~0.38 M in substrate) at reflux with pyrrolidine (5 equiv) for ~4 h. Upon completion, the reaction mixtures were combined, concentrated to ~100 mL, and filtered to remove a small amount of particles. The deep red filtrate was poured onto a Biotage 75 L silica gel column and purified via gradient chromatography (10% EtOAc to 25% EtOAc in hexane). The fractions containing the desired product were combined and concentrated to yield a white solid (10.4 g, 34% over two steps). $^1$H NMR (DMSO-$d_6$) δ 7.93 (s, 2H), 7.92 (d, 1H), 7.57 (d, 1H), 7.22 (t, 1H), 7.03 (t, 1H), 4.28 (q, 2H), 1.33 (t, 3H), LCMS RT=3.13 min, [M+H]$^+$=222.0.

Step 4. Preparation of ethyl 2-amino-6-bromo-1-benzothiophene-3-carboxylate

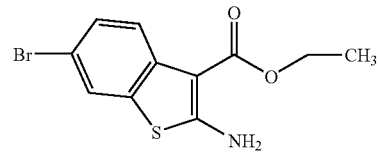

Ethyl 2-amino-1-benzothiophene-3-carboxylate (10.4 g, 44.7 mmol) was dissolved in chloroform (100 mL) and treated with NBS (7.95 g, 44.7 mmol). Upon completion of the reaction, a light tan solid precipitated from the mixture. The slurry was concentrated to ~30% of the original volume on a rotavap and then filtered. The solid was slurried in EtOAc (300 mL) and treated with satd NaHCO$_3$ (200 mL) to obtain two clear phases. The organic phase was washed further with satd NaHCO$_3$ (4X~200 mL) and water (200 mL). The organic layer was collected, dried with sodium sulfate, filtered, and concentrated to yield an off-white solid (9.1 g, 68%). $^1$H NMR (DMSO-$d_6$) δ 8.00 (s, 2H), 7.85 (s, 1H), 7.83 (d, 1H), 7.36 (d, 1H), 4.28 (q, 2H), 1.33 (t, 3H).

Step 5. Preparation of 7-bromo[1]benzothieno[2,3-d]pyrimidin-4(3H)-one

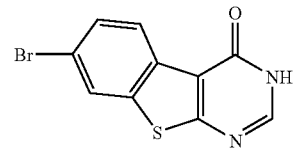

Ethyl 2-amino-6-bromo-1-benzothiophene-3-carboxylate (9.0 g, 27 mmol), formamide (85 mL) and ammonium formate (2.7 g, 43 mmol) were heated in an oil bath at 135° C. overnight. The next morning the reaction mixture was a pastel blue slurry. The reaction mixture was allowed to cool to room temperature and was then filtered. The solid was washed with water, dried by filtration, and finally dried in a vacuum oven overnight at 45° C. to yield a light blue solid (7.8 g, quantitative). $^1$H NMR (DMSO-$d_6$) δ 12.9 (br, 1H), 8.37 (s, 1H), 8.35 (d, 1H), 8.31 (s, 1H), 7.69 (d, 1H); LCMS RT=3.08 min, [M+H]$^+$=281.1.

Step 6 Preparation of 7-bromo-4-chloro[1]benzothieno[2,3-d]pyrimidine

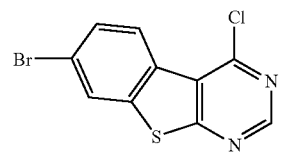

7-Bromo[1]benzothieno[2,3-d]pyrimidin-4(3H)-one (7.80 g, 27.7 mmol), POCl$_3$ (70 mL) and triethylamine (70 mL) were heated in an oil bath at 80° C. for 3 h. The resulting slurry was concentrated on a rotavap, slurried in dichloromethane and poured into 500 mL of satd NaHCO$_3$. The organic phase was then washed with satd NaHCO$_3$, water, and then collected. The initial aqueous phase (pH<1) was basified with 1.0 N NaOH and extracted with dichloromethane. The organic layers were combined, dried with sodium sulfate, filtered, and concentrated under high vacuum to yield a crude brown solid (7.6 g, 91%). $^1$H NMR (DMSO-d$_6$) δ 9.05 (s, 1H), 8.60 (d, 1H), 8.60 (s, 1H), 7.88 (d, 1H).

Step 7 Preparation of 7-bromo-N-{3-chloro-4-[(3-fluorobenzyl)oxy]phenyl}[1]benzothieno[2,3-d]pyrimidin-4-amine

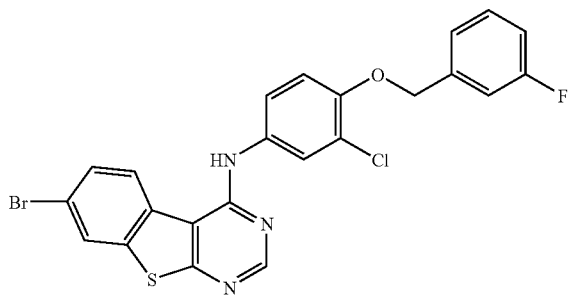

7-Bromo-4-chloro[1]benzothieno[2,3-d]pyrimidine (7.00 g, 23.4 mmol), 3-chloro-4-(3-fluoro-benzyloxy)-phenylamine (5.88 g, 23.4 mmol), and HCl in dioxane (1 mL, 4.0 M) were heated to reflux in IPA (140 mL) for 3 days. The suspension was filtered to collect a light tan solid. The solid was re-suspended in EtOAc (350 mL) and treated with satd NaHCO$_3$ (350 mL) to generate two clear phases. The organic phase was washed with water (350 mL), collected, dried with sodium sulfate, filtered, concentrated on a rotavap, and finally placed under high vacuum to yield an off-white solid (10.34 g, 86%). $^1$H NMR (DMSO-d$_6$) δ 9.06 (s, 1H), 8.53 (s, 1H), 8.49 (d, 1H), 8.43 (s, 1H), 7.74 (d, 1H), 7.71 (s, 1H), 7.50 (d, 1H), 7.47-7.42 (m, 1H), 7.32-7.16 (m, 4H), 5.26 (s, 2H), LCMS RT=4.42 min, [M+H]$^+$=514.3.

Example 14

Preparation of N-{3-chloro-4-[(3-fluorobenzyl)oxy]phenyl}-7-vinyl[1]benzothieno[2,3-d]pyrimidin-4-amine

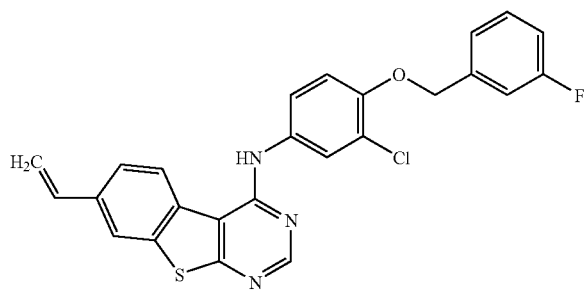

7-Bromo-N-{3-chloro-4-[(3-fluorobenzyl)oxy]phenyl}[1]benzothieno[2,3-d]pyrimidin-4-amine (4.78 g, 9.29 mmol), Pd(PPh$_3$)$_4$ (215 mg, 0.19 mmol), 2,6-di-t-butyl-4-methylphenol (2 mg), tributyl(vinyl)tin (3.24 g, 10.2 mmol), and toluene (50 mL) were heated to reflux for 4 hours. The reaction mixture was cooled and purified by gradient silica gel chromatography (EtOAc:Hex). The relevant fractions were combined and concentrated to yield 3.85 g of an off-white solid which, by $^1$H NMR, contained residual butyl tin species. The solid was re-slurried in 40 mL of MTBE and filtered to obtain an off-white solid (3.09 g, 72%). $^1$H-NMR (CD$_3$OD) δ 8.63 (s, 1H), 7.94 (s, 1H), 7.89 (d, J=8.5 Hz, 1H), 7.76 (d, J=2.9 Hz, 1H), 7.61 (dd, J=1.4, 8.4 Hz, 1H), 7.48 (dd, J=2.9, 8.6 Hz, 1H), 7.36 (m, 1H), 7.23 (m, 2H), 7.14 (s, 1H), 7.03 (td, 1H), 6.99 (d, J=8.9 Hz, 1H), 6.84 (dd, 1H), 5.91 (d, J=17.9 Hz, 1H), 5.41 (d, J=10.8 Hz, 1H), 5.12 (s, 2H), LCMS RT=4.22 min, [M+H]$^+$=462.

Example 25

Preparation of 1-[4-({3-chloro-4-[(3-fluorobenzyl)oxy]phenyl}amino)[1]benzothieno[2,3-d]pyrimidin-7-yl]ethane-1,2-diol

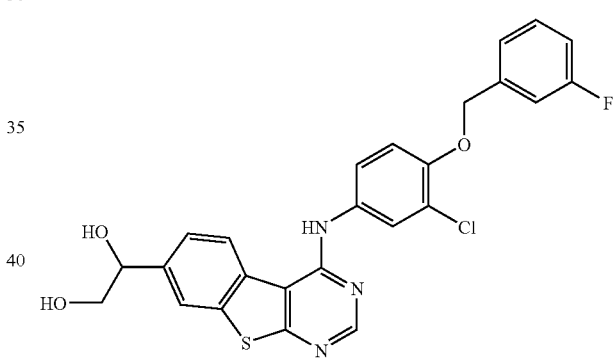

To a solution of N-{3-chloro-4-[(3-fluorobenzyl)oxy]phenyl}-7-vinyl[1]benzothieno[2,3-d]pyrimidin-4-amine (110 mg, 0.23 mmol, 1 equiv) in acetone (4 mL) and water (0.4 mL) were added NMO (33 mg, 0.29 mmol, 1.2 equiv) and catalytic amount of osmium(VIII) tetroxide (2.5 w % in t-BuOH) at rt under N$_2$. The reaction mixture was stirred at rt for 14 h. Sodium sulfite (200 mg) was added to the reaction mixture and stirred for 20 min. The reaction mixture was filtered through a pad of silicon gel with Celite® on top and washed with EtOAc (3×20 mL). The filtrate solution was then concentrated and triturated with DCM to obtain a brown solid (58 mg, 0.12 mmol, 49%). $^1$H-NMR (CD$_3$OD) δ 8.45 (s, 1H), 8.39 (d, J=9.2 Hz, 1H), 8.03 (s, 1H), 7.75 (s, 1H), 7.62 (d, J=8.5 Hz, 1H), 7.48 (d, J=8.5 Hz, 1H), 7.40 (m, 1H), 7.31-7.24 (m, 2H), 7.15 (d, J=8.3 Hz, 1H), 7.05 (t, 1H), 5.22 (s, 2H), 4.09 (m, 1H), 3.72 (m, 2H), LCMS RT=3.59 min, [M+H]$^+$=496

Example 26 & 27

Preparation of (1S)-1-[4-({3-chloro-4-[(3-fluorobenzyl)oxy]phenyl}amino)[1]benzothieno[2,3-d]pyrimidin-7-yl]ethane-1,2-diol and (1R)-1-[4-({3-chloro-4-[(3-fluorobenzyl)oxy]phenyl}amino) [1]benzothieno[2,3-d]pyrimidin-7-yl]ethane-1,2-diol example 26

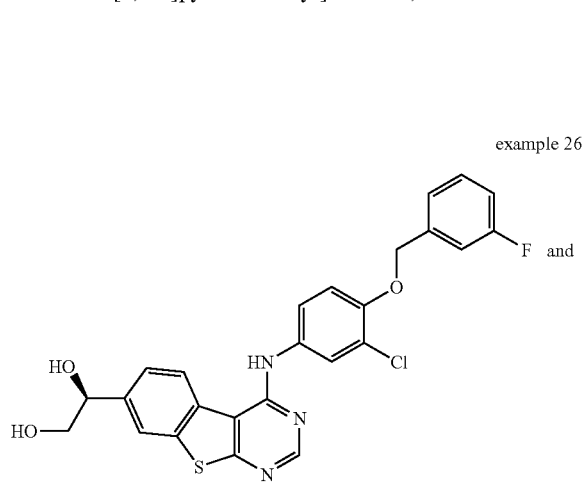

example 27

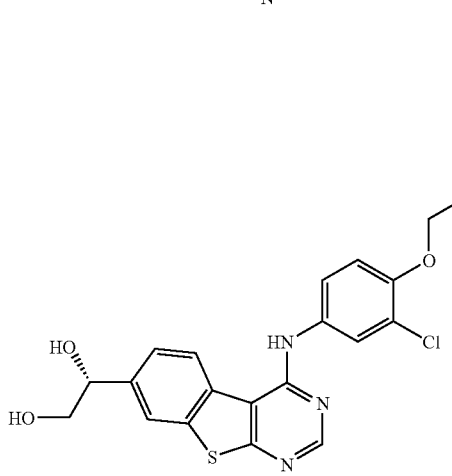

The racemic mixture of 1-[4-({3-chloro-4-[(3-fluorobenzyl)oxy]phenyl}amino) [1]benzothieno[2,3-d]pyrimidin-7-yl]ethane-1,2-diol (240 mg, 0.48 mmol) was separated by chiral HPLC [Conditions: CHiralpak AD 5 micron 20×250 mm. Eluents: A=Hexane, B=3-1 MeOH-EtOH. 50% B (+0.1% ET3N via make-up pump) with Flow 15 mL/min UV 215] to give (1S)-1-[4-({3-chloro-4-[(3-fluorobenzyl)oxy]phenyl}amino)[1]benzothieno[2,3-d]pyrimidin-7-yl]ethane-1,2-diol as a white solid (98.5 mg, 41%) and (1R)-1-[4-({3-chloro-4-[(3-fluorobenzyl)oxy]phenyl}amino)[1]benzothieno[2,3-d]pyrimidin-7-yl]ethane-1,2-diol (95.7 mg, 48%) as a white solid. $^1$H-NMR (CD$_3$OD) δ 8.45 (s, 1H), 8.39 (d, J=9.2 Hz, 1H), 8.03 (s, 1H), 7.75 (s, 1H), 7.62 (d, J=8.5 Hz, 1H), 7.48 (d, J=8.5 Hz, 1H), 7.40 (m, 1H), 7.31-7.24 (m, 2H), 7.15 (d, J=8.3 Hz, 1H), 7.05 (t, 1H), 5.22 (s, 2H), 4.09 (m, 1H), 3.72 (m, 2H), LCMS RT=3.59 min, [M+H]$^+$=496.

Example 28

Preparation of 2-{4-[3-Chloro-4-(3-fluoro-benzyloxy)-phenylamino]-benzo[4,5]thieno[2,3-]pyrimidin-7-yl}-1-morpholin-4-yl-ethanone

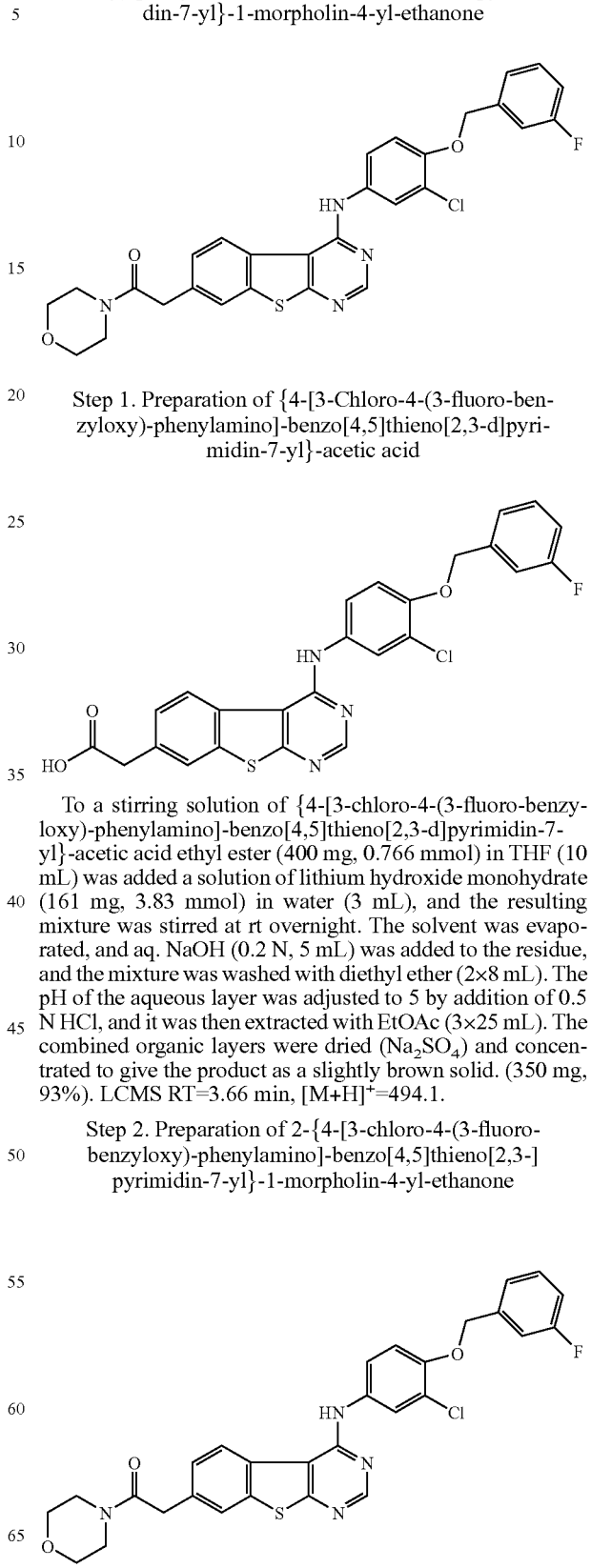

Step 1. Preparation of {4-[3-Chloro-4-(3-fluoro-benzyloxy)-phenylamino]-benzo[4,5]thieno[2,3-d]pyrimidin-7-yl}-acetic acid To a stirring solution of {4-[3-chloro-4-(3-fluoro-benzyloxy)-phenylamino]-benzo[4,5]thieno[2,3-d]pyrimidin-7-yl}-acetic acid ethyl ester (400 mg, 0.766 mmol) in THF (10 mL) was added a solution of lithium hydroxide monohydrate (161 mg, 3.83 mmol) in water (3 mL), and the resulting mixture was stirred at rt overnight. The solvent was evaporated, and aq. NaOH (0.2 N, 5 mL) was added to the residue, and the mixture was washed with diethyl ether (2×8 mL). The pH of the aqueous layer was adjusted to 5 by addition of 0.5 N HCl, and it was then extracted with EtOAc (3×25 mL). The combined organic layers were dried (Na$_2$SO$_4$) and concentrated to give the product as a slightly brown solid. (350 mg, 93%). LCMS RT=3.66 min, [M+H]$^+$=494.1.

Step 2. Preparation of 2-{4-[3-chloro-4-(3-fluoro-benzyloxy)-phenylamino]-benzo[4,5]thieno[2,3-]pyrimidin-7-yl}-1-morpholin-4-yl-ethanone To a stirring suspension of {4-[3-chloro-4-(3-fluoro-benzyloxy)-phenylamino]-benzo[4,5]thieno[2,3-d]pyrimidin-7-yl}-acetic acid (90%, 33 mg, 0.060 mmol) and 1-hydroxybenzotriazole (8.94 mg, 0.066 mmol) in dichloromethane (2 mL) were added 1-(3-dimethylaminopropyl)-3-ethylcarbodiimide hydrochloride (13.8 mg, 0.072 mmol). Morpholine (6.29 mg, 0.072 mmol) was added after 10 min, and the mixture was stirred at rt overnight. The reaction mixture was directly put onto preparative TLC (CH$_2$Cl$_2$/CH$_3$OH=6/1) to give the target compound (18 mg, 53.2%). $^1$H-NMR (DMSO-d$_6$) δ 8.97 (s, 1H), 8.51 (s, 1H), 8.48 (d, 1H), 7.93 (d, 1H), 7.74 (d, 1H), 7.53 (q, 1H), 7.46-7.42 (m, 2H), 7.28-7.32 (m, 2H), 7.23 (d, 1H), 7.16-7.18 (m, 1H), 5.26 (s, 2H), 3.91 (2H), 3.49-3.55 (m, 8H); LCMS RT=3.51 min, [M+H]$^+$=563.1.

Using the method described above and the appropriate starting materials, examples 29-33 were similarly prepared Example 34

Preparation of 4-({3-chloro-4-[(3-fluorobenzyl)oxy]phenyl}amino)[1]benzothieno[2,3-d]pyrimidin-7-ol

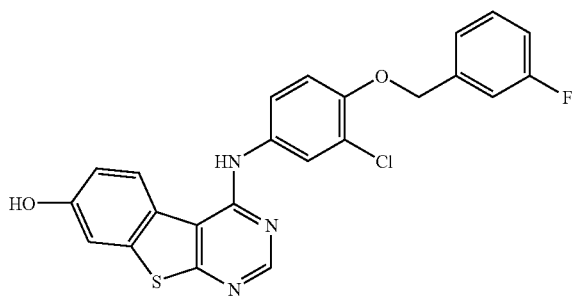

Step 1. Preparation of Ethyl 2-amino-4,7-dihydro-5H-spiro[1-benzothiophene-6,2'-[1,3]-dioxolane]-3-carboxylate

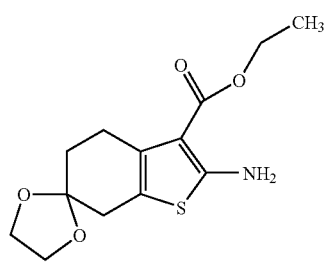

To 600 mL ethanol were sequentially 1,4-Dioxa-spiro[4.5]decan-8-one (25.0 g, 0.160 mol), ethyl cyanoacetate (18.1 g, 0.160 mol), morpholine (14.0 g, 0.160 mol), and sulfur (5.5 g, 0.160 mol). The heterogeneous contents were stirred at room temperature for 4 days, after which time all the sulfur had dissolved. The homogeneous contents were concentrated under reduced pressure, and the residue diluted with EtOAc (200 mL). The mixture was washed with water (200 mL), and the layers were separated. The organic layer was dried over MgSO$_4$, filtered, and concentrated under reduced pressure to afford the desired product as a dark colored oil (45.0 g, 99%). $^1$H-NMR (DMSO-d$_6$) δ 7.20 (s, 2H), 4.10 (q, 2H), 3.87 (s, 4H), 2.66 (t, 2H), 2.59 (s, 2H), 1.71 (t, 2H), 1.18 (t, 3H); LCMS RT=2.58 min, [M+H]$^+$=284.2.

Step 2. Preparation of 3,5,6,8-tetrahydro-4H-spiro[1-benzothieno[2,3-d]pyrimidine-7,2'-[1,3]-dioxolan]-4-one

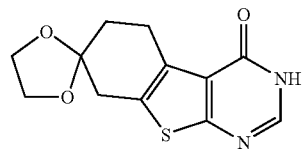

To a stirring solution of ethyl 2-amino-4,7-dihydro-5H-spiro[1-benzothiophene-6,2'-[1,3]dioxolane]-3-carboxylate (40.0 g, 0.142 mol) in formamide (225 mL) was added ammonium formate (17.8 g, 0.282 mol). The resulting mixture was stirred with at 140° C. for 16 h, after which time the heterogeneous contents were removed from heating, and allowed to cool to rt. The contents were filtered, the solid filter cake was washed with water (2×60 mL), and suction dried overnight to afford the desired product as an off-white solid (33.0 g, 88%). $^1$H-NMR (DMSO-d$_6$) δ 12.35 (broad s, 1H), 8.00 (s, 1H), 3.92 (s, 4H), 2.95 (t, 2H), 2.91 (s, 2H), 1.83 (t, 2H); LCMS RT=1.87 min, [M+H]$^+$=265.2.

Step 3. Preparation of 4-chloro-5,8-dihydro-6H-spiro[1-benzothieno[2,3-d]pyrimidine-7,2'-[1,3]dioxolane]

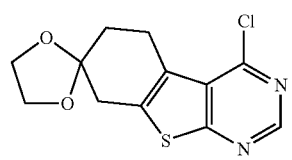

To a stirring solution of 3,5,6,8-tetrahydro-4H-spiro[1-benzothieno[2,3-d]pyrimidine-7,2'-[1,3]dioxolan]-4-one (20.0 g, 0.076 mol) in POCl$_3$ (200 mL) at 0° C. was added triethylamine (200 mL) over a 15 min. period. The resulting mixtures were allowed to warm to rt, and then heated to 80° C. After 3 h, the contents were removed from heating, and allowed to cool to rt. The heterogeneous mixture was concentrated under reduced pressure. The residue was diluted with EtOAc (100 mL), and concentrated again to further remove the volatile materials. The residue was then diluted with EtOAc (100 mL) and the heterogeneous mixture poured onto a stirring mixture of ice-water/aq NaHCO$_3$ (800 mL). After 5 min. stirring, the contents (pH 7) were filtered and the solid filter cake washed with water. The product was dried in vacuum oven overnight to afford the desired product (20.7 g, 97%) as an off-white solid. $^1$H-NMR (DMSO-d$_6$) δ 8.82 (s, 1H), 3.97 (s, 4H), 3.10 (t, 2H), 3.07 (s, 2H), 1.95 (t, 2H); LCMS RT=2.45 min, [M+H]$^+$=283.1.

Step 4. Preparation of N-(3-Chloro-4-(3-fluoro-benzyloxy)-phenylamine)-5,8-dihydro-6H-spiro[1-benzothieno[2,3-d]pyrimidine-7,2'-[1,3]dioxolan]-4-amine

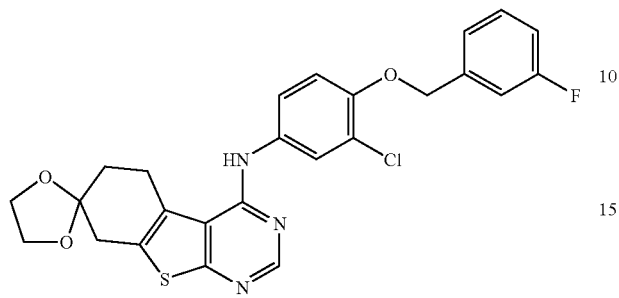

To 2-propanol (300 mL) were sequentially added 4-chloro-5,8-dihydro-6H-spiro[1-benzothieno[2,3-d]pyrimidine-7,2'-[1,3]dioxolane] (20.7 g, 73.2 mmol), 3-Chloro-4-(3-fluoro-benzyloxy)-phenylamine (18.4 g, 73.2 mmol), and HCl in dioxane (4N, 0.92 mL). The suspension was stirred with heating to 80° C., upon which the contents turn brown and homogeneous. After 15 h, the dark orange-yellow heterogeneous mixture was removed from heating, and allowed to cool to rt. The contents were filtered and the collected solid product dried under hi-vac. The filtrate was concentrated under reduced pressure and the residue suspended in $CH_3OH$ (50 mL), upon which formation of a second crop of product ensues. The second crop was collected, and from this filtrate a third crop could also be obtained. The solid product crops were combined to afford the final product (33.5 g, 92%) as an off-white solid. $^1$H-NMR (DMSO-$d_6$) δ 1.90 (t, 2H), 3.00 (s, 2H), 3.26 (t, 2H), 3.97 (s, 4H), 5.22 (s, 2H), 7.11-7.30 (m, 4H), 7.41-7.55 (m, 2H), 7.74 (s, 1H), 8.33 (s, 1H), 8.39 (s, 1H); LCMS RT=3.63 min, [M+H]$^+$=498.3.

Step 5. Preparation of N-(3-Chloro-4-(3-fluoro-benzyloxy)-phenylamine)-5,8-dihydro-6H-benzo[4,5]thieno[2,3-d]pyrimidin-7-one

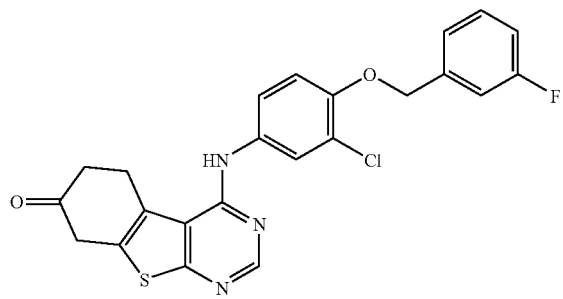

To a stirring acetic acid/$H_2O$ solution (4:1, 600 mL) was added N-(3-Chloro-4-(3-fluoro-benzyloxy)-phenylamine)-5,8-dihydro-6H-spiro[1-benzothieno[2,3-d]pyrimidine-7,2'-[1,3]dioxolan]-4-amine (34.8 g, 69.8 mmol), and the contents heated at 80° C. for 16 h. The dark colored mixture was cooled to rt, and the solvent removed under reduced pressure. The crude residue was suspended in 1N NaHCO$_3$ aq Solution (500 mL), stirred for 10 min., and filtered. The collected solid was again vigorously washed with $H_2O$ (500 mL) and filtered to afford the desired product, which was vacuum dried with heating at 40° C. for 24 h. The final product was collected (30.8 g, 97%) as an orange solid. $^1$H-NMR (DMSO-$d_6$) δ 2.66 (t, 2H), 3.44 (t, 2H), 3.74 (s, 2H), 5.23 (s, 2H), 7.14-7.32 (m, 4H), 7.40-7.52 (m, 2H), 7.75 (d, 1H), 8.34 (s, 1H), 8.39 (s, 1H); LCMS RT=3.50 min, [M+H]$^+$=454.1.

Step 6. Preparation of 4-({3-chloro-4-[(3-fluorobenzyl)oxy]phenyl}amino)[1]benzothieno[2,3-d]pyrimidin-7-ol

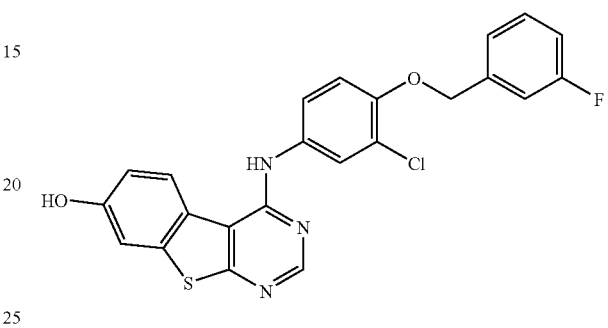

Method A

To a solution of DDQ (600.0 mg, 2.64 mmol, 1.2 equiv) in 1,4-dioxane (50 mL) was added N-(3-Chloro-4-(3-fluoro-benzyloxy)-phenylamine)-5,8-dihydro-6H-benzo[4,5]thieno[2,3-d]pyrimidin-7-one (1.0 g, 2.20 mmol, from step 5) under nitrogen. The reaction mixture was heated at 95° C. for 15 h and then cooled to rt upon which time a brown solid was precipitated. The solid was filtered and washed with 1,4-dioxane (2×30 mL). The filtrate was concentrated in vacuo. Saturated NaHCO$_3$ (50 mL) was slowly poured into the concentrated filtrate at 0° C. The mixture was stirred at 0° C. for 10 min then extracted with DCM (3×50 mL). The combined organic layers were dried over sodium sulfate and concentrated in vacuo. The crude material was purified by flash chromatography (5% methanol/DCM) to yield a brown solid (539.2 mg, 54%). $^1$H-NMR (CD$_3$OD) δ 8.49 (s, 1H), 8.33 (d, J=8.9 Hz, 1H), 7.82 (d, J=2.7 Hz, 1H), 7.57 (dd, J=2.7, 9.0 Hz, 1H), 7.48 (m, 1H), 7.44 (d, J=2.4 Hz, 1H), 7.37 (d, J=7.8 Hz, 1H), 7.32 (d, J=10 Hz, 1H), 7.23 (d, J=9 Hz, 1H), 7.12 (dd, J=2.4, 8.6 Hz, 1H), 7.14 (td, 1H), 5.29 (s, 2H), LCMS RT=3.60 min, [M+H]$^+$=452.1.

Method B

A mixture of N-(3-Chloro-4-(3-fluoro-benzyloxy)-phenylamine)-5,8-dihydro-6H-benzo[4,5]thieno[2,3-d]pyrimidin-7-one (3.5 g, 8 mmol) and tetramethylene sulfoxide (8.3 ml, 93 mmol) was heated to 100° C. for 2 hours. The reaction was judged complete by TLC (Eluent: 5% MeOH/DCM). The reaction mixture was cooled to room temperature and then diethyl ether (2×15 mL) was added to the mixture and stirred at room temperature for 10 min. The ether layer was then decanted. To the remaining oil was added acetonitrile (35 mL) followed by slow addition of water (113 mL) over a period of 5 min. The resulting suspension was stirred at room temperature for 16 hours. The product was filtered, washed with water (50 mL) and dried under vacuum at room temperature for 48 hours to give 4-({3-chloro-4-[(3-fluorobenzyl)oxy]phenyl}amino)[1]benzothieno[2,3-d]pyrimidin-7-ol. (3.30 g, 95%) as a brown solid. $^1$H-NMR (400 MHz, DMSO-$d_6$) δ 10.05 (s, 1H), 8.82 (s, 1H), 8.44 (s, 1H), 8.36 (m, 1H), 7.73 (d, J=2.5 Hz, 1H), 7.53 (dd, J=8.96, 2.73 Hz, 1H), 7.45 (2H, m), 7.30 (m, 2H), 7.18 (m, 2H), 7.04 (dd, J=8.7, 2.3 Hz, 1H), 5.25 (s, 2H); LCMS RT=3.61 min, [M+H]⁺=452.1

Using the method described above and the appropriate starting materials, example 110 was similarly prepared.

Example 35

Preparation of (2R)-3-{[4-({3-chloro-4-[(3-fluorobenzyl)oxy]phenyl}amino)[1]benzothieno[2,3-d]pyrimidin-7-yl]oxy}propane-1,2-diol

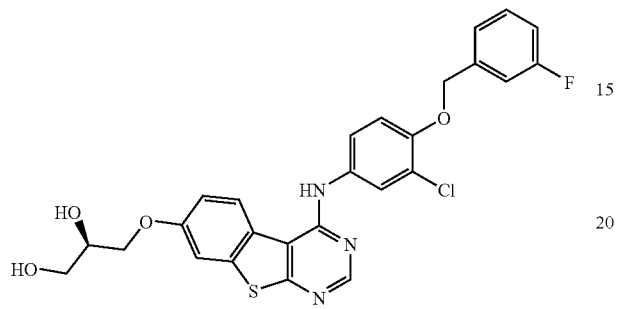

To a solution of 4-({3-chloro-4-[(3-fluorobenzyl)oxy]phenyl}amino)[1]benzothieno[2,3-d]pyrimidin-7-ol (30 mg, 0.07 mmol) in EtOH (1.0 mL) was added (R)-(+)-glycidol (5 mg, 0.07 mL, 1.0 equiv) and triethylamine (0.34 mg, 0.0035 mmol, 0.05 equiv) under nitrogen. The reaction mixture was stirred at 80° C. for 15 h and then cooled to rt. The solvents were removed in vacuo. The residue was purified by preparative HPLC to afford (2R)-3-{[4-({3-chloro-4-[(3-fluorobenzyl)oxy]phenyl}amino)[1]benzothieno[2,3-d]pyrimidin-7-yl]oxy}propane-1,2-diol as a white solid (14.8 mg, 40%). ¹H-NMR (CD₃OD) δ 8.45 (s, 1H), 8.32 (d, J=8.9 Hz, 1H), 7.73 (d, J=2.7 Hz, 1H), 7.61 (d, J=2.2 Hz, 1H), 7.46 (dd, J=2.7, 9.0 Hz, 1H), 7.40 (m, 1H), 7.30 (d, J=7.8 Hz, 1H), 7.25 (dd, J=2.3, 9.0 Hz, 2H), 7.16 (d, J=9 Hz, 1H), 7.05 (td, 1H), 5.22 (s, 2H), 4.20 (m, 1H), 4.11 (m, 1H), 4.04 (m, 1H), 3.72 (m, 2H), LCMS RT=3.32 min, [M+H]⁺=526.1.

Using the method described above and the appropriate starting materials, example 111 was similarly prepared.

Example 36

Preparation of (2S)-3-{[4-({3-chloro-4-[(3-fluorobenzyl)oxy]phenyl}amino)[1]benzothieno[2,3-d]pyrimidin-7-yl]oxy}propane-1,2-diol

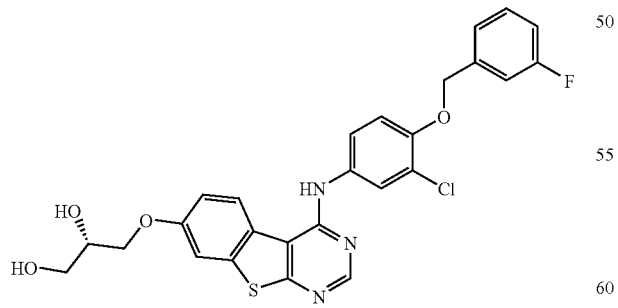

To a solution of 4-({3-chloro-4-[(3-fluorobenzyl)oxy]phenyl}amino)[1]benzothieno[2,3-d]pyrimidin-7-ol (30 mg, 0.07 mmol) in EtOH (1.0 mL) was added (S)-(−)-glycidol (5 mg, 0.07 mmol, 1.0 equiv) and triethylamine (0.34 mg, 0.0035 mmol, 0.05 equiv) under nitrogen. The reaction mixture was stirred at 80° C. for 15 h and then was cooled to rt. The solvent was removed in vacuo. The crude material was purified by preparative HPLC to give (2S)-3-{[4-({3-chloro-4-[(3-fluorobenzyl)oxy]phenyl}amino)[1]benzothieno[2,3-d]pyrimidin-7-yl]oxy}propane-1,2-diol as a white solid (14.8 mg, 40%). ¹H-NMR (CD₃OD) δ 8.45 (s, 1H), 8.32 (d, J=8.9 Hz, 1H), 7.73 (d, J=2.7 Hz, 1H), 7.61 (d, J=2.2 Hz, 1H), 7.46 (dd, J=2.7, 9.0 Hz, 1H), 7.40 (m, 1H), 7.30 (d, J=7.8 Hz, 1H), 7.25 (dd, J=2.3, 9.0 Hz, 2H), 7.16 (d, J=9 Hz, 1H), 7.05 (td, 1H), 5.22 (s, 2H), 4.20 (m, 1H), 4.11 (m, 1H), 4.04 (m, 1H), 3.72 (m, 2H), LCMS RT=3.36 min, [M+H]⁺=526.2.

Using the method described above and the appropriate starting materials, example 112 was similarly prepared.

Example 37

Preparation of 1-amino-3-{[4-({3-chloro-4-[(3-fluorobenzyl)oxy]phenyl}amino)[1]benzothieno[2,3-d]pyrimidin-7-yl]oxy}propan-2-ol

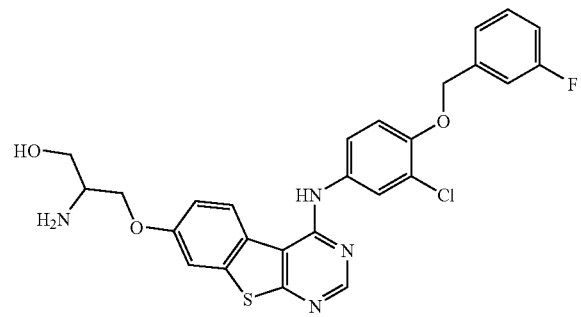

Step 1. Preparation of 2-(3-{4-[3-Chloro-4-(3-fluorobenzyloxy)-phenylamino]-benzo[4,5]thieno[2,3-d]pyrimidin-7-yloxy}-2-hydroxy-propyl)-isoindole-1,3-dione

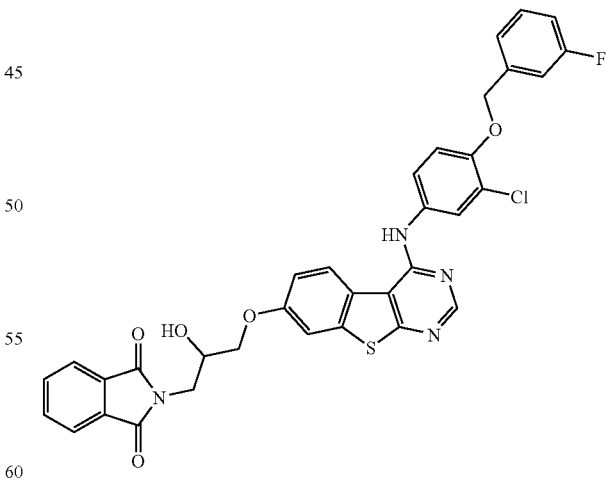

To a solution of 4-({3-chloro-4-[(3-fluorobenzyl)oxy]phenyl}amino)[1]benzothieno[2,3-d]pyrimidin-7-ol (150 mg, 0.33 mmol) in EtOH (15 mL) was added (2,3-epoxypropyl)phthalimide (101.2 mg, 0.50 mmol, 1.5 equiv) and triethylamine (1.68 mg, 0.02 mmol, 0.05 equiv) under nitrogen. The reaction mixture was stirred at 80° C. for 15 h and then cooled to rt. The resulting mixture was concentrated in vacuo. The crude material (216 mg, 0.33 mmol) was directly used in the next step without further purification, LCMS RT=3.89 min, [M+H]⁺=655.1.

Step 2: Preparation of 1-amino-3-{[4-({3-chloro-4-[(3-fluorobenzyl)oxy]phenyl}amino)[1]benzothieno[2,3-d]pyrimidin-7-yl]oxy}propan-2-ol

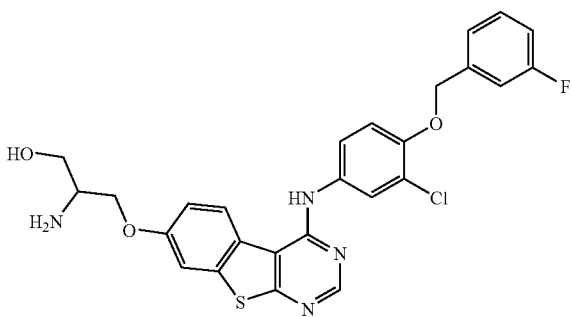

To a solution of crude material 2-(3-{4-[3-Chloro-4-(3-fluoro-benzyloxy)-phenylamino]-benzo[4,5]thieno[2,3-d]pyrimidin-7-yloxy}-2-hydroxy-propyl)-isoindole-1,3-dione (216 mg, 0.33 mmol, from Step 1) in EtOH (5 mL) was added hydrizine (1 mL) under nitrogen. The reaction was stirred at rt for 15 h. The solvent was removed in vacuo. The crude material was purified by preparative HPLC to give 1-amino-3-{[4-({3-chloro-4-[(3-fluorobenzyl)oxy]phenyl}amino)[1]benzothieno[2,3-d]pyrimidin-7-yl]oxy}propan-2-ol as a white solid (21 mg, 12%). ¹H-NMR (CD₃OD) δ 8.23 (s, 1H), 8.07 (d, J=9.2 Hz, 1H), 7.59 (d, J=2.7 Hz, 1H), 7.37 (d, J=2.4 Hz, 1H), 7.31 (dd, J=2.7, 9.0 Hz, 1H), 7.26 (m, 1H), 7.16 (d, J=7.8 Hz, 1H), 7.11 (d, J=9.7 Hz, 1H), 7.03 (dd, J=2.3, 9.0 Hz, 1H), 6.96 (d, J=9.2 Hz, 1H), 6.92 (td, 1H), 5.04 (s, 2H), 3.94 (m, 3H), 2.81 (m, 2H), LCMS RT=2.84 min, [M+H]⁺=525.1.

Example 38

Preparation of N-{3-chloro-4-[(3-fluorobenzyl)oxy]phenyl}-7-(2-morpholin-4-ylethoxy)[1]benzothieno[2,3-d]pyrimidin-4-amine

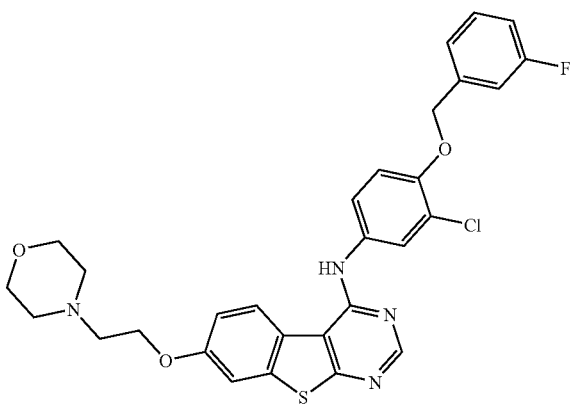

To a solution of 4-({3-chloro-4-[(3-fluorobenzyl)oxy]phenyl}amino)[1]benzothieno[2,3-d]pyrimidin-7-ol (50 mg, 0.11 mmol, from Example 34) in THF (2 mL) was added triphenylphosphine (43.5 mg, 0.17 mmol, 1.5 equiv) and 1,1'-Azobis(N,N-dimethylformamide) (28.6 mg, 0.17 mmol, 1.5 equiv) under nitrogen. The reaction mixture was stirred at rt for 5 mins and 4-(2-hydroxyethyl)morpholine (21.8 mg, 0.17 mmol, 1.5 equiv) was then. The reaction mixture was stirred at rt for 15 h and it was concentrated in vacuo. The crude material was purified by preparative HPLC to give N-{3-chloro-4-[(3-fluorobenzyl)oxy]phenyl}-7-(2-morpholin-4-ylethoxy)[1]benzothieno[2,3-d]pyrimidin-4-amine as a white solid (18.1 mg, 29%). ¹H-NMR (DMSO-d₆) δ 8.08 (broad s, NH), 7.65 (s, 1H), 7.62 (d, J=9.2 Hz, 1H), 6.91 (m, 2H), 6.74 (m, 3H), 6.63 (m, 1H), 6.48-6.37 (m, 3H), 4.42 (s, 2H), 3.38 (t, 2H), 2.75 (t, 4H), 1.90 (t, 2H), 1.65 (t, 4H), LCMS RT=2.75 min, [M+H]⁺=565.20.

Using the method described above and the appropriate starting materials, examples 39-41 were similarly prepared.

Example 42

Preparation of diethyl {[4-({3-chloro-4-[(3-fluorobenzyl)oxy]phenyl}amino)[1]benzothieno[2,3-d]pyrimidin-7-yl]oxy}malonate trifluoroacetate

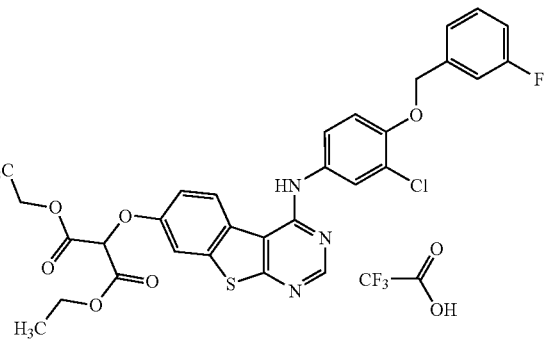

To a solution of 4-({3-chloro-4-[(3-fluorobenzyl)oxy]phenyl}amino)[1]benzothieno[2,3-d]pyrimidin-7-ol (300 mg, 0.66 mmol, from Example 34) in anhydrous DMF (10 mL) was added diethyl bromomalonate (238 mg, 1.0 mmol, 1.5 equiv) and sodium hydroxide (29.2 mg, 0.73 mmol, 1.1 equiv) under nitrogen. The reaction mixture was stirred at rt for 15 h after which time it was then poured into a flask containing a mixture of water (30 mL) and EtOAc (30 mL). The layers were separated and aqueous layer was extracted by EtOAc (2×30 mL). The combined organic layers were washed with saturated ammonium chloride (20 mL) and brine (20 mL) and dried over sodium sulfate The mixture was filtered and the filtrate was concentrated in vacuo. A portion of the crude material (10 mg) was purified by preparative HPLC and gave diethyl {[4-({3-chloro-4-[(3-fluorobenzyl)oxy]phenyl}amino)[1]benzothieno[2,3-d]pyrimidin-7-yl]oxy}malonate trifluoroacetate as a white solid (3.1 mg). The rest of crude material (100 mg, 25%) was used for example 43 without further purification. ¹H-NMR (DMSO-d₆) δ 9.06 (broad s, NH), 8.59 (d, J=9.2 Hz, 1H), 8.53 (s, 1H), 7.93 (d, J=2.7 Hz, 1H), 7.73 (d, J=2.4 Hz, 1H), 7.53 (dd, J=2.7, 8.7 Hz, 1H), 7.44 (m, 1H), 7.35 (dd, J=2.3, 9.0 Hz, 1H), 7.32 (m, 2H), 7.24 (d, J=9.0 Hz, 1H), 7.16 (td, 1H), 5.26 (s, 2H), 4.34 (q, 4H), 4.25 (s, 1H), 1.20 (t, 6H), LCMS RT=4.11 min, [M+H]⁺=610.10.

Example 43

Preparation of 2-{[4-({3-chloro-4-[(3-fluorobenzyl)oxy]phenyl}amino) [1]benzothieno[2,3-d]pyrimidin-7-yl]oxy}propane-1,3-diol trifluoroacetate (salt)

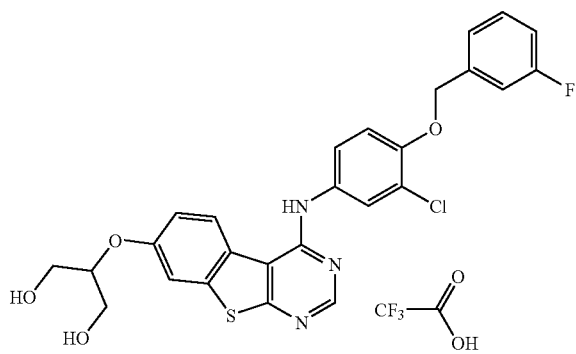

To a solution of diethyl {[4-({3-chloro-4-[(3-fluorobenzyl)oxy]phenyl}amino) [1]benzothieno[2,3-d]pyrimidin-7-yl]oxy}malonate (50 mg, 0.08 mmol) in anhydrous THF (2 mL) was added a solution of LiAlH$_4$ in THF (1M, 0.33 mL, 0.33 mmol, 4 equiv) at −78° C. under nitrogen. The reaction mixture was stirred at −78° C. for 2 h. The mixture was then warmed up to 0° C. and quenched with saturated satd ammonium chloride. The resulting white suspension was filtered through a pad of Celite® and the pad was washed with THF (1×5 mL) and EtOAc (1×5 mL). The combined filtrates were extracted with EtOAc (3×10 mL). The combined organic layers were dried over sodium sulfate and concentrated in vacuo. The crude material was purified by preparative HPLC to yield a white solid (3.1 mg, 8%). $^1$H-NMR (DMSO-d$_6$) δ 8.88 (broad s, 1H, NH), 8.46 (s, 1H), 8.42 (d, J=9.2 Hz, 1H), 7.75 (d, J=2.7 Hz, 1H), 7.73 (d, J=2.4 Hz, 1H), 7.51 (dd, J=2.7, 8.7 Hz, 1H), 7.44 (m, 1H), 7.29 (m, 2H), 7.22 (d, J=9.0 Hz, 1H), 7.20 (dd, J=2.4, 8.8 Hz, 1H), 7.16 (td, 1H), 5.24 (s, 2H), 4.42 (t, 1H), 3.63 (m, 4H), LCMS RT=3.26 min, [M+H]$^+$=526.2.

Example 44

[3-Chloro-4-(3-fluoro-benzyloxy)-phenyl]-(7-morpholin-4-yl-benzo[4,5]thieno[2,3-d]pyrimidin-4-yl)-amine

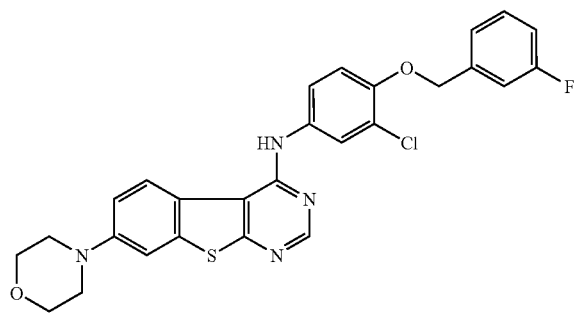

To a stirring suspension of (7-bromo-benzo[4,5]thieno[2,3-d]pyrimidin-4-yl)-[3-chloro-4-(3-fluoro-benzyloxy)-phenyl]-amine (50 mg, 0.097 mmol) in morpholine (500 mg, 5.74 mmol) was added sodium hydride (60%, 15.5 mg, 0.388 mmol). The resulting mixture was bubbled with N$_2$ for 2 min, followed by addition of 2-dicyclohexyphino-2'-(N,N-dimethylamino)biphenyl (1.91 mg, 4.86 μmol), and tris(dibenzylideneacetone)dipalladium (4.45 mg, 4.86 μmol). The mixture was further bubbled with N$_2$ for 2 min, and stirred at 135-140° C. for 20 min. It was cooled to rt, and concentrated in vacuo. The residue was purified by preparative TLC (CH$_2$Cl$_2$/CH$_3$OH=8/1) to give the target product (29.0 mg, 57%). $^1$H-NMR (DMSO-d$_6$) δ 8.83 (s, 1H), 8.43 (s, 1H), 8.37 (d, 1H), 7.73 (d, 1H), 7.61 (d, 1H), 7.51 (q, 1H), 7.43-7.48 (m, 1H), 7.28-7.32 (m, 2H), 7.21-7.25 (m, 2H), 7.16 (m, 1H), 5.25 (s, 1H), 3.78 (t, 4H), 3.26 (t, 4H). LCMS RT=3.90 min; [M+H]$^+$=521.1.

Example 45

2-{4-[3-Chloro-4-(3-fluoro-benzyloxy)-phenylamino]-benzo[4,5]thieno[2,3-d]pyrimidin-7-yl}-malonic acid diethyl ester

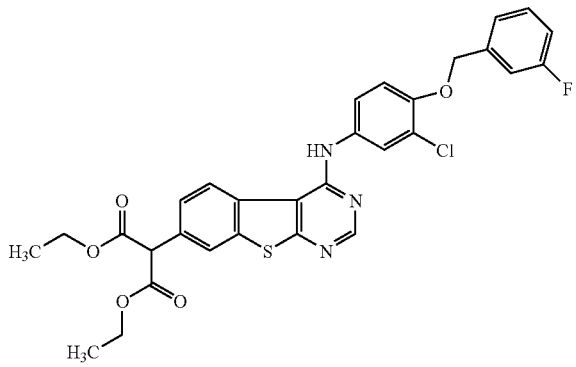

To a stirring suspension of (7-bromo-benzo[4,5]thieno[2,3-d]pyrimidin-4-yl)-[3-chloro-4-(3-fluoro-benzyloxy)-phenyl]-amine (150 mg, 0.291 mmol) in malonic acid diethyl ester (2 mL, 2 g, 12.5 mmol) was added sodium hydride (60%, 35.0 mg, 0.874 mmol). The resulting mixture was bubbled with N$_2$ for 2 min, followed by addition of biphenyl-4-yl-di-tert-butyl-phosphane (4.35 mg, 0.015 mmol), and tris(dibenzylideneacetone)dipalladium (13.3 mg, 0.015 mmol). The mixture was bubbled with N$_2$ for an additional 2 min. The reaction mixture was stirred at 135-140° C. for 20 min. It was cooled to rt, and concentrated in vacuo. The residue was purified by chromatography (hexane/EtOAc=2/1 to 1/1) to give the product (130 mg, 75%). $^1$H-NMR (CDCl$_3$-d) δ 8.56 (s, 1H), 8.05 (d, 1H), 8.00 (s, 1H), 7.82 (b, 1H), 7.74 (s, 1H), 7.66 (d, 1H), 7.49 (q, 1H), 7.34-7.39 (m, 1H), 7.20-7.26 (m, 2H), 6.99-7.05 (m, 2H), 5.18 (s, 2H), 4.80 (s, 1H), 4.20-4.31 (m, 4H), 1.28-1.34 (m, 6H); LCMS RT=4.23 min, [M+H]$^+$=594.1.

Using the method described above and the appropriate starting materials, examples 118 was similarly prepared.

Example 46

2-{4-[3-Chloro-4-(3-fluoro-benzyloxy)-phenylamino]-benzo[4,5]thieno[2,3-]pyrimidin-7-yl}-propane-1,3-diol

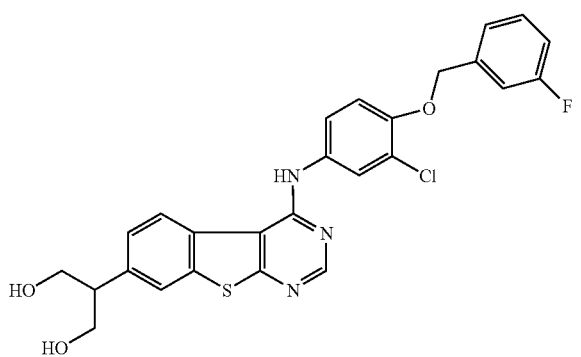

To a solution of 2-{4-[3-chloro-4-(3-fluoro-benzyloxy)-phenylamino]-benzo[4,5]thieno[2,3-d]pyrimidin-7-yl}-malonic acid dimethyl ester (prepared by the similar procedure described in example 45) (60 mg, 0.106 mmol) in dry THF (5 mL) was added lithium aluminum hydride (20.1 mg, 0.53 mmol). The resulting mixture was heated to reflux for 3 h, cooled, quenched with ice water (15 mL) and 0.2N HCl (0.5 mL). The mixture was extracted by EtOAc (3×15 mL), and the combined extracts were dried over Na$_2$SO$_4$. The solvent was evaporated, and the residue was purified by preparative TLC (CH$_2$Cl$_2$/CH$_3$OH=10/1) to give the target product (13 mg, 24%). $^1$H NMR (DMSO-d$_6$) δ 8.97 (s, 1H), 8.53 (s, 1H), 8.46 (d, 1H), 7.96 (s, 1H), 7.75 (d, 1H), 7.53 (q, 1H), 7.42-7.49 (m, 2H), 7.29-7.33 (m, 2H), 7.21 (d, 1H), 7.16-7.19 (m, 1H), 5.26 (s, 2H), 3.75-3.79 (m, 3H), 3.63-3.65 (m, 3H), 3.00 (t, 1H); LCMS RT=3.22 min, [M+H]$^+$=510.1.

Example 47

Preparation of methyl (2E)-3-[4-({3-chloro-4-[(3-fluorobenzyl)oxy]phenyl}amino)[1]benzothieno[2,3-d]pyrimidin-7-yl]acrylate

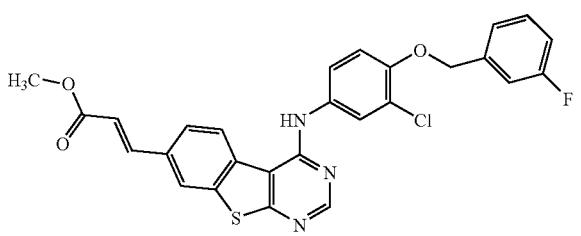

To a suspension of 7-bromo-N-{3-chloro-4-[(3-fluorobenzyl)oxy]phenyl}[1]benzothieno[2,3-d]pyrimidin-4-amine (2 g, 3.88 mmol, 1 equiv) in ethanol (80 mL) were added methyl acrylate (1 mL, 11.65 mmol, 3 equiv), triethylamine (1.6 mL, 11.65 mmol, 3 equiv), tri-o-tolylphosphine (71 mg, 0.23 mmol, 0.06 equiv) and palladium acetate (40 mg, 0.06 mmol, 0.015 equiv). The reaction mixture was heated at 100° C. in a microwave oven (Personal Chemistry) for 30 min. Upon cooling to rt, the mixture was filtered and the solid was washed with ethanol to give (2E)-3-[4-({3-chloro-4-[(3-fluorobenzyl)oxy]phenyl}amino)[1]benzothieno[2,3-d]pyrimidin-7-yl]acrylate (1.7 g, 85%) as a solid. $^1$H-NMR (DMSO-d6) δ 9.11 (s, 1H), 8.59 (d, 1H), 8.53 (s, 1H), 8.51 (d, 1H), 7.96 (dd, 1H), 7.80 (d, 1H), 7.73 (d, 1H), 7.52 (dd, 1H), 7.44 (m, 1H), 7.31 (m, 2H), 7.24 (d, 1H), 7.17 (m, 1H), 6.84 (d, 1H), 5.27 (s, 2H), 3.75 (s, 3H); LCMS RT=4.20 min, [M+H]$^+$=520.1.

Example 48

Preparation of (2E)-3-[4-({3-chloro-4-[(3-fluorobenzyl)oxy]phenyl}amino)[1]benzothieno[2,3-d]pyrimidin-7-yl]acrylic acid

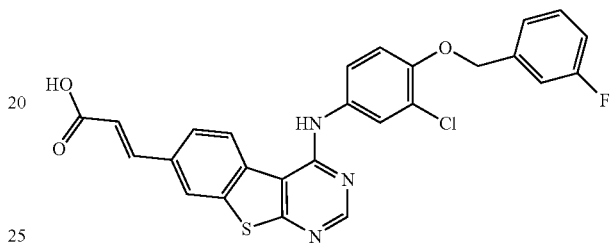

To a suspension of methyl (2E)-3-[4-({3-chloro-4-[(3-fluorobenzyl)oxy]phenyl}amino) [1]benzothieno[2,3-d]pyrimidin-7-yl]acrylate (100 mg, 0.19 mmol) in THF (3 vmL) were added ethanol (1 mL) and lithium hydroxide (2 N, 0.5 mL, 1 mmol, 5 equiv). The contents were stirred at rt for 16 h. The mixture was concentrated to dryness and the residue was triturated with ether and ethyl acetate to remove organic impurities. To the solid was added some water and 1N HCl to adjust the pH to ~6. The solid was filtered and dried to obtain (2E)-3-[4-({3-chloro-4-[(3-fluorobenzyl)oxy]phenyl}amino)[1]benzothieno[2,3-d]pyrimidin-7-yl]acrylic acid (50 mg, 51%). $^1$H-NMR (DMSO-d6) δ 9.10 (s, 1H), 8.56 (d, 1H), 8.52 (s, 1H), 8.39 (d, 1H), 7.87 (dd, 1H), 7.74 (d, 1H), 7.42-7.59 (m, 3H), 7.30 (m, 2H), 7.23 (d, 1H), 7.17 (m, 1H), 6.69 (d, 1H), 5.26 (s, 2H); LCMS RT=3.77 min, [M+H]$^+$=506.0.

Example 49

Preparation of N-{3-chloro-4-[(3-fluorobenzyl)oxy]phenyl}-7-[(1E)-3-(4-ethylpiperazin-1-yl)-3-oxoprop-1-en-1-yl][1]benzothieno[2,3-d]pyrimidin-4-amine

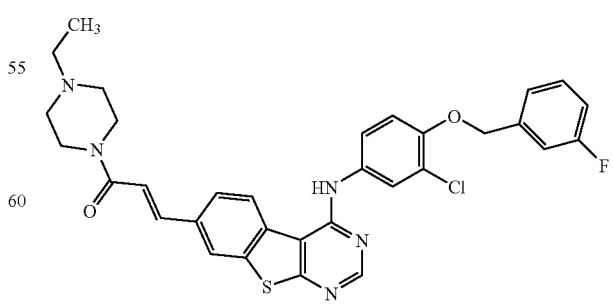

To a stirred and cold (0° C.) solution of toluene (5 mL) was added trimethyl aluminum in hexane (2M, 0.77 mL, 1.54 mmol, 4 equiv) and stirred for 10 min at 0° C. followed by addition of 1-ethyl piperazine (48 mg, 0.42 mmol, 1.1 equiv). The resulting mixture was stirred for an additional 5 min at 0° C. and then warmed to rt. A suspension of methyl (2E)-3-[4-({3-chloro-4-[(3-fluorobenzyl)oxy]phenyl}amino)[1]benzothieno[2,3-d]pyrimidin-7-yl]acrylate (200 mg) in toluene was added to the above generated mixture. The resulting mixture were heated at 100° C. for 16 h. after cooled to rt, it poured into a cold mixture (0° C.) of NH4Cl aq solution and EtOAc. The resulting gel-like mixture was filtered through a pad of Celite® and pad was washed with EtOAc. The combined EtOAc layers were dried over MgSO4 and concentrated in vacuo. The residue was carefully triturated with ether to yield a yellow solid (200 mg, 86%). $^1$H-NMR (DMSO-d6) δ 9.08 (s, 1H), 8.54 (m, 3H), 7.92 (dd, 1H), 7.74 (d, 1H), 7.62 (d, 1H), 7.52 (dd, 1H), 7.45 (m, 2H), 7.32 (m, 2H), 7.24 (d, 1H), 7.17 (m, 1H), 5.28 (s, 2H), 3.74 (m, 2H), 3.58 (m, 2H), 2.35 (m, 6H), 1.0 (t, 3H); LCMS RT=3.03 min, [M+H]$^+$=602.0.

Using the method described above and the appropriate starting materials, examples 50-55 were similarly prepared.

Example 56

Preparation of 1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol

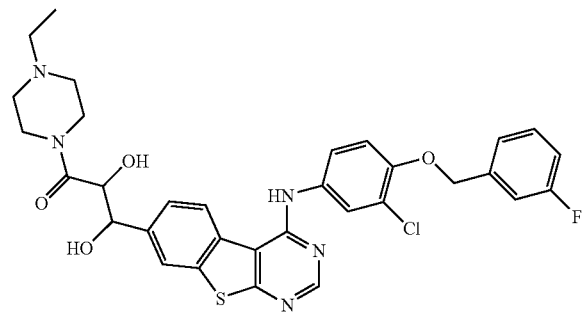

To a suspension of N-{3-chloro-4-[(3-fluorobenzyl)oxy]phenyl}-7-[(1E)-3-(4-ethylpiperazin-1-yl)-3-oxoprop-1-en-1-yl][1]benzothieno[2,3-d]pyrimidin-4-amine (150 mg, 0.25 mmol, 1 equiv) in THF (5 mL) were added osmium tetroxide (2.5 wt. % in t-BuOH, 0.03 mL, 0.01 equiv), 4-methyl-morpholine-N-oxide (58 mg, 0.5 mmol, 2 equiv) and a little water. After stirring at rt for 16 h, satd Na$_2$SO$_3$ was added and the resulting mixture was stirred for an additional 10 min. The organic contents were extracted with EtOAc, dried (MgSO$_4$) and concentrated to give the crude product (150 mg). A portion of the residue (50 mg) was purified by preparative TLC using 5% MeOH/DCM to yield (12 mg, 23%). $^1$H-NMR (DMSO-d6) δ 8.97 (s, 1H), 8.52 (s, 1H), 8.49 (d, 1H), 8.02 (d, 1H), 7.73 (d, 1H), 7.54 (m, 2H), 7.45 (m, 1H), 7.30 (m, 2H), 7.24 (d, 1H), 7.16 (m, 1H), 5.64 (d, 1H), 5.27 (s, 2H), 5.03 (d, 1H), 4.87 (t, 1H), 4.52 (m, 1H), 3.44 (m, 1H), 3.3 (m, 3H), 2.17 (m, 5H), 1.91 (m, 1H), 0.86 (t, 3H); LCMS RT=2.67 min, [M+H]$^+$=636.0.

Using the method described above and the appropriate starting materials, examples 59-60 were similarly prepared.

Example 57

Preparation of (1S,2R)-1-[4-({3-chloro-4-[(3-fluorobenzyl)oxy]phenyl}amino) [1]benzothieno[2,3-d]pyrimidin-7-yl]-3-(4-ethylpiperazin-1-yl)-3-oxopropane-1,2-diol

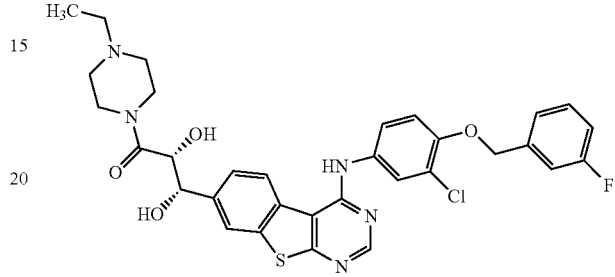

Crude 1-[4-({3-chloro-4-[(3-fluorobenzyl)oxy]phenyl}amino) [1]benzothieno[2,3-d]pyrimidin-7-yl]-3-(4-ethylpiperazin-1-yl)-3-oxopropane-1,2-diol (100 mg) from example 56 was separated by chiral HPLC column to yield 2 diastereoisomers using the following conditions: ChiralPak AD-H (20×250 mm) column, elution of 60% B at a flow rate of 15 mL/min (eluent A: 0.2% triethylamine in heptane and eluent B: isopropanol) with total run time ~30 minutes. The first fraction from HPLC (~17 min) was (1S,2R)-1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol (12.3 mg, 25%). $^1$H-NMR (DMSO-d6) δ 8.97 (s, 1H), 8.52 (s, 1H), 8.49 (d, 1H), 8.02 (d, 1H), 7.73 (d, 1H), 7.54 (m, 2H), 7.45 (m, 1H), 7.30 (m, 2H), 7.24 (d, 1H), 7.16 (m, 1H), 5.64 (d, 1H), 5.27 (s, 2H), 5.03 (d, 1H), 4.87 (t, 1H), 4.52 (m, 1H), 3.44 (m, 1H), 3.3 (m, 3H), 2.17 (m, 5H), 1.91 (m, 1H), 0.86 (t, 3H); LCMS RT=2.68 min, [M+H]$^+$=636.1.

Example 58

Preparation of (1R,2S)-1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol

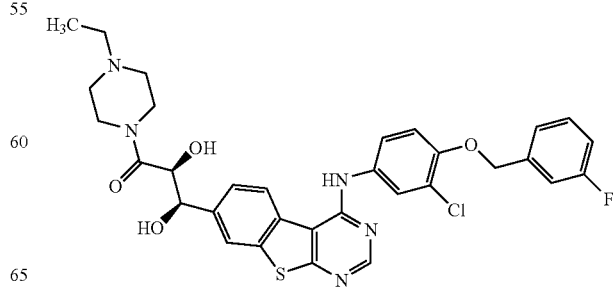

Crude 1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol (100 mg) from example 56 was separated by chiral HPLC column to yield 2 diastereoisomers using the following conditions: ChiralPak AD-H (20×250 mm) column, elution of 60% B at a flow rate of 15 mL/min (eluent A: 0.2% triethylamine in heptane and eluent B: isopropanol) with total run time ~30 minutes. The second fraction from HPLC (~23 min) was as (1R,2S)-1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol (12.1 mg, 24%). $^1$H-NMR (DMSO-d6) δ 8.97 (s, 1H), 8.52 (s, 1H), 8.49 (d, 1H), 8.02 (d, 1H), 7.73 (d, 1H), 7.54 (m, 2H), 7.45 (m, 1H), 7.30 (m, 2H), 7.24 (d, 1H), 7.16 (m, 1H), 5.64 (d, 1H), 5.27 (s, 2H), 5.03 (d, 1H), 4.87 (t, 1H), 4.52 (m, 1H), 3.44 (m, 1H), 3.3 (m, 3H), 2.17 (m, 5H), 1.91 (m, 1H), 0.86 (t, 3H); LCMS RT=2.68 min, [M+H]$^+$=636.1.

Example 61

Preparation of (2E)-3-[4-({3-chloro-4-[(3-fluorobenzyl)oxy]phenyl}amino)[1]benzothieno[2,3-d]pyrimidin-7-yl]prop-2-en-1-ol

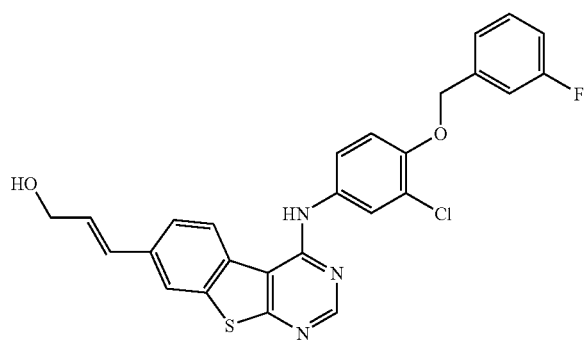

To a stirring and cold (0° C.) solution of methyl (2E)-3-[4-({3-chloro-4-[(3-fluorobenzyl)oxy]phenyl}amino)[1]benzothieno[2,3-d]pyrimidin-7-yl]acrylate (400 mg, 0.77 mmol, 1 equiv) in THF (10 mL) was added diisobutylaluminum hydride in THF (1M, 3 mL, 3 mmol, 4 equiv). The resulting mixture was stirred at rt for 20 hn and it was then poured into the aq Rochelle's salt solution and EtOAc. This was filtered a pad of Celite®. The layers were separated and the aqueous layer was extracted with EtOAc. The combined organic layers were concentrated and residue was triturated with hexane and ether to yield (250 mg, 67% yield). $^1$H-NMR (DMSO-d6) δ 8.93 (s, 1H), 8.43 (s, 1H), 8.41 (s, 1H), 8.1 (d, 1H), 7.67 (d, 1H), 7.60 (dd, 1H), 7.46 (dd, 1H), 7.39 (m, 1H), 7.24 (m, 2H), 7.17 (d, 1H), 7.10 (m, 1H), 6.49-6.65 (m, 2H), 5.20 (s, 2H), 4.90 (s, 1H), 4.11 (d, 2H); LCMS RT=3.71 min, [M+H]$^+$=492.1.

Example 62

Preparation of 1-[4-({3-chloro-4-[(3-fluorobenzyl)oxy]phenyl}amino)[1]benzothieno[2,3-d]pyrimidin-7-yl]propane-1,2,3-triol

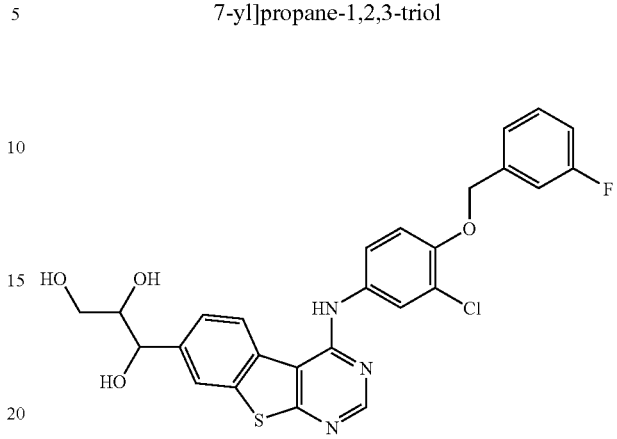

To a solution of (2E)-3-[4-({3-chloro-4-[(3-fluorobenzyl)oxy]phenyl}amino) [1]benzothieno[2,3-d]pyrimidin-7-yl] prop-2-en-1-ol (50 mg, 0.1 mmol, 1 equiv) in THF (1 mL) were added osmium tetroxide ((2.5 wt. % in t-BuOH, 6.3 μL, 0.0005 mmol, 0.005 equiv), 4-methyl-morpholine-N-oxide (24 mg, 0.2 mmol, 2 eq,) and a little water. After stirring at rt for 16 h, satd Na$_2$SO$_3$ was added and the resulting mixture was stirred for an additional 10 min. The organic contents were extracted with EtOAc, dried (MgSO$_4$) and concentrated. The crude material was purified by preparative TLC using 5% MeOH/DCM to yield 1-[4-({3-chloro-4-[(3-fluorobenzyl)oxy]phenyl}amino) [1]benzothieno[2,3-d]pyrimidin-7-yl] propane-1,2,3-triol (10 mg, 20%). $^1$H-NMR (THF-d8) δ 8.36 (s, 1H), 8.18 (d, 1H), 8.11 (s, 1H), 7.93 (d, 1H), 7.72 (d, 1H), 7.51 (dd, 1H), 7.47 (dd, 1H), 7.25 (m, 1H), 7.17 (m, 2H), 7.00 (d, 1H), 6.91 (m, 1H), 5.25 (dd, 1H), 5.09 (s, 2H), 4.70 (d, 1H), 3.70 (m, 1H), 3.51 (m, 1H), 3.46 (s, 1H), 3.39 (m, 1H), 3.23 (m, 1H); LCMS RT=3.16 min, [M+H]$^+$=526.1.

Example 63

Preparation of (1S,2S)-1-[4-({3-chloro-4-[(3-fluorobenzyl)oxy]phenyl}amino) [1]benzothieno[2,3-d]pyrimidin-7-yl]propane-1,2,3-triol

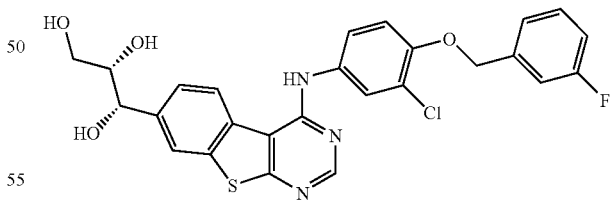

Crude 1-[4-({3-chloro-4-[(3-fluorobenzyl)oxy]phenyl}amino)[1]benzothieno[2,3-d]pyrimidin-7-yl]propane-1,2,3-triol was separated by chiral HPLC to yield 2 diastereoisomers using the following conditions: ChiralPak AD-H (4.6×250 mm) column, elution of 60% B at a flow rate of 15 mL/min [eluent A: 0.2% triethylamine in heptane and eluent B: methanol/ethanol (1:1)] with total run time ~30 min. The first fraction from HPLC (~18 min) was (1S,2S)-1-[4-({3-chloro-4-[(3-fluorobenzyl)oxy]phenyl}amino)[1]benzothieno[2,3-d]pyrimidin-7-yl]propane-1,2,3-triol (5.0 mg, 50%) ¹H-NMR (DMSO-d6) δ 8.96 (s, 1H), 8.50 (s, 1H), 8.48 (d, 1H), 8.02 (d, 1H), 7.75 (d, 1H), 7.55 (m, 2H), 7.45 (m, 1H), 7.30 (m, 2H), 7.24 (d, 1H), 7.16 (m, 1H), 5.33 (d, 1H), 5.26 (s, 2H), 4.75 (t, 1H), 4.66 (d, 1H), 4.52 (t, 1H), 3.59 (m, 1H), 3.44 (m, 1H), 3.20 (m, 1H); LCMS RT=3.14 min, [M+H]⁺=526.0.

Example 64

Preparation of (1R,2R)-1-[4-({3-chloro-4-[(3-fluorobenzyl)oxy]phenyl}amino)[1]benzothieno[2,3-d]pyrimidin-7-yl]propane-1,2,3-triol

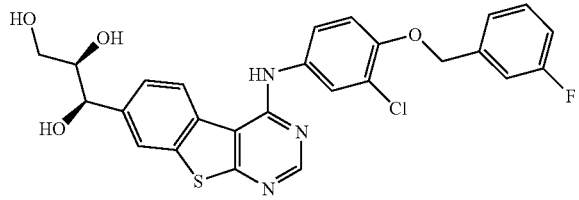

Crude 1-[4-({3-chloro-4-[(3-fluorobenzyl)oxy]phenyl}amino)[1]benzothieno[2,3-d]pyrimidin-7-yl]propane-1,2,3-triol was separated by chiral HPLC to yield 2 diastereoisomers using the following conditions: ChiralPak AD-H (4.6×250 mm) column, elution of 60% B at a flow rate of 15 μL/min [eluent A: 0.2% triethylamine in heptane and eluent B: methanol/ethanol (1:1)] with total run time ~30 min. The second fraction from HPLC (~25 min) was (1R,2R)-1-[4-({3-chloro-4-[(3-fluorobenzyl)oxy]phenyl}amino)[1]benzothieno[2,3-d]pyrimidin-7-yl]propane-1,2,3-triol (5.5 mg, 55%) ¹H-NMR (DMSO-d6) δ 8.96 (s, 1H), 8.50 (s, 1H), 8.48 (d, 1H), 8.02 (d, 1H), 7.75 (d, 1H), 7.55 (m, 2H), 7.45 (m, 1H), 7.30 (m, 2H), 7.24 (d, 1H), 7.16 (m, 1H), 5.33 (d, 1H), 5.26 (s, 2H), 4.75 (t, 1H), 4.66 (d, 1H), 4.52 (t, 1H), 3.59 (m, 1H), 3.44 (m, 1H), 3.20 (m, 1H); LCMS RT=3.14 min, [M+H]⁺=526.1.

Example 65

Preparation of 3-[4-({3-chloro-4-[(3-fluorobenzyl)oxy]phenyl}amino)[1]benzothieno[2,3-d]pyrimidin-7-yl]propanoic acid

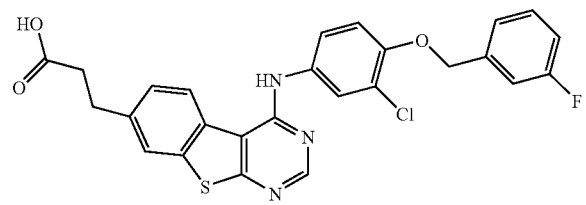

Under a blanket of N₂ 10% Pd—C (4 mg)) was added to a flask which was flushed with N₂ and the catalyst was wet with THF. A solution of (2E)-3-[4-({3-chloro-4-[(3-fluorobenzyl)oxy]phenyl}amino)[1]benzothieno[2,3-d]pyrimidin-7-yl]acrylic acid (40 mg, 0.08 mmol) in THF (2 mL) was also added to the above flask. The flask was vacuumed and H₂ was introduced into it. The reaction mixture was stirred under H₂ at rt for 16 h. The Pd—C was carefully filtered and the filtrate was concentrated to yield a white solid (30 mg, 75%). ¹H-NMR (DMSO-d₆) δ 8.95 (s, 1H), 8.50 (s, 1H), 8.45 (d, 1H), 7.96 (s, 1H), 7.74 (d, 1H), 7.52 (dd, 1H), 7.45 (m, 2H), 7.30 (m, 2H), 7.24 (d, 1H), 7.16 (m, 1H), 5.26 (s, 2H), 2.99 (t, 2H), 2.59 (t, 2H); LCMS RT=3.73 min, [M+H]⁺=508.1.

Using the method described above and the appropriate starting materials, examples 67-70 were similarly prepared.

Example 66

Preparation of N-{3-chloro-4-[(3-fluorobenzyl)oxy]phenyl}-7-[3-(4-methylpiperazin-1-yl)-3-oxopropyl][1]benzothieno[2,3-d]pyrimidin-4-amine

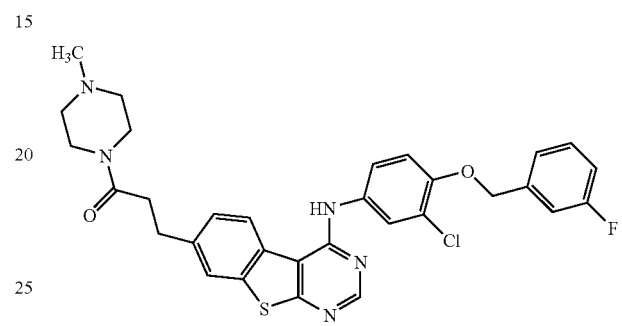

3-[4-({3-chloro-4-[(3-fluorobenzyl)oxy]phenyl}amino)[1]benzothieno[2,3-d]pyrimidin-7-yl]propanoic acid (25 mg, 0.05 mmol, 1 equiv), 4-methyl piperazine (6 mg, 0.06 mmol, 1.2 equiv), 1-[3-(dimethylaminopropyl)]-3-ethyl carbodiimide (14.1 mg, 0.07 mmol, 1.5 equiv), 4-methyl morpholine (10 mg, 0.1 mmol, 2 equiv) and 1-hydroxybenzotriazole (14 mg, 0.1 mmol, 2 equiv) were mixed in DMF and stirred at rt for 16 h. Water and EtOAc were added and extraction was preformed 3 times. Organic layers was concentrated and purified by preparative TLC using 5% MeOH/DCM to yield a solid product (18.5 mg, 64%). ¹H-NMR (DMSO-d6) δ 8.94 (s, 1H), 8.49 (s, 1H), 8.45 (d, 1H), 7.96 (d, 1H), 7.74 (d, 1H), 7.52 (dd, 1H), 7.45 (m, 2H), 7.30 (m, 2H), 7.23 (d, 1H), 7.16 (m, 1H), 5.26 (s, 2H), 3.41 (m, 4H), 2.99 (t, 2H), 2.72 (t, 2H), 2.20 (m, 4H), 2.13 (s, 3H); LCMS RT=2.87 min, [M+H]⁺=590.2

Example 71

4-{[3-chloro-4-(pyridin-2-ylmethoxy)phenyl]amino}[1]benzothieno[2,3-d]pyrimidin-7-ol

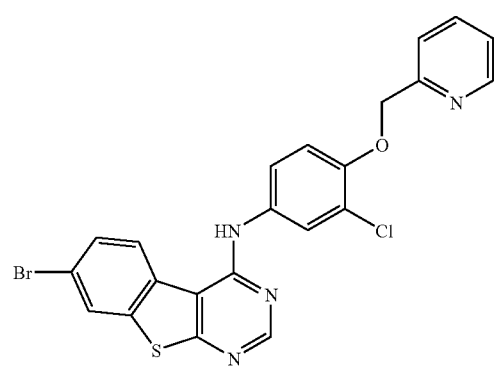

Step 1. Preparation of 3-Chloro-4-(pyridin-2-ylmethoxy)-phenylamine

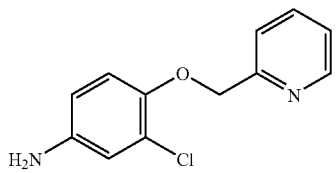

2-chloro-4-nitro phenol (10 g, 57.6 mmol, 1 equiv), 2-pycolyl chloride hydrogen chloride (9.45 g, 57.6 mmol, 1 equiv) cesium carbonate 41.3 (126.8 mmol, 2.2 equiv) and sodium iodide (8.64 g, 57.6 mmol, 1 equiv) were suspended in 200 mL acetonitrile. The reaction mixture was stirred at 60° C. for 5 h. The resulted suspension was filtered and washed with water (400 mL), yielding 2-(2-chloro-4-nitro-phenoxymethyl)-pyridine (8 g, 52%) as a red solid.

2-(2-chloro-4-nitro-phenoxymethyl)-pyridine (8 g, 30.2 mmol, 1 equiv) and iron (8.44 g, 151.1 mmol, 5 equiv) were mixed in acetic acid (100 mL) and EtOAc (50 mL) and were stirred at rt overnight. The reaction mixture was filtered through a pad of Celite®. The filtrate was concentrated in vacuo and neutralized with saturated Na$_2$CO$_3$ solution. The solution was extracted with EtOAc and the organic layer was washed with brine and concentrated in vacuo. The resulting crude material was purified by flash chromatography eluting with EtOAc/hexane (3:7) to give 3-Chloro-4-(pyridin-2-ylmethoxy)-phenylamine (3.2 g, 52%) as a white solid. $^1$H-NMR (CDCl$_3$) δ 5.18 (s, 2H), 6.50 (dd, 1H), 6.76 (d, 1H), 6.80 (d, 1H), 7.22 (m, 1H), 7.64 (d, 1H), 7.73 (td, 1H), 8.55 (m, 1H); LCMS RT=0.89 min, [M+H]$^+$=235.1.

Step 2. Preparation of 7-bromo-N-[3-chloro-4-(pyridin-2-ylmethoxy)phenyl][1]benzothieno[2,3-d]pyrimidin-4-amine

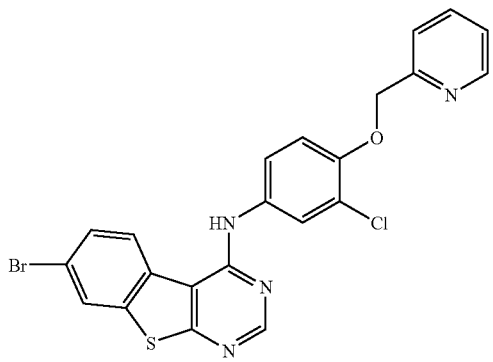

A mixture of 7-Bromo-4-chloro[1]benzothieno[2,3-d]pyrimidine (4.85 g, 16.2 mmol), 3-Chloro-4-(pyridin-2-ylmethoxy)-phenylamine (4.73 g, 18.1 mmol, 1.12 equiv), and HCl in dioxane (4.0 M, 7.25 mL) in IPA (100 mL) was heated to reflux for 3 days. The suspension was filtered and washed with IPA (3×20 mL) to collect a light tan solid. The solid was triturated with ether to give a yellow solid. The yellow solid was added to a saturated NaHCO$_3$ solution in a few portions to adjust pH to 7. The suspension was stirred at rt for 5 min then filtered and washed with water and methanol to give a yellow solid. The solid was placed under vacuum oven at 35° C. for 60 h to yield 6.48 g (76%) of product. $^1$H-NMR (CD$_3$OD) δ 8.81 (d, J=5.4 Hz, 1H), 8.59 (s, 1H), 8.45 (d, J=8.4 Hz, 1H), 8.37 (t, 1H), 8.34 (d, J=2.1 Hz, 1H), 8.04 (d, J=8.2 Hz, 1H), 7.87 (d, J=2.7 Hz, 1H), 7.81 (m, 1H), 7.80 (dd, J=2.1, 8.9 Hz, 1H), 7.63 (dd, J=2.1, 8.9 Hz, 1H), 7.31 (d, J=8.7 Hz, 1H), 5.51 (s, 2H); LCMS RT=3.43 min, [M+H]$^+$=499.0

Using the method described above and the appropriate starting materials, example 113 was similarly prepared.

Example 72

Preparation of N-[3-chloro-4-(pyridin-2-ylmethoxy) phenyl]-7-vinyl[1]benzothieno[2,3-d]pyrimidin-4-amine

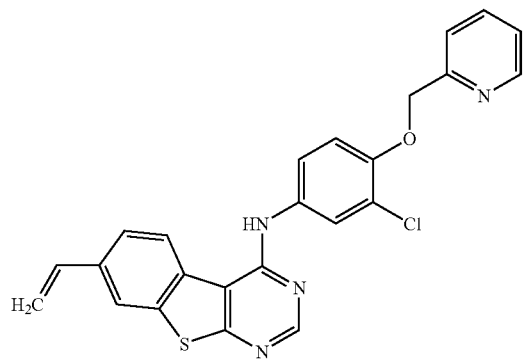

To a solution of 7-bromo-N-[3-chloro-4-(pyridin-2-ylmethoxy)phenyl][1]benzothieno[2,3-d]pyrimidin-4-amine (5.0 g, 10.0 mmol) in 1,2-dimethoxyethane (50 mL) and water (5.0 mL) were added Pd(PPh$_3$)$_4$ (580 mg, 0.50 mmol, 0.05 equiv), Potassium vinyltrifluoroorate (1.48 g, 11.1 mmol, 1.1 equiv), and sodium carbonate (2.66 g, 25.1 mmol, 2.5 equiv) under nitrogen. The reaction mixture was heated to reflux for 15 hours. The reaction mixture was cooled to rt then poured into a flask contains a mixture of water (100 mL) and EtOAc (100 mL). The resulting mixture was extracted with EtOAc (3×50 mL), dried over sodium sulfate then concentrated in vacuo. The crude material was purified by chromatography (5% EtOAc/hexane) to give an off-white solid (4.84 g, 97%). $^1$H-NMR (CD$_3$OD) δ 8.72 (d, J=5.4 Hz, 1H), 8.47 (s, 1H), 8.37 (d, J=8.4 Hz, 1H), 8.28 (t, 1H), 8.06 (s, 1H), 7.98 (d, J=7.4 Hz, 1H), 7.81 (d, J=2.7 Hz, 1H), 7.72 (m, 2H), 7.55 (dd, J=2.1, 8.9 Hz, 1H), 7.23 (d, J=8.7 Hz, 1H), 6.89 (m, 1H), 5.97 (d, J=17.6 Hz, 1H), 5.43 (s, 2H), 5.39 (d, J=10.9 Hz, 1H); LCMS RT=3.30 min, [M+H]$^+$=445.10.

Using the method described above and the appropriate starting materials, examples 114 and 130 were similarly prepared.

Example 73

Preparation of 1-(4-{[3-chloro-4-(pyridin-2-yl-methoxy)phenyl]amino}[1]benzothieno[2,3-d]pyrimidin-7-yl)ethane-1,2-diol

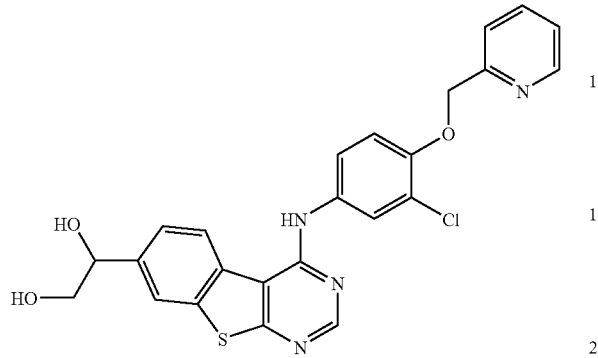

To a solution of N-[3-chloro-4-(pyridin-2-ylmethoxy)phenyl]-7-vinyl[1]benzothieno[2,3-d]pyrimidin-4-amine (4.84 g, 10.88 mmol, 1 eq, from example 72) in acetone (100 mL) and water (10 mL) were added NMO (1.53 g, 13.1 mmol, 1.2 equiv) and catalytic amount of osmium(VIII) tetroxide (2.5 w % in t-BuOH, 0.5 mL) at rt under $N_2$. The reaction mixture was stirred at rt for 15 h. Sodium sulfite (10 g) was added to the reaction mixture and stirred for 3 h. The reaction mixture was filtered through a pad of silicon gel with Celite® on top. The pad was washed with acetone (60 mL), DCM (60 mL), MeOH (60 mL), EtOAc (60 mL), and THF (60 mL). The combined organic layers were concentrated in vacuo to give an dark brown solid. The solid was further washed with DCM (30 mL) and EtOAc (30 mL) to give a yellow solid (3.47 g, 67%). $^1$H-NMR ($CD_3OD$) δ 8.57 (d, J=4.6 Hz, 1H), 8.49 (s, 1H), 8.43 (d, J=8.5 Hz, 1H), 8.06 (s, 1H), 7.92 (t, 1H), 7.81 (d, J=2.6 Hz, 1H), 7.73 (d, J=7.8 Hz, 1H), 7.65 (d, J=8.5 Hz, 1H), 7.53 (dd, J=2.6, 8.8 Hz, 1H), 7.40 (m, 1H), 7.20 (d, J=8.7 Hz, 1H), 5.31 (s, 2H), 4.88 (t, 1H), 3.73 (m, 2H); LCMS RT=2.39 min, [M+H]$^+$=479.10.

Using the method described above and the appropriate starting materials, examples 115 and 131 were similarly prepared.

Examples 74 and 75

Preparation of (1S)-1-(4-{[3-chloro-4-(pyridin-2-ylmethoxy)phenyl]amino}[1]benzothieno[2,3-d]pyrimidin-7-yl)ethane-1,2-diol and (1R)-1-(4-{[3-chloro-4-(pyridin-2-ylmethoxy)phenyl]amino}[1]benzothieno[2,3-d]pyrimidin-7-yl)ethane-1,2-diol example 74

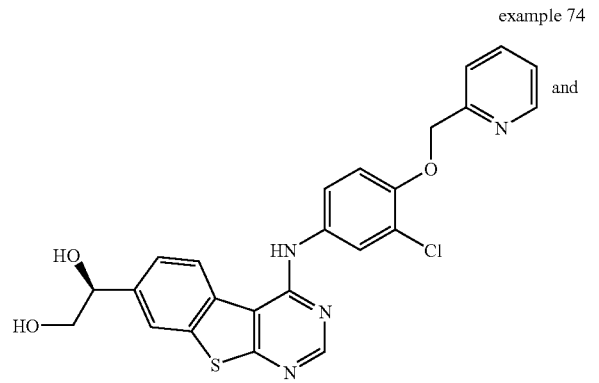

and example 75

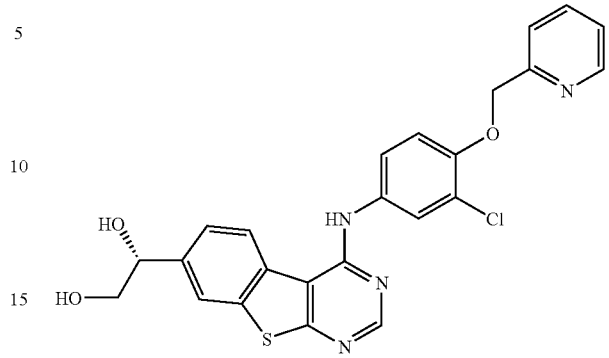

The racemic mixture of 1-(4-{[3-chloro-4-(pyridin-2-ylmethoxy)phenyl]amino}[1]benzothieno[2,3-d]pyrimidin-7-yl)ethane-1,2-diol (3.47 g, 7.25 mmol) was separated by chiral HPLC [Conditions: CHiralpak AD 5 micron 20×250 mm. Eluents: A=Hexane, B=3-1 MeOH-IPA. Gradient 50-80% B (+0.1% ET3N via make-up pump) over 20 min with Flow 15 mL/min. UV 280]. The first fraction from HPLC (~12.5 min) was (1S)-1-(4-{[3-chloro-4-(pyridin-2-ylmethoxy)phenyl]amino}[1]benzothieno[2,3-d]pyrimidin-7-yl)ethane-1,2-diol (1.35 g, 39%) as a white solid (example 74). $^1$H-NMR (DMF-$d_7$) δ 9.16 (broad s, 1H), 8.80 (m, 2H), 8.73 (s, 1H), 8.31 (s, 1H), 8.13 (d, J=2.7 Hz, 1H), 8.10 (t, 1H), 7.81-7.90 (m, 3H), 7.56 (m, 1H), 7.51 (d, J=8.9 Hz, 1H), 5.69 (d, J=4.1 Hz, 1H), 5.54 (s, 2H), 5.06 (m, 2H), 3.88 (t, 2H); LCMS RT=2.39 min, [M+H]$^+$=479.10. The second fraction from HPLC (~18 min) was (1R)-1-(4-{[3-chloro-4-(pyridin-2-ylmethoxy)phenyl]amino}[1]benzothieno[2,3-d]pyrimidin-7-yl)ethane-1,2-diol (1.27 g, 37%) as a white solid (example 75). $^1$H-NMR (DMF-$d_7$) δ 9.16 (broad s, 1H), 8.80 (m, 2H), 8.73 (s, 1H), 8.31 (s, 1H), 8.13 (d, J=2.7 Hz, 1H), 8.10 (t, 1H), 7.81-7.90 (m, 3H), 7.56 (m, 1H), 7.51 (d, J=8.9 Hz, 1H), 5.69 (d, J=4.1 Hz, 1H), 5.54 (s, 2H), 5.06 (m, 2H), 3.88 (t, 2H); LCMS RT=2.39 min, [M+H]$^+$=479.10.

Using the method described in examples 74 and 75 and the appropriate starting materials, examples 116 and 117 were similarly prepared.

Example 76

Preparation of N-[3-chloro-4-(pyridin-2-ylmethoxy)phenyl]-7-morpholin-4-yl[1]benzothieno[2,3-d]pyrimidin-4-amine trifluoroacetate

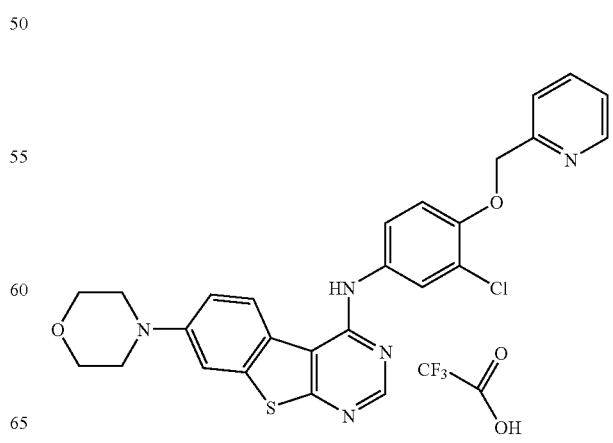

To a dry 8 mL vial contains 7-bromo-N-[3-chloro-4-(pyridin-2-ylmethoxy)phenyl][1]benzothieno[2,3-d]pyrimidin-4-amine (30 mg, 0.06 mmol, from Example 71) were sequentially added Tris(dibenzyldieneacetone)dipalladium (2.7 mg, 0.003 mmol, 0.05 equiv), 2-dicyclohexyphino-2'-(N,N-dimethylamino)biphenyl (1.2 mg, 0.003 mmol, 0.05 equiv) and NaH (4.3 mg, 0.18 mmol, 3 equiv) under nitrogen. Morpholine (0.5 mL) was added at last to the reaction vial as solvent and reagent. The reaction mixture was heated at 140° C. for 20 min before cooled to rt. The crude mixture was separated by preparative HPLC to give a white solid (6.2 mg, 16.7%). $^1$H-NMR (DMSO-$d_6$) δ 8.86 (broad s, 1H), 8.61 (d, J=4.7 Hz, 1H), 8.44 (s, 1H), 8.37 (d, J=9.0 Hz, 1H), 7.93 (t, 1H), 7.74 (d, J=2.5 Hz, 1H), 7.61 (m, 2H), 7.51 (dd, J=2.6, 8.9 Hz, 1H), 7.41 (m, 1H), 7.24 (m, 2H), 5.31 (s, 2H), 3.78 (t, 4H), 3.26 (t, 4H); LCMS RT=3.01 min, [M+H]$^+$=504.1.

Using the method described above and the appropriate starting materials, examples 77-80, 119, and 120 were similarly prepared.

Example 94

Preparation of (4-{[3-chloro-4-(pyridin-2-ylmethoxy)phenyl]amino}[1]benzothieno[2,3-d]pyrimidin-7-yl)acetic acid

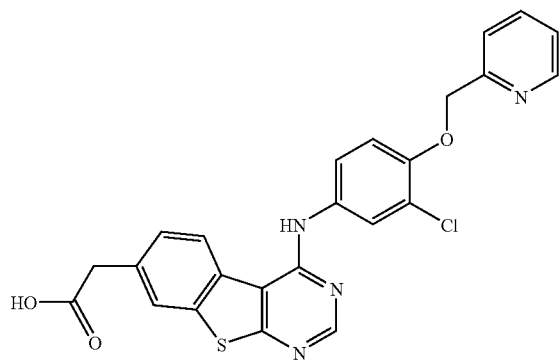

Step 1 Preparation of ethyl[4-({3-chloro-4-[(3-fluorobenzyl)oxy]phenyl}amino)[1]benzothieno[2,3-d]pyrimidin-7-yl]acetate

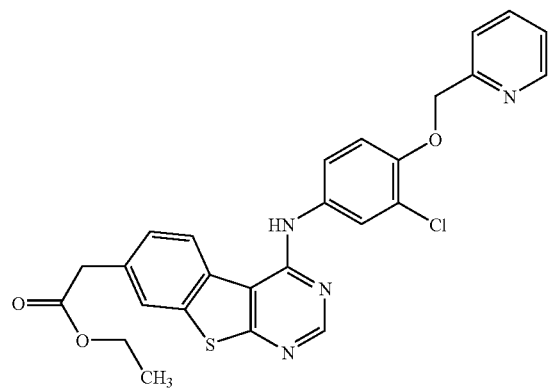

To a solution of (4-chloro-benzo[4,5]thieno[2,3-d]pyrimidin-7-yl)-acetic acid ethyl ester (500 mg, 1.63 mmol, 1 eq, from example 1 Step 7) in isopropyl alcohol (20 mL) and HCl in dioxane (4N, 0.1 mL) was added 3-Chloro-4-(pyridin-2-ylmethoxy)-phenylamine (497.3 mg, 2.12 mmol, 1.3 equiv). The reaction mixture was irradiated in a microwave reactor at 155° C. for 15 min. The mixture was allowed to cool to rt during which time yellow solid was precipitated out from the solution. The solid was filtered, washed with IPA (3×10 mL) then dried in vacuum oven at 35° C. for 15 h to a yellow solid (612 mg, 74%). $^1$H-NMR (CD$_3$OD) δ 8.66 (d, J=4.6 Hz, 1H), 8.48 (s, 1H), 8.40 (d, J=8.5 Hz, 1H), 8.15 (t, 1H), 7.96 (s, 1H), 7.89 (d, J=7.8 Hz, 1H), 7.80 (d, J=2.6 Hz, 1H), 7.61 (m, 1H), 7.54 (m, 2H), 7.22 (d, J=8.5 Hz, 1H), 5.39 (s, 2H), 4.18 (q, 2H), 3.86 (s, 2H), 1.28 (t, 3H); LCMS RT=3.25 min, [M+H]$^+$=505.2.

Step 2. Preparation of (4-{[3-chloro-4-(pyridin-2-ylmethoxy)phenyl]amino}[1]benzothieno[2,3-d]pyrimidin-7-yl)acetic acid

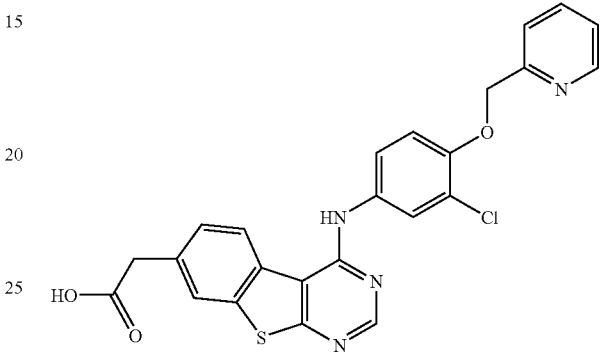

To a solution of ethyl[4-({3-chloro-4-[(3-fluorobenzyl)oxy]phenyl}amino) [1]benzothieno[2,3-d]pyrimidin-7-yl]acetate (165 mg, 0.33 mmol, 1 equiv) in THF/H$_2$O/MeOH (1:1:1, 5 mL) was added solid KOH (36.6 mg, 0.65 mmol, 2 equiv) at rt under nitrogen. The reaction mixture was stirred at rt for 15 h. The solvent was concentrated in vacuo. The crude material was purified by preparative HPLC to give a white solid (13.3 mg, 9%). $^1$H-NMR (DMSO-$d_6$) δ 9.0 (broad s, H), 8.61 (d, J=4.6 Hz, 1H), 8.51 (s, 1H), 8.49 (d, J=8.5 Hz, 1H), 7.99 (s, 1H), 7.93 (t, 1H), 7.76 (d, J=2.6 Hz, 1H), 7.62 (d, J=7.8 Hz, 1H), 7.53 (dd, J=2.6, 8.8 Hz, 1H), 7.49 (d, J=8.5 Hz, 1H), 7.40 (m, 1H), 7.24 (d, J=8.7 Hz, 1H), 5.32 (s, 2H), 3.77 (s, 2H); LCMS RT=3.08 min, [M+H]$^+$=477.2

Using the method described above and the appropriate starting materials, examples 121 and 135 were similarly prepared.

Example 95

Preparation of N-[3-chloro-4-(pyridin-2-ylmethoxy)phenyl]-7-(2-morpholin-4-yl-2-oxoethyl)[1]benzothieno[2,3-d]pyrimidin-4-amine

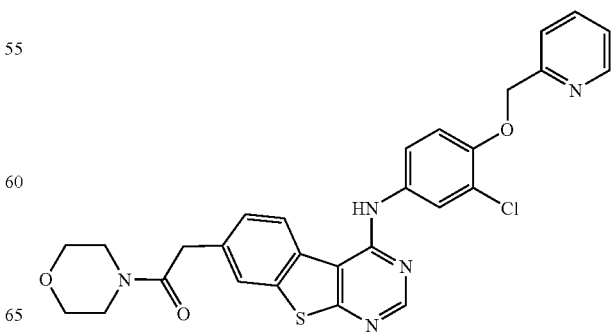

To a solution of (4-{[3-chloro-4-(pyridin-2-ylmethoxy)phenyl]amino}[1]benzothieno[2,3-d]pyrimidin-7-yl)acetic acid (50 mg, 0.10 mmol, 1 eq, from example 94) in DCM (2 mL) were added HOBt (14 mg, 0.10 mmol, 1 equiv) and EDCI (24 mg, 0.13 mmol, 1.2 equiv) under nitrogen. After the mixture was stirred at rt for 5 min, morpholine was added. The resulting reaction mixture was stirred at rt for 15 h. The solvent was concentrated in vacuo. Methanol was added to the residue and a white solid was precipitated out from the solution. The solid was filtered, washed with methanol (2×3 mL) then dried in vacuo to obtain a white solid (27.8 mg, 0.05 mmol, 51%). $^1$H-NMR (DMSO-d6) δ 9.0 (broad s, 1H), 8.58 (d, J=4.6 Hz, 1H), 8.51 (s, 1H), 8.49 (d, J=8.5 Hz, 1H), 7.94 (s, 1H), 7.87 (t, 1H), 7.76 (d, J=2.2 Hz, 1H), 7.57 (d, J=7.8 Hz, 1H), 7.53 (dd, J=2.6, 8.8 Hz, 1H), 7.45 (d, J=8.5 Hz, 1H), 7.35 (m, 1H), 7.24 (d, J=8.7 Hz, 1H), 5.30 (s, 2H), 3.91 (s, 2H), 3.50 (m, 8H); LCMS RT=2.69 min, [M+H]$^+$=546.20

Using the method described above and the appropriate starting materials, examples 96-108, 122-126, and 136-146 were similarly prepared.

Example 109

Preparation of 2-(4-{[3-chloro-4-(pyridin-2-ylmethoxy)phenyl]amino}[1]benzothieno[2,3-d]pyrimidin-7-yl)ethyl sulfamate

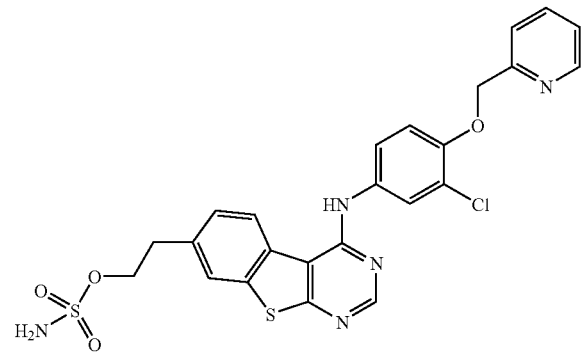

Step 1: Preparation of 2-(4-{[3-chloro-4-(pyridin-2-ylmethoxy)phenyl]amino}[1]benzothieno[2,3-d]pyrimidin-7-yl)ethanol

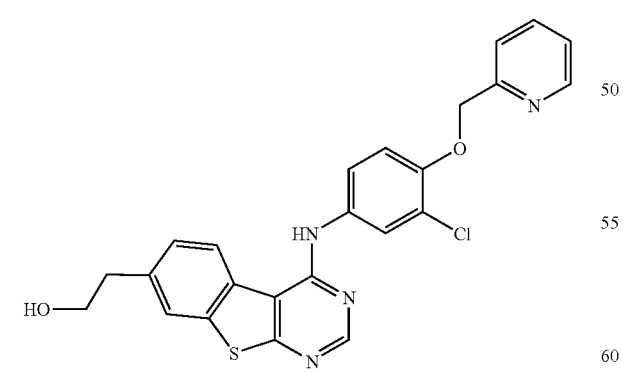

To a solution of ethyl[4-({3-chloro-4-[(3-fluorobenzyl)oxy]phenyl}amino)[1]benzothieno[2,3-d]pyrimidin-7-yl]acetate (5.45 g, 10.8 mmol, 1 equiv) in THF (200 mL) was added 1M solution of diisobutylaluminum hydride in THF (63.6 mL, 63.6 mmol, 5.8 equiv) at 0° C. under nitrogen. The reaction was slowly warm up to rt and stirred for 15 h. The solvent was removed in vacuo and the reaction mixture was cooled down to 0° C. The reaction mixture was slowly quenched with Rochelle's salt and some yellow suspension was formed. Filtered the yellow solid and washed with brine (100 mL) and water (3×100 mL), dried in the vacuum oven at 35° C. for 40 h to give a yellow solid as product (3.92 g, 75%). 1H-NMR (CD$_3$OD) δ 8.55 (d, J=4.7 Hz, 1H), 8.44 (s, 1H), 8.33 (d, J=8.5 Hz, 1H), 7.91 (t, 1H), 7.88 (s, 1H), 7.78 (d, J=2.4 Hz, 1H), 7.72 (d, J=7.7 Hz, 1H), 7.49 (m, 2H), 7.39 (m, 1H), 7.16 (d, J=9.0 Hz, 1H), 5.28 (s, 2H), 3.87 (t, 2H), 3.01 (t, 2H); LCMS RT=3.08 min, [M+H]$^+$=463.20

Step 2: Preparation of 2-(4-{[3-chloro-4-(pyridin-2-ylmethoxy)phenyl]amino}[1]benzothieno[2,3-d]pyrimidin-7-yl)ethyl sulfamate

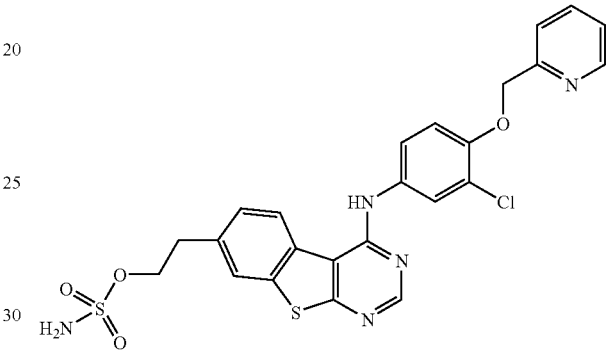

To a solution of 2-(4-{[3-chloro-4-(pyridin-2-ylmethoxy)phenyl]amino}[1]benzothieno[2,3-d]pyrimidin-7-yl)ethanol (35 mg, 0.08 mmol, 1 equiv) in N,N-Dimethylacetamide (2 mL) was added chlorosulfonamide (87 mg, 0.76 mmol, 10 equiv) under nitrogen. The reaction mixture was stirred at rt for 15 h. The solvent was concentrated in vacuo. The crude material was separated by pre-HPLC to give a white solid (18.6 mg, 43%) as product. $^1$H-NMR (DMSO-d6) δ 9.0 (broad s, 1H), 8.60 (d, J=4.6 Hz, 1H), 8.54 (s, 1H), 8.53 (d, J=8.5 Hz, 1H), 8.03 (s, 1H), 7.88 (t, 1H), 7.77 (d, J=2.2 Hz, 1H), 7.59 (d, J=7.8 Hz, 1H), 7.54 (m, 2H), 7.37 (t, 1H), 7.26 (d, J=8.7 Hz, 1H), 5.32 (s, 2H), 4.36 (t, 2H), 3.19 (t, 2H); LCMS RT=3.08 min, [M+H]$^+$=542.10

Example 147

Preparation of ((2R)-3-{[4-({3-chloro-4-[(3-fluorobenzyl)oxy]phenyl}amino)[1]benzothieno[2,3-d]pyrimidin-7-yl]oxy}propane-1,2-diol hydrochloride

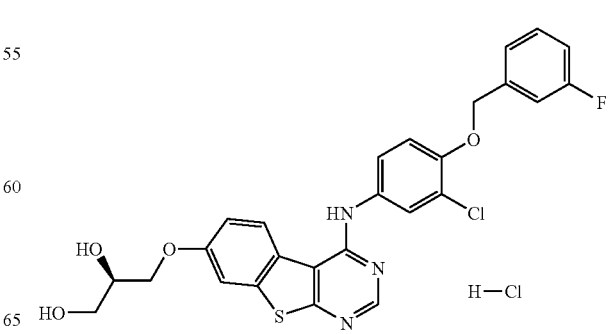

Step 1 Preparation of [3-Chloro-4-(3-fluoro-benzyloxy)-phenyl]-[7-(2,2-dimethyl-[1,3]dioxolan-4-ylmethoxy)-benzo[4,5]thieno[2,3-d]pyrimidin-4-yl]-amine

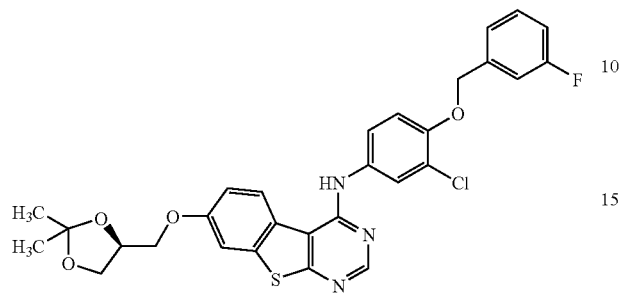

A mixture of 4-({3-chloro-4-[(3-fluorobenzyl)oxy]phenyl}amino)[1]benzothieno[2,3-d]pyrimidin-7-ol (0.11 g, 0.24 mmol), R-(−)2,2-dimethyl-1,3-dioxalan-4-ylmethyl p-toluenesulfonate (0.108 g, 0.36 mmol) and cesium carbonate (0.24 g, 1 mol) in N,N'-Dimethylformamide (1.5 mL) was heated to 80° C. The reaction was judged complete by TLC (Eluent: 2% MeOH/Dichloromethane) after 4 hours. The reaction mixture was cooled to room temperature then diluted with dichloromethane (15 mL) and extracted with water (2×15 mL). The combined organic layers were washed with water (15 mL), brine (15 mL), dried over sodium sulfate and concentrated to dryness under vacuum. The residue was subjected to silica gel chromatography using a gradient of hexanes −40% ethyl acetate/hexanes as eluent to give [3-Chloro-4-(3-fluoro-benzyloxy)-phenyl]-[7-(2,2-dimethyl-[1,3]dioxolan-4-ylmethoxy)-benzo[4,5]thieno[2,3-d]pyrimidin-4-yl]-amine (0.11 g, 80%) as a white foam. $^1$H NMR (400 MHz, DMSO-$d_6$) δ 8.92 (s, 1H), 8.47 (s, 1H), 8.45 (d, J=9.00 Hz, 1H), 7.75 (dd, J=15.85, 2.54 Hz, 2H), 7.51 (dd, J=8.90, 2.64 Hz, 1H), 7.45 (td, J=8.02, 5.87 Hz, 1H), 7.30 (m, 2H), 7.18 (m, 3H), 5.26 (s, 2H), 4.46 (qd, J=6.33, 4.50 Hz, 1H), 4.14 (m, 3H), 3.79 (dd, J=8.41, 6.26 Hz, 1H), 1.38 (s, 3H), 1.32 (s, 3H); LCMS RT=4.17 min, [M+H]$^+$=566.2

Step 2 Preparation of ((2R)-3-{[4-({3-chloro-4-[(3-fluorobenzyl)oxy]phenyl}amino)[1]benzothieno[2,3-d]pyrimidin-7-yl]oxy}propane-1,2-diol hydrochloride

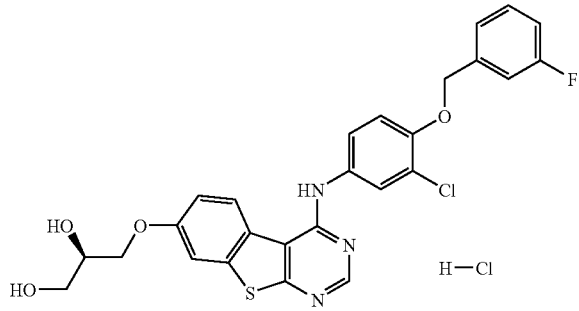

[3-Chloro-4-(3-fluoro-benzyloxy)-phenyl]-[7-(2,2-dimethyl-[1,3]dioxolan-4-ylmethoxy)benzo[4,5]thieno[2,3-d]pyrimidin-4-yl]-amine (0.92 g, 2 mmol) was dissolved in acetonitrile (5 mL) and filtered through a filter paper and filter paper washed with acetonitrile (2 mL). To the clear brown solution at 45° C. was added concentrated hydrochloric acid (37%, 0.14 mL, 2 mmol). To the resultant solid was added acetonitrile (5.0 mL) and then another equivalent of concentrated hydrochloric acid (37%, 0.14 mL, 2 mmol). The mixture was stirred at 45° C. for 1.5 hours when the reaction was judged complete by TLC (3% MeOH/Dichloromethane+one drop of triethylamine). The mixture was cooled to room temperature, filtered, and the solid was washed with acetonitrile (15 mL) and dried under vacuum at 40° C. over $P_2O_5$ for 16-18 hours to give ((2R)-3-{[4-({3-chloro-4-[(3-fluorobenzyl)oxy]phenyl}amino) [1]benzothieno[2,3-d]pyrimidin-7-yl]oxy}propane-1,2-diol hydrochloride (0.70 g, 77%).
$^1$H-NMR (400 MHz, DMSO-d6) δ 8.46 (s, 1H), 8.40 (d, J=9.0 Hz, 1H), 7.70 (m, 2H), 7.48 (dd, J=8.80, 2.54 Hz, 1H), 7.43 (dd, J=7.83, 6.06 Hz, 1H), 7.28 (m, 2H), 7.17 (m, 3H), 5.23 (s, 2H), 4.11 (dd, J=9.98, 3.91 Hz, 1H), 3.98 (dd, J=9.98, 6.26 Hz, 1H), 3.84 (dt, J=9.73, 5.80 Hz, 1H), 3.47 (d, J=5.87 Hz, 2H); LCMS RT=3.37 min, [M+H]$^+$=526.1.

Further compounds that were prepared according to the above mentioned methods are listed in the following table:

| Example | Structure | LCMS RT (min) | LCMS Ion [M + H]+ | IUPAC Name |
|---|---|---|---|---|
| 1 | 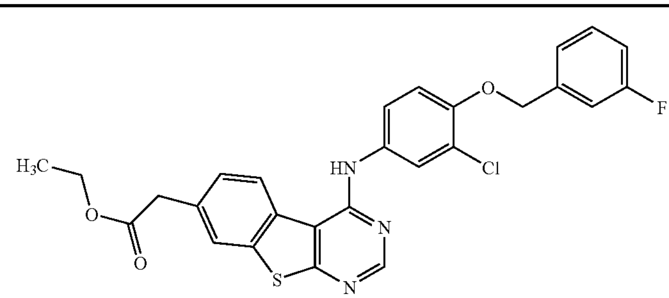 | 4.06 | 522.1 | ethyl [4-({3-chloro-4-[(3-fluorobenzyl)oxy]phenyl}amino)[1]benzothieno[2,3-d]pyrimidin-7-yl]acetate |

-continued

| Example | Structure | LCMS RT (min) | LCMS Ion [M + H]+ | IUPAC Name |
|---|---|---|---|---|
| 2 | 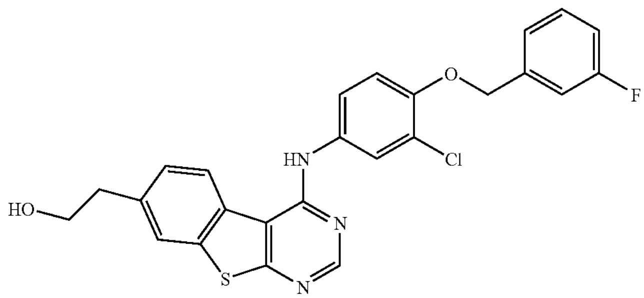 | 3.91 | 480.1 | 2-[4-({3-chloro-4-[(3-fluorobenzyl)oxy]phenyl}amino)[1]benzothieno[2,3-d]pyrimidin-7-yl]ethanol |
| 3 | 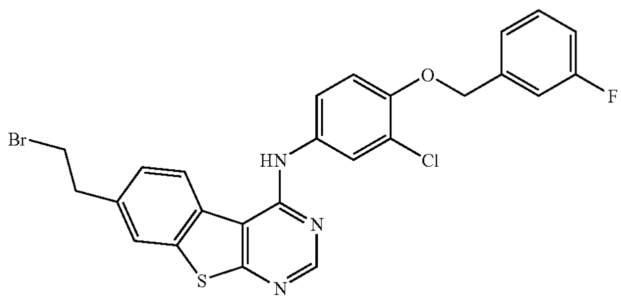 | 4.25 | 542.2/ 544.1 | 7-(2-bromoethyl)-N-{3-chloro-4-[(3-fluorobenzyl)oxy]phenyl}[1]benzothieno[2,3-d]pyrimidin-4-amine |
| 4 | 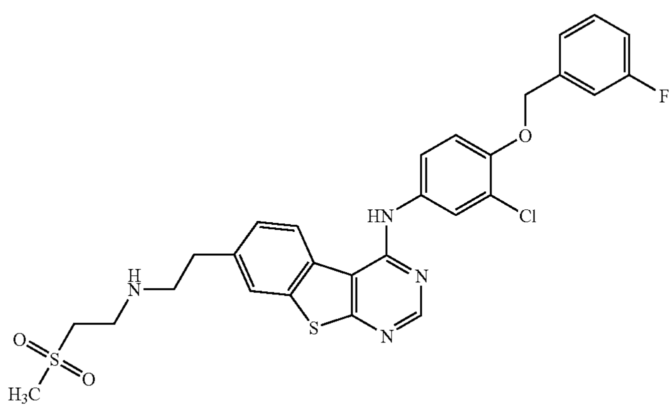 | 3.20 | 585.2 | N-{3-chloro-4-[(3-fluorobenzyl)oxy]phenyl}-7-(2-{[2-(methylsulfonyl)ethyl]amino}ethyl)[1]benzothieno[2,3-d]pyrimidin-4-amine |
| 5 | 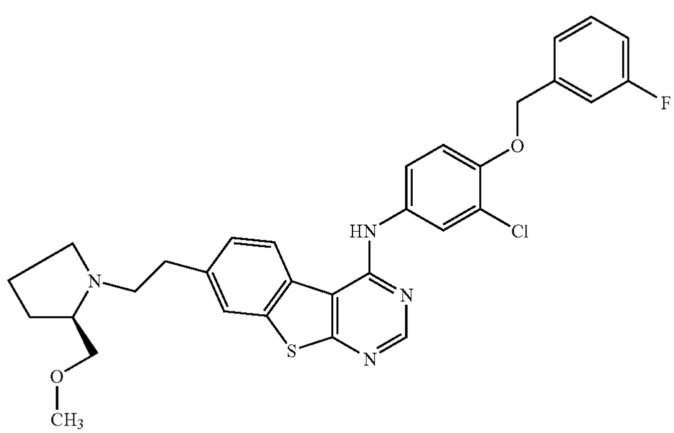 | 3.31 | 577.2 | N-{3-chloro-4-[(3-fluorobenzyl)oxy]phenyl}-7-{2-[2-(methoxymethyl)pyrrolidin-1-yl]ethyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 6 | 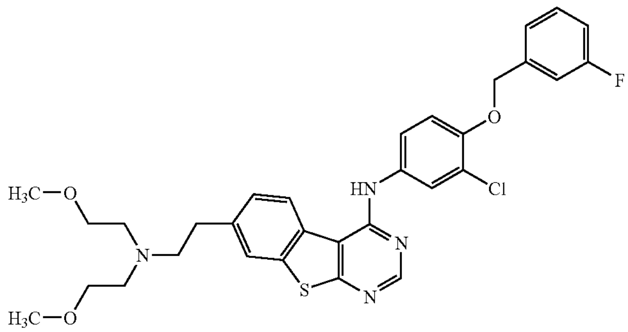 | 3.32 | 595.2 | 7-{2-[bis(2-methoxyethyl)amino]ethyl}-N-{3-chloro-4-[(3-fluorobenzyl)oxy]phenyl}[1]benzothieno[2,3-d]pyrimidin-4-amine |
| 7 | 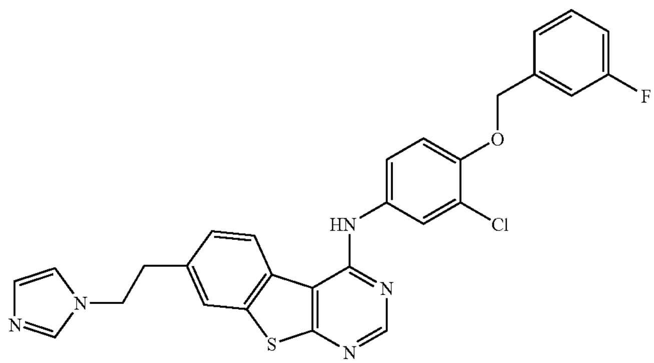 | 3.22 | 530.2 | N-{3-chloro-4-[(3-fluorobenzyl)oxy]phenyl}-7-[2-(1H-imidazol-1-yl)ethyl][1]benzothieno[2,3-d]pyrimidin-4-amine |
| 8 | 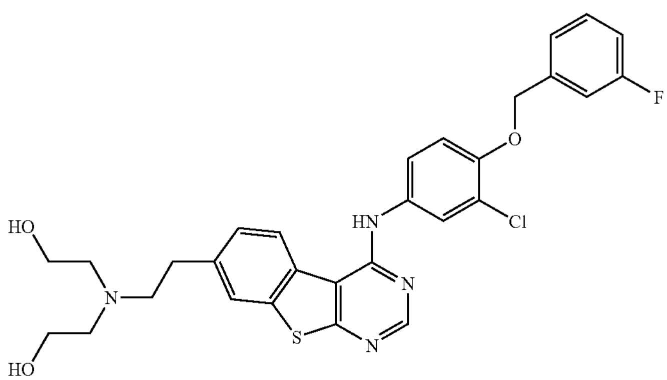 | 3.14 | 567.2 | 2,2'-({2-[4-({3-chloro-4-[(3-fluorobenzyl)oxy]phenyl}amino)[1]benzothieno[2,3-d]pyrimidin-7-yl]ethyl}imino)diethanol |
| 9 | 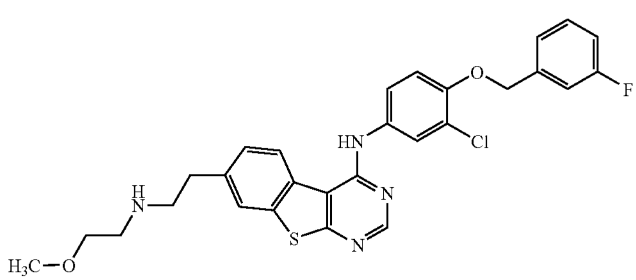 | 3.22 | 537.2 | N-{3-chloro-4-[(3-fluorobenzyl)oxy]phenyl}-7-{2-[(2-methoxyethyl)amino]ethyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 10 | 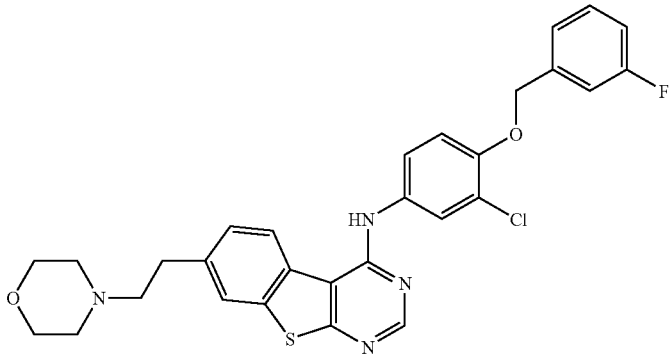 | 3.20 | 549.2 | N-{3-chloro-4-[(3-fluorobenzyl)oxy]phenyl}-7-(2-morpholin-4-ylethyl)[1]benzothieno[2,3-d]pyrimidin-4-amine |
| 11 | 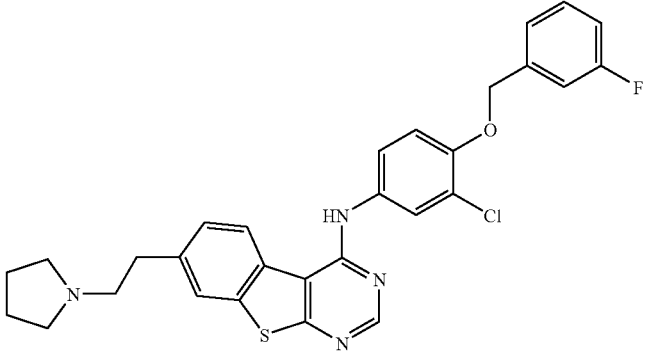 | 3.24 | 533.2 | N-{3-chloro-4-[(3-fluorobenzyl)oxy]phenyl}-7-(2-pyrrolidin-1-ylethyl)[1]benzothieno[2,3-d]pyrimidin-4-amine |
| 12 | 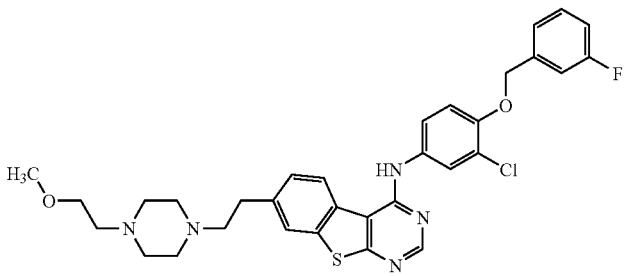 | 3.07 | 606.2 | N-{3-chloro-4-[(3-fluorobenzyl)oxy]phenyl}-7-{2-[4-(2-methoxyethyl)piperazin-1-yl]ethyl}[1]benzothieno[2,3-d]pyrimidin-4-amine |
| 13 | 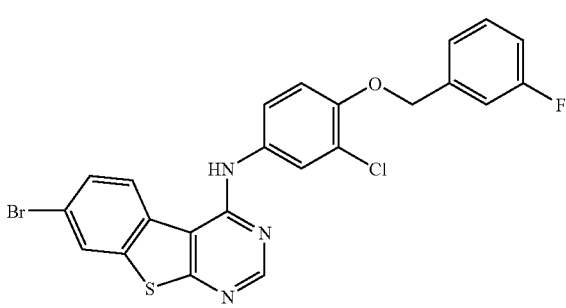 | 4.42 | 514.3 | 7-bromo-N-{3-chloro-4-[(3-fluorobenzyl)oxy]phenyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 14 | 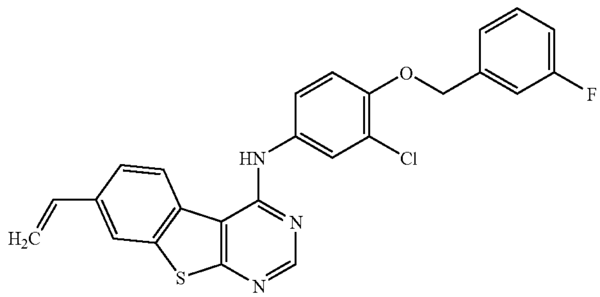 | 4.53 | 462.1 | N-{3-chloro-4-[(3-fluorobenzyl)oxy]phenyl}-7-vinyl[1]benzothieno[2,3-d]pyrimidin-4-amine |
| 15 | 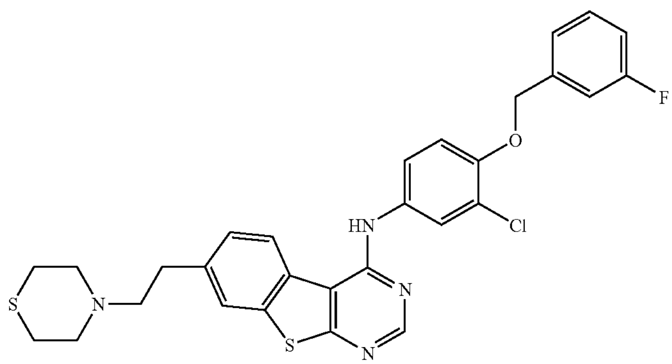 | 3.26 | 565.2 | N-{3-chloro-4-[(3-fluorobenzyl)oxy]phenyl}-7-(2-thiomorpholin-4-ylethyl)[1]benzothieno[2,3-d]pyrimidin-4-amine |
| 16 | 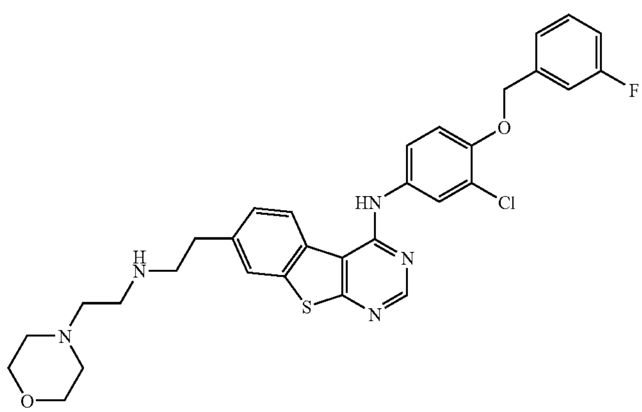 | 2.96 | 592.2 | N-{3-chloro-4-[(3-fluorobenzyl)oxy]phenyl}-7-{2-[(2-morpholin-4-ylethyl)amino]ethyl}[1]benzothieno[2,3-d]pyrimidin-4-amine |
| 17 | 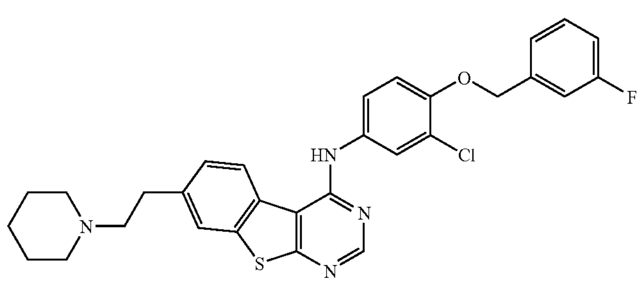 | 3.28 | 547.2 | N-{3-chloro-4-[(3-fluorobenzyl)oxy]phenyl}-7-(2-piperidin-1-ylethyl)[1]benzothieno[2,3-d]pyrimidin-4-amine |

-continued

| Example | Structure | LCMS RT (min) | LCMS Ion [M + H]+ | IUPAC Name |
|---|---|---|---|---|
| 18 | 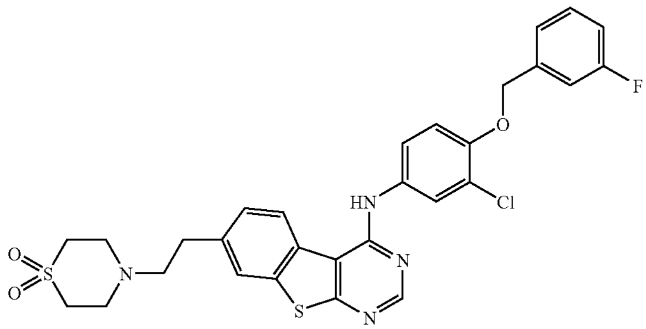 | 2.77 | 597 | N-{3-chloro-4-[(3-fluorobenzyl)oxy]phenyl}-7-[2-(1,1-dioxidothiomorpholin-4-yl)ethyl][1]benzothieno[2,3-d]pyrimidin-4-amine |
| 19 | 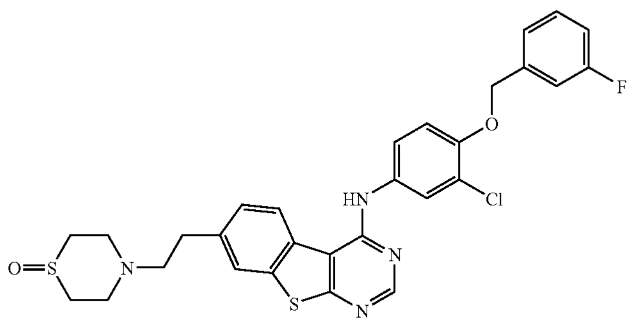 | 2.74 | 581.1 | N-{3-chloro-4-[(3-fluorobenzyl)oxy]phenyl}-7-[2-(1-oxidothiomorpholin-4-yl)ethyl][1]benzothieno[2,3-d]pyrimidin-4-amine |
| 20 | 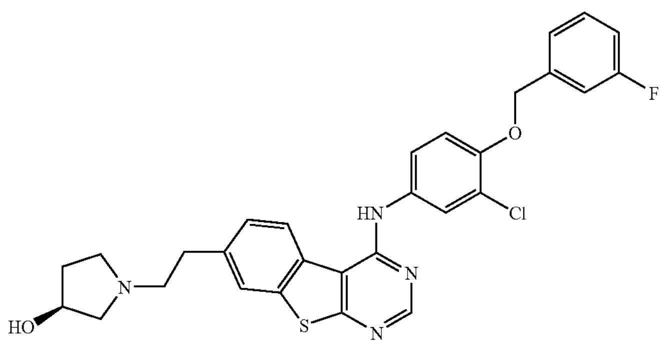 | 3.20 | 563.2 | N-{3-chloro-4-[(3-fluorobenzyl)oxy]phenyl}-7-[2-(3-methoxypyrrolidin-1-yl)ethyl][1]benzothieno[2,3-d]pyrimidin-4-amine |
| 21 | 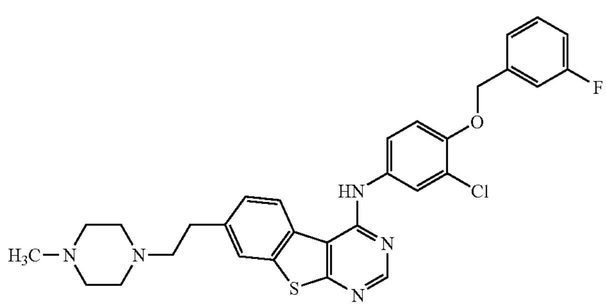 | 2.73 | 562.3 | N-{3-chloro-4-[(3-fluorobenzyl)oxy]phenyl}-7-[2-(4-methylpiperazin-1-yl)ethyl][1]benzothieno[2,3-d]pyrimidin-4-amine |

-continued

| Example | Structure | LCMS RT (min) | LCMS Ion [M + H]+ | IUPAC Name |
|---|---|---|---|---|
| 22 | 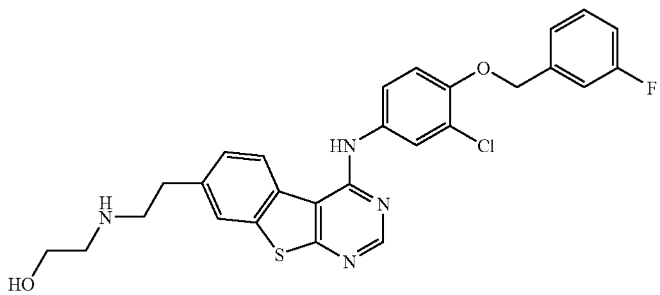 | 2.66 | 523.3 | 2-({2-[4-({3-chloro-4-[(3-fluorobenzyl)oxy]phenyl}amino)[1]benzothieno[2,3-d]pyrimidin-7-yl]ethyl}amino)ethanol |
| 23 | 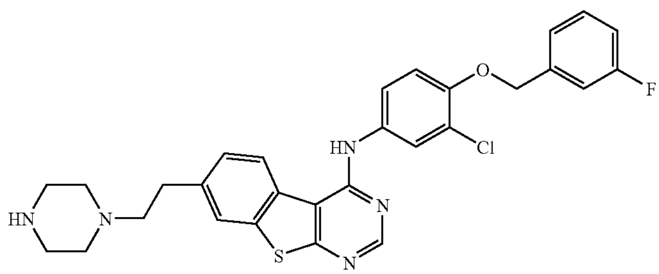 | 2.48 | 548.2 | N-{3-chloro-4-[(3-fluorobenzyl)oxy]phenyl}-7-(2-piperazin-1-ylethyl)[1]benzothieno[2,3-d]pyrimidin-4-amine |
| 24 | 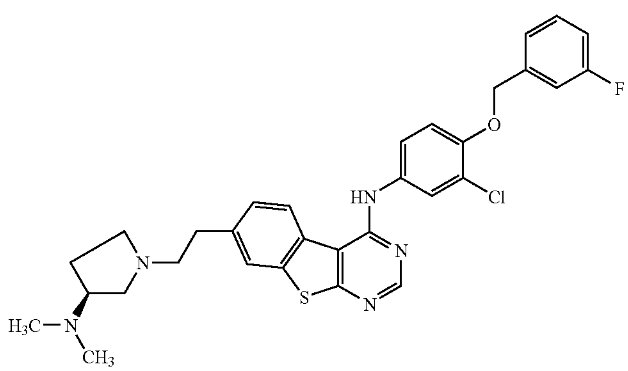 | 2.43 | 576.2 | N-{3-chloro-4-[(3-fluorobenzyl)oxy]phenyl}-7-{2-[3-(dimethylamino)pyrrolidin-1-yl]ethyl}[1]benzothieno[2,3-d]pyrimidin-4-amine |
| 25 | 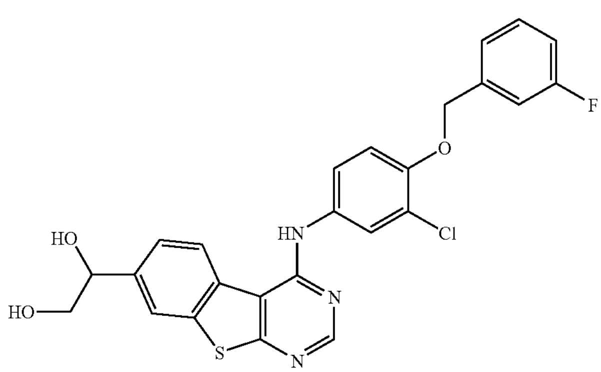 | 3.59 | 496.2 | 1-[4-({3-chloro-4-[(3-fluorobenzyl)oxy]phenyl}amino)[1]benzothieno[2,3-d]pyrimidin-7-yl]ethane-1,2-diol |

-continued

| Example | Structure | LCMS RT (min) | LCMS Ion [M + H]+ | IUPAC Name |
|---|---|---|---|---|
| 26 | 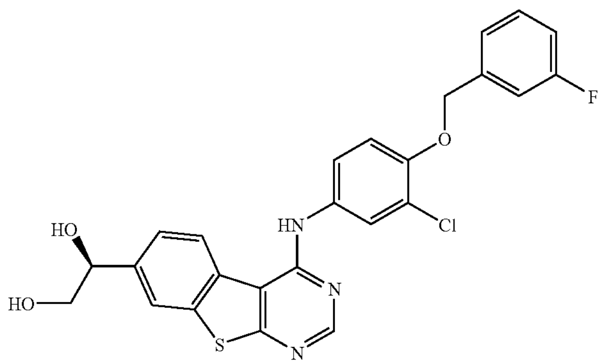 | 3.59 | 496.20 | (1S)-1-[4-({3-chloro-4-[(3-fluorobenzyl)oxy]phenyl}amino)[1]benzothieno[2,3-d]pyrimidin-7-yl]ethane-1,2-diol |
| 27 | 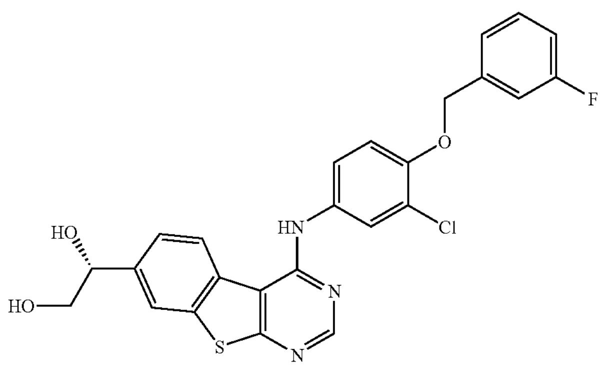 | 3.59 | 496.20 | (1R)-1-[4-({3-chloro-4-[(3-fluorobenzyl)oxy]phenyl}amino)[1]benzothieno[2,3-d]pyrimidin-7-yl]ethane-1,2-diol |
| 28 | 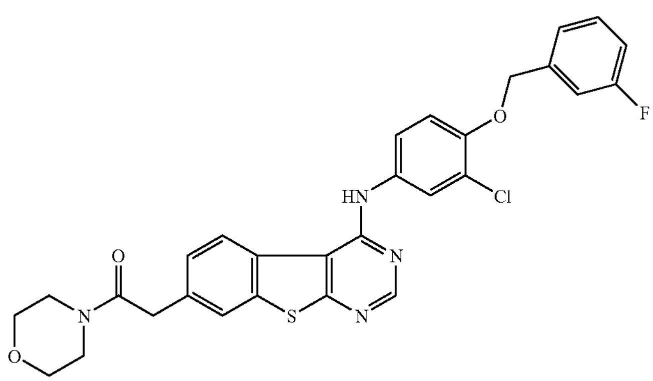 | 3.51 | 563.10 | N-{3-chloro-4-[(3-fluorobenzyl)oxy]phenyl}-7-(2-morpholin-4-yl-2-oxoethyl)[1]benzothieno[2,3-d]pyrimidin-4-amine |
| 29 | 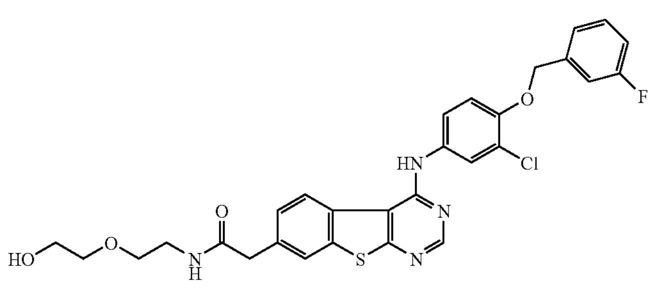 | 3.24 | 583.30 | 2-[4-({3-chloro-4-[(3-fluorobenzyl)oxy]phenyl}amino)[1]benzothieno[2,3-d]pyrimidin-7-yl]-N-[2-(2-hydroxyethoxy)ethyl]acetamide |

-continued

| Example | Structure | LCMS RT (min) | LCMS Ion [M + H]+ | IUPAC Name |
|---|---|---|---|---|
| 30 | 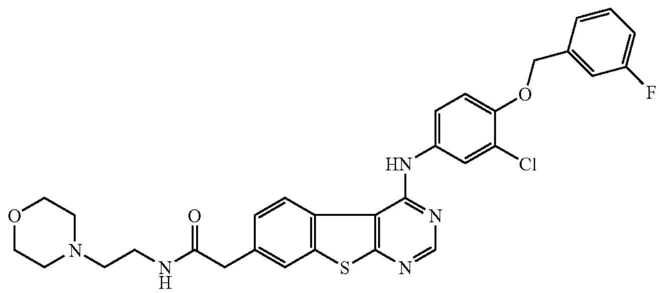 | 2.82 | 608.20 | 2-[4-({3-chloro-4-[(3-fluorobenzyl)oxy]phenyl}amino)[1]benzothieno[2,3-d]pyrimidin-7-yl]-N-(2-morpholin-4-ylethyl)acetamide |
| 31 | 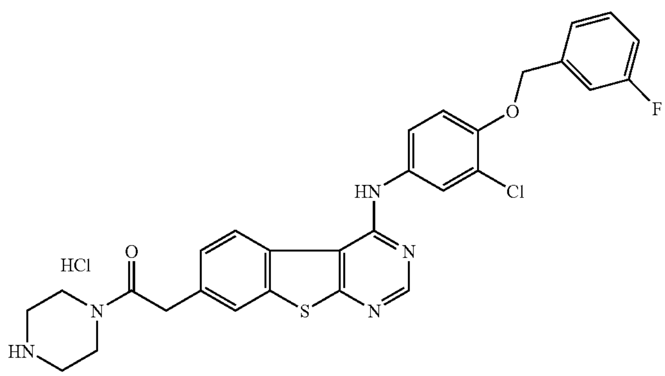 | 2.79 | 564.20 | N-{3-chloro-4-[(3-fluorobenzyl)oxy]phenyl}-7-(2-oxo-2-piperazin-1-ylethyl)[1]benzothieno[2,3-d]pyrimidin-4-amine hydrochloride |
| 32 | 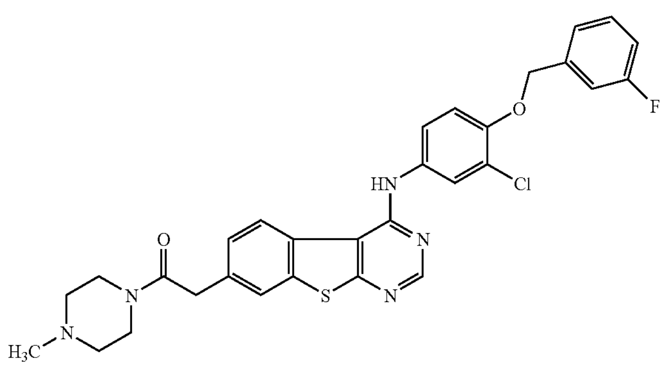 | 2.81 | 578.20 | N-{3-chloro-4-[(3-fluorobenzyl)oxy]phenyl}-7-[2-(4-methylpiperazin-1-yl)-2-oxoethyl][1]benzothieno[2,3-d]pyrimidin-4-amine |
| 33 | 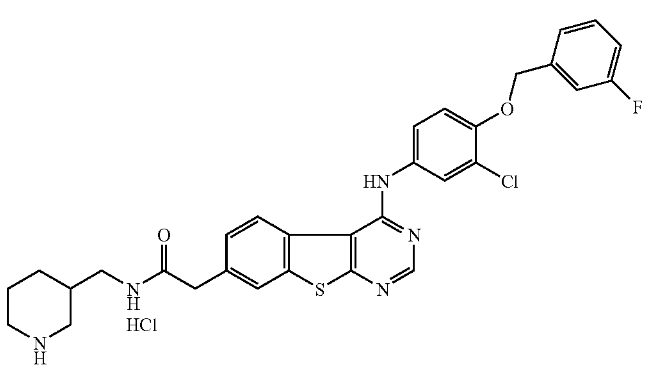 | 2.85 | 592.20 | 2-[4-({3-chloro-4-[(3-fluorobenzyl)oxy]phenyl}amino)[1]benzothieno[2,3-d]pyrimidin-7-yl]-N-(piperidin-3-ylmethyl)acetamide hydrochloride |

-continued

| Example | Structure | LCMS RT (min) | LCMS Ion [M + H]+ | IUPAC Name |
|---|---|---|---|---|
| 34 | 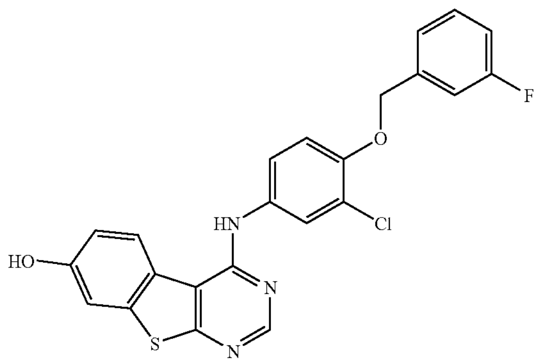 | 3.60 | 452.10 | 4-({3-chloro-4-[(3-fluorobenzyl)oxy]phenyl}amino)[1]benzothieno[2,3-d]pyrimidin-7-ol |
| 35 | 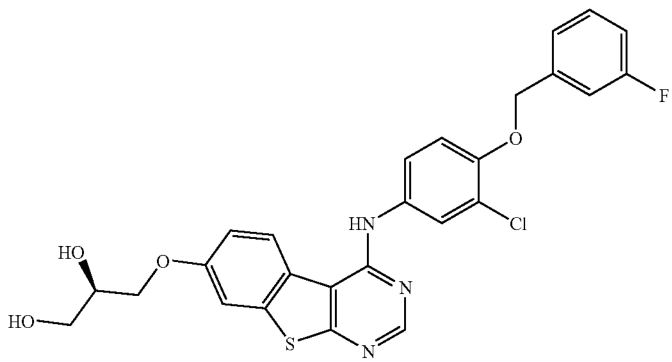 | 3.32 | 526.10 | (2R)-3-{[4-({3-chloro-4-[(3-fluorobenzyl)oxy]phenyl}amino)[1]benzothieno[2,3-d]pyrimidin-7-yl]oxy}propane-1,2-diol |
| 36 | 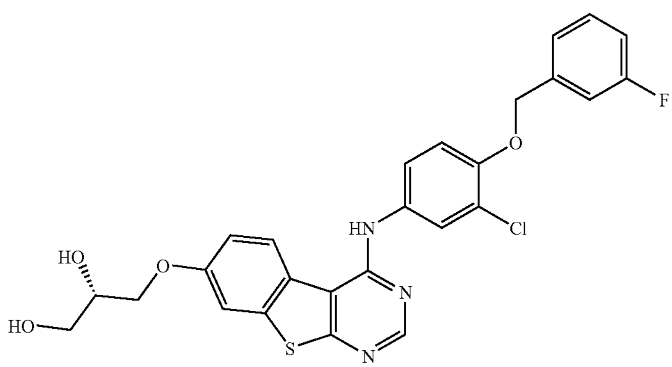 | 3.36 | 526.20 | (2S)-3-{[4-({3-chloro-4-[(3-fluorobenzyl)oxy]phenyl}amino)[1]benzothieno[2,3-d]pyrimidin-7-yl]oxy}propane-1,2-diol |
| 37 | 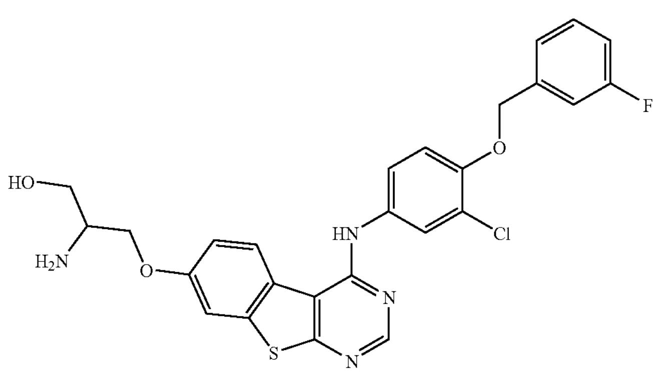 | 2.84 | 525.10 | 1-amino-3-{[4-({3-chloro-4-[(3-fluorobenzyl)oxy]phenyl}amino)[1]benzothieno[2,3-d]pyrimidin-7-yl]oxy}propan-2-ol |

-continued

| Example | Structure | LCMS RT (min) | LCMS Ion [M + H]+ | IUPAC Name |
|---|---|---|---|---|
| 38 | 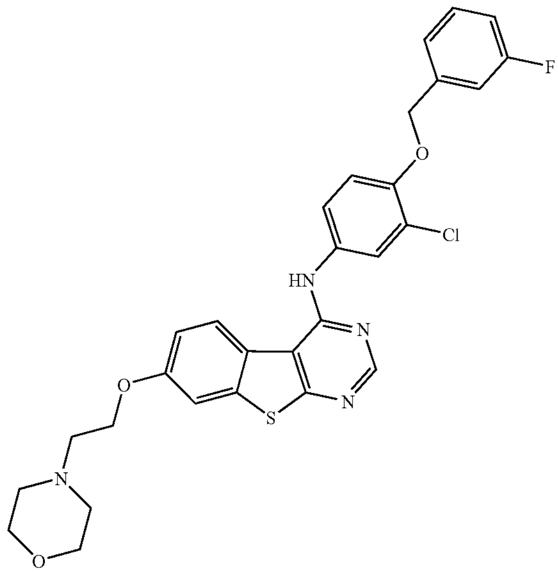 | 2.75 | 565.20 | N-{3-chloro-4-[(3-fluorobenzyl)oxy]phenyl}-7-(2-morpholin-4-ylethoxy)[1]benzothieno[2,3-d]pyrimidin-4-amine |
| 39 | 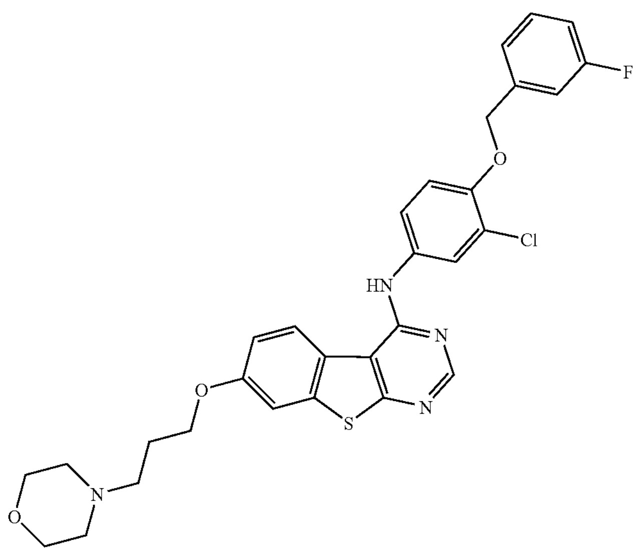 | 2.84 | 579.10 | N-{3-chloro-4-[(3-fluorobenzyl)oxy]phenyl}-7-(3-morpholin-4-ylpropoxy)[1]benzothieno[2,3-d]pyrimidin-4-amine |

-continued

| Example | Structure | LCMS RT (min) | LCMS Ion [M+H]+ | IUPAC Name |
|---|---|---|---|---|
| 40 | 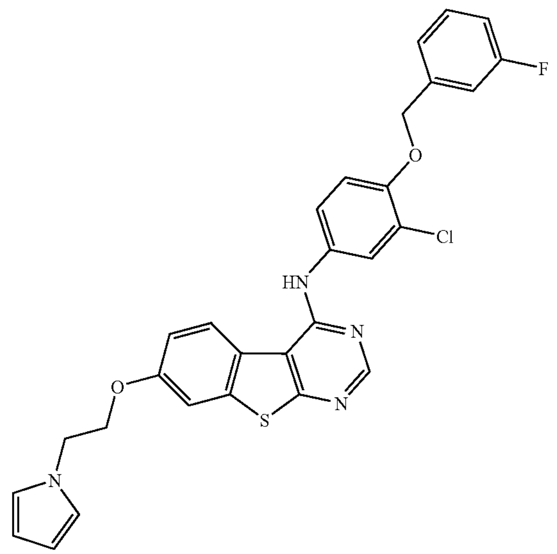 | 4.21 | 545.10 | N-{3-chloro-4-[(3-fluorobenzyl)oxy]phenyl}-7-[2-(1H-pyrrol-1-yl)ethoxy][1]benzothieno[2,3-d]pyrimidin-4-amine |
| 41 | 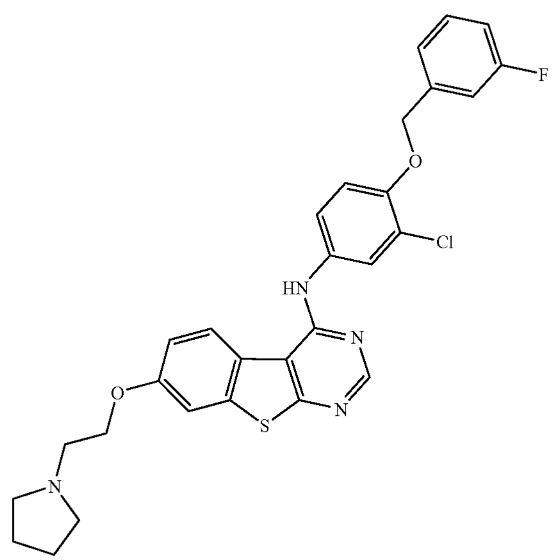 | 2.85 | 549.20 | N-{3-chloro-4-[(3-fluorobenzyl)oxy]phenyl}-7-(2-pyrrolidin-1-ylethoxy)[1]benzothieno[2,3-d]pyrimidin-4-amine |
| 42 | 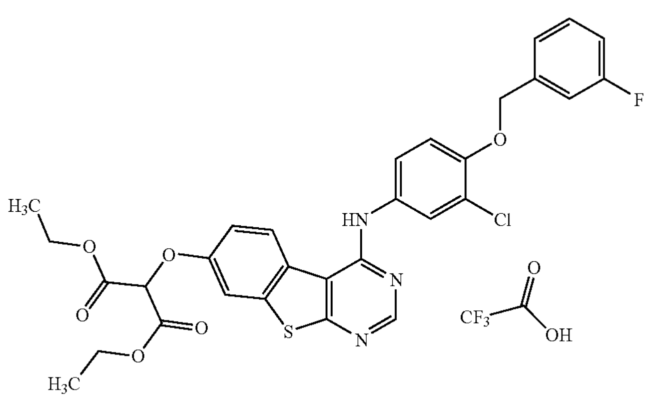 | 4.11 | 610.10 | diethyl{[4-({3-chloro-4-[(3-fluorobenzyl)oxy]phenyl}amino)[1]benzothieno[2,3-d]pyrimidin-7-yl]oxy}malonate trifluoroacetate |

-continued

| Example | Structure | LCMS RT (min) | LCMS Ion [M + H]+ | IUPAC Name |
|---|---|---|---|---|
| 43 | 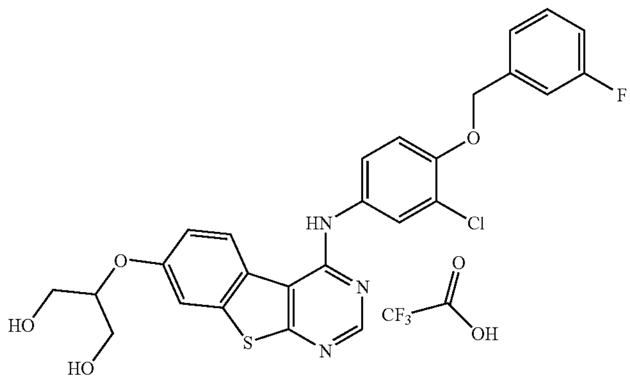 | 3.26 | 526.20 | 2-{[4-({3-chloro-4-[(3-fluorobenzyl)oxy]phenyl}amino)[1]benzothieno[2,3-d]pyrimidin-7-yl]oxy}propane-1,2-diol trifluoroacetate |
| 44 | 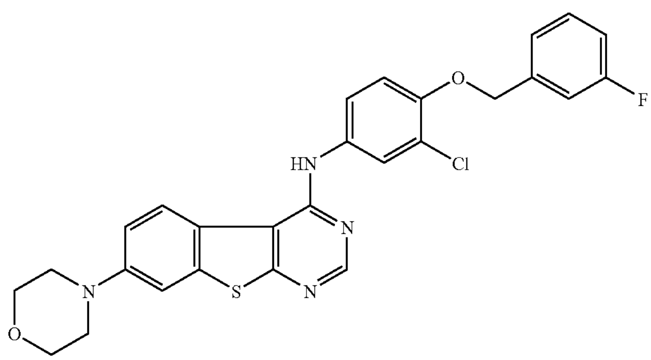 | 3.96 | 521.10 | N-{3-chloro-4-[(3-fluorobenzyl)oxy]phenyl}-7-morpholin-4-yl[1]benzothieno[2,3-d]pyrimidin-4-amine |
| 45 | 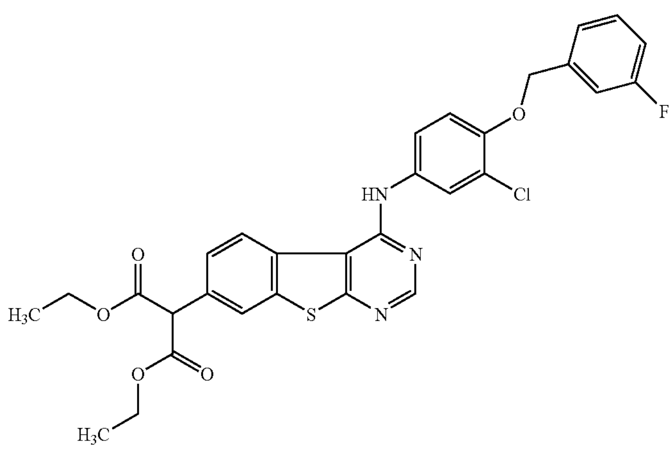 | 4.23 | 594.10 | diethyl{[4-({3-chloro-4-[(3-fluorobenzyl)oxy]phenyl}amino)[1]benzothieno[2,3-d]pyrimidin-7-yl]malonate |

-continued

| Example | Structure | LCMS RT (min) | LCMS Ion [M + H]+ | IUPAC Name |
| --- | --- | --- | --- | --- |
| 46 | 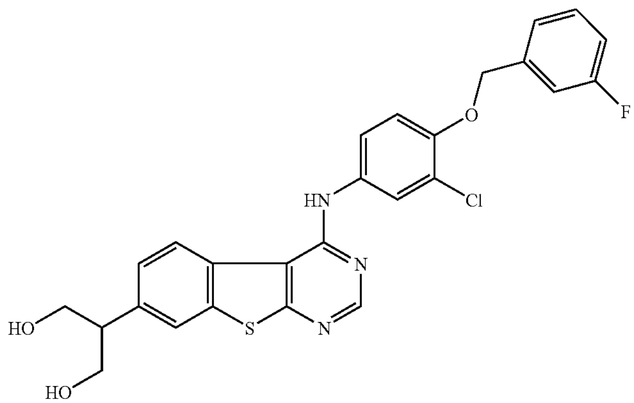 | 3.29 | 510.10 | 2-[4-({3-chloro-4-[(3-fluorobenzyl)oxy]phenyl}amino)[1]benzothieno[2,3-d]pyrimidin-7-yl]propane-1,3-diol |
| 47 | 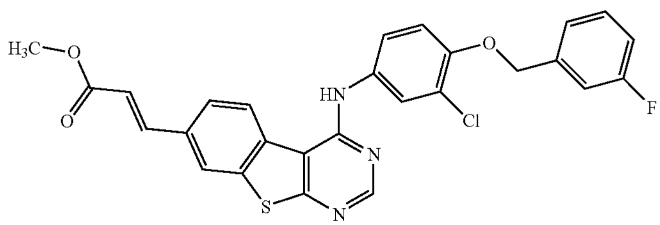 | 4.20 | 520.10 | methyl (2E)-3-[4-({3-chloro-4-[(3-fluorobenzyl)oxy]phenyl}amino)[1]benzothieno[2,3-d]pyrimidin-7-yl]acrylate |
| 48 | 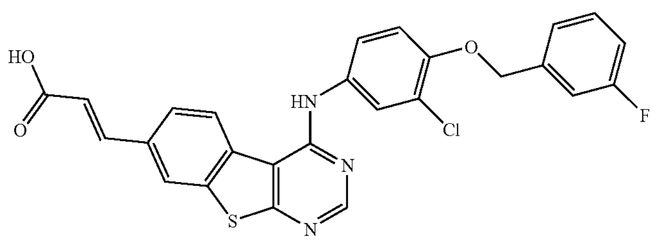 | 3.77 | 506.00 | (2E)-3-[4-({3-chloro-4-[(3-fluorobenzyl)oxy]phenyl}amino)[1]benzothieno[2,3-d]pyrimidin-7-yl]acrylic acid |
| 49 | 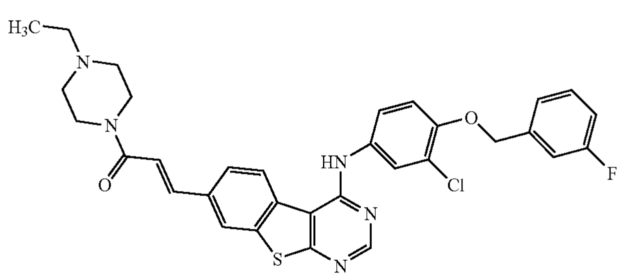 | 3.03 | 602.00 | N-{3-chloro-4-[(3-fluorobenzyl)oxy]phenyl}-7-[(1E)-3-(4-ethylpiperazin-1-yl)-3-oxoprop-1-en-1-yl][1]benzothieno[2,3-d]pyrimidin-4-amine |
| 50 | 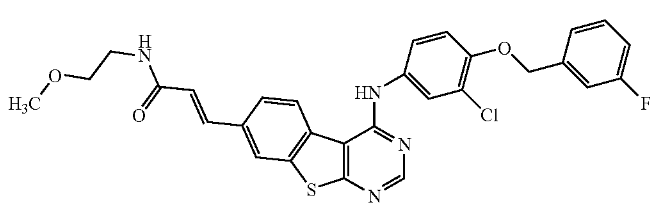 | 3.62 | 563.10 | (2E)-3-[4-({3-chloro-4-[(3-fluorobenzyl)oxy]phenyl}amino)[1]benzothieno[2,3-d]pyrimidin-7-yl]-N-(2-methoxyethyl)acrylamide |

-continued

| Example | Structure | LCMS RT (min) | LCMS Ion [M + H]+ | IUPAC Name |
|---|---|---|---|---|
| 51 | 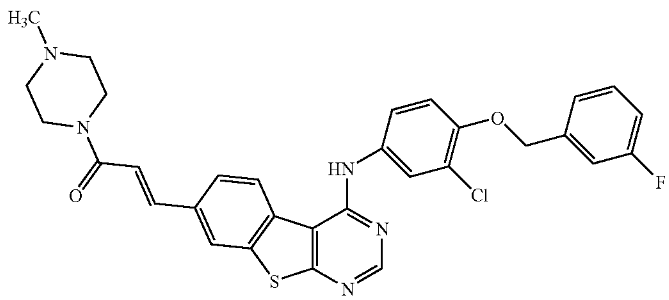 | 2.92 | 588.10 | N-{3-chloro-4-[(3-fluorobenzyl)oxy]phenyl}-7-[(1E)-3-(4-methylpiperazin-1-yl)-3-oxoprop-1-en-1-yl][1]benzothieno[2,3-d]pyrimidin-4-amine |
| 52 | 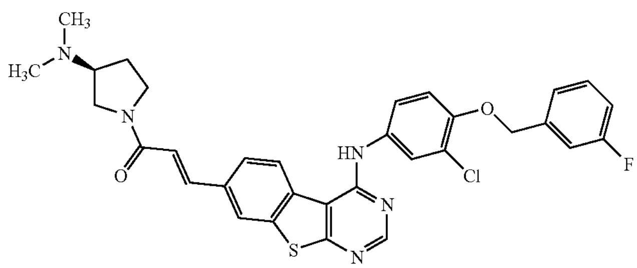 | 2.96 | 602.10 | N-{3-chloro-4-[(3-fluorobenzyl)oxy]phenyl}-7-{(1E)-3-[(3S)-3-(dimethylamino)pyrrolidin-1-yl]-3-oxoprop-1-en-1-yl}[1]benzothieno[2,3-d]pyrimidin-4-amine |
| 53 | 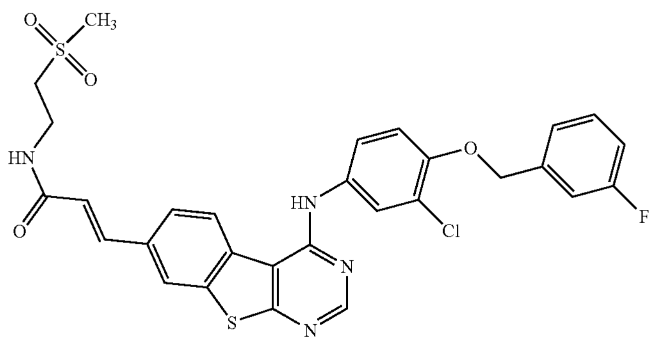 | 3.55 | 611.00 | (2E)-3-[4-({3-chloro-4-[(3-fluorobenzyl)oxy]phenyl}amino)[1]benzothieno[2,3-d]pyrimidin-7-yl]-N-[2-(methylsulfonyl)ethyl]acrylamide |
| 54 | 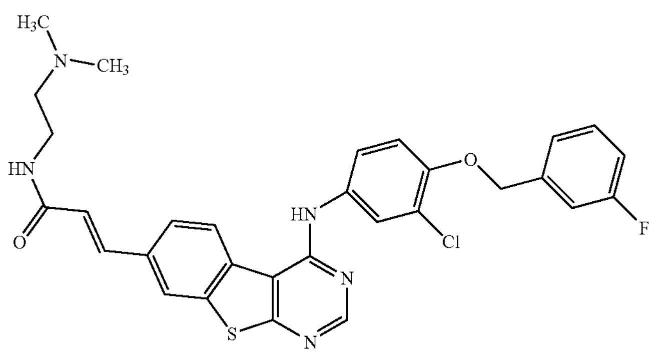 | 2.97 | 576.10 | (2E)-3-[4-({3-chloro-4-[(3-fluorobenzyl)oxy]phenyl}amino)[1]benzothieno[2,3-d]pyrimidin-7-yl]-N-[2-(dimethylamino)ethyl]acrylamide |

-continued

| Example | Structure | LCMS RT (min) | LCMS Ion [M + H]+ | IUPAC Name |
|---|---|---|---|---|
| 55 | 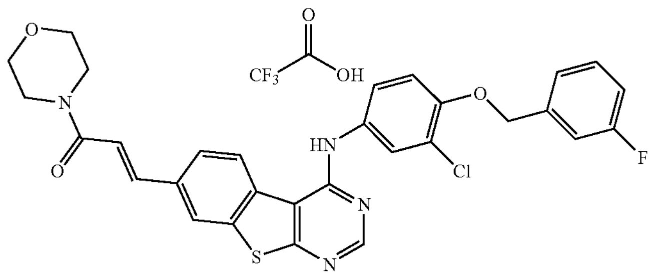 | 3.71 | 575.10 | N-{3-chloro-4-[(3-fluorobenzyl)oxy]phenyl}-7-[(1E)-3-morpholin-4-yl-3-oxoprop-1-en-1-yl][1]benzothieno[2,3-d]pyrimidin-4-amine trifluoroacetate |
| 56 | 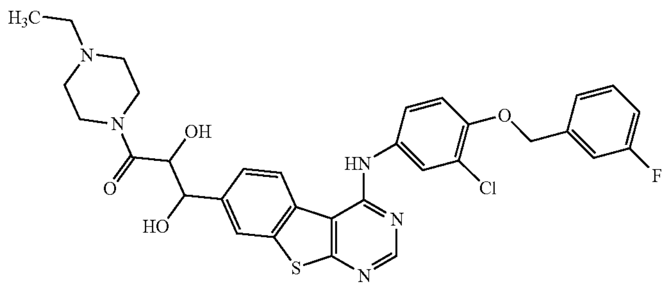 | 2.67 | 636.00 | 1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol |
| 57 | 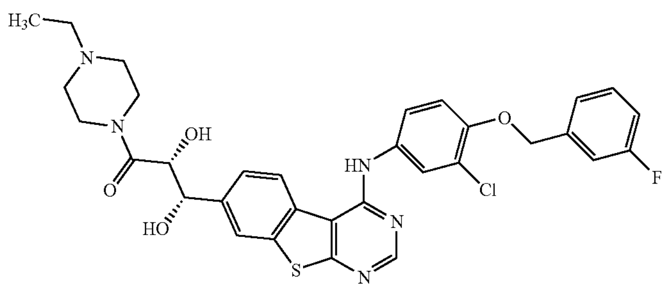 | 2.68 | 636.10 | (1S,2R)-1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol |
| 58 | 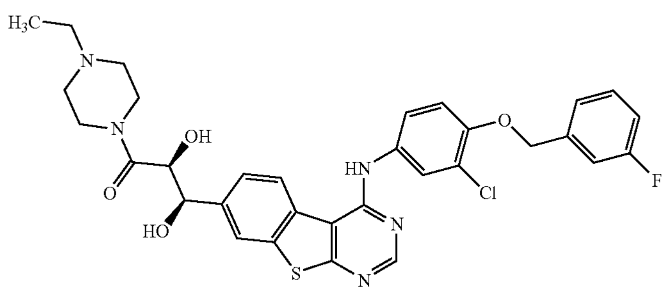 | 2.72 | 636.10 | (1R,2S)-1-[4-({3-chloro-4-[(3-fluorobenzyl)oxy]phenyl}amino)[1]benzothieno[2,3-d]pyrimidin-7-yl]-3-(4-ethylpiperazin-1-yl)-3-oxopropane-1,2-diol |
| 59 | 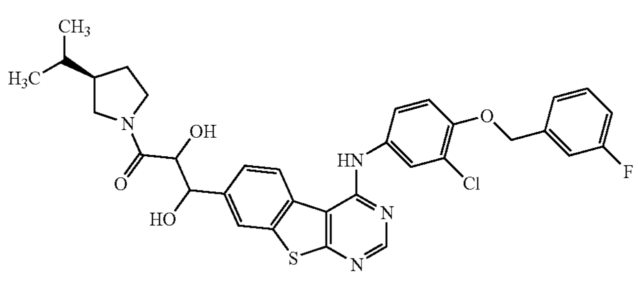 | 2.69 | 636.10 | 1-[4-({3-chloro-4-[(3-fluorobenzyl)oxy]phenyl}amino)[1]benzothieno[2,3-d]pyrimidin-7-yl]-3-[(3S)-3-(dimethylamino)pyrrolidin-1-yl]-3-oxopropane-1,2-diol |

-continued

| Example | Structure | LCMS RT (min) | LCMS Ion [M + H]+ | IUPAC Name |
|---|---|---|---|---|
| 60 | 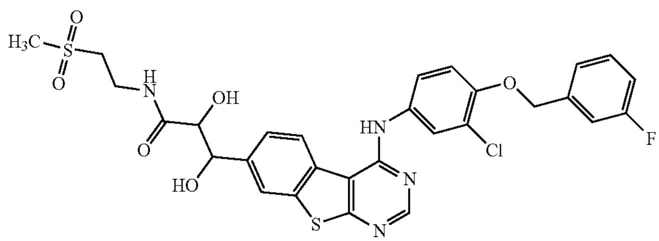 | 3.12 | 645.10 | 3-[4-({3-chloro-4-[(3-fluorobenzyl)oxy]phenyl}amino)[1]benzothieno[2,3-d]pyrimidin-7-yl]-2,3-dihydroxy-N-[2-(methylsulfonyl)ethyl]propanamide |
| 61 | 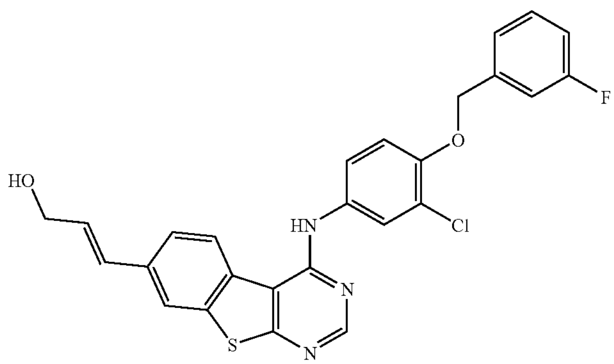 | 3.71 | 492.10 | (2E)-3-[4-({3-chloro-4-[(3-fluorobenzyl)oxy]phenyl}amino)[1]benzothieno[2,3-d]pyrimidin-7-yl]prop-2-en-1-ol |
| 62 | 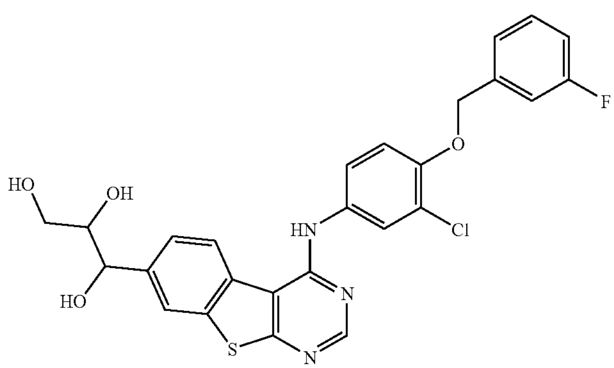 | 3.16 | 526.10 | 1-[4-({3-chloro-4-[(3-fluorobenzyl)oxy]phenyl}amino)[1]benzothieno[2,3-d]pyrimidin-7-yl]propane-1,2,3-triol |
| 63 | 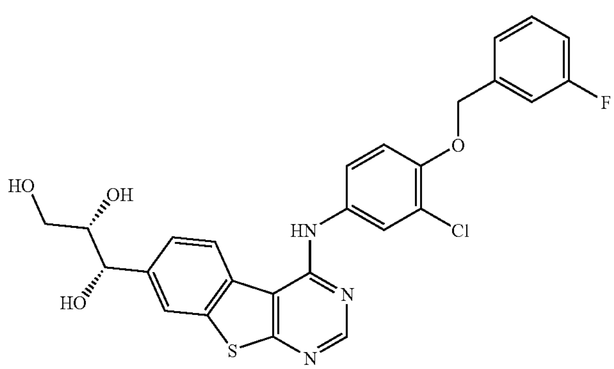 | 3.14 | 526.00 | (1S,2S)-1-[4-({3-chloro-4-[(3-fluorobenzyl)oxy]phenyl}amino)[1]benzothieno[2,3-d]pyrimidin-7-yl]propane-1,2,3-triol |

-continued

| Example | Structure | LCMS RT (min) | LCMS Ion [M+H]+ | IUPAC Name |
|---|---|---|---|---|
| 64 | 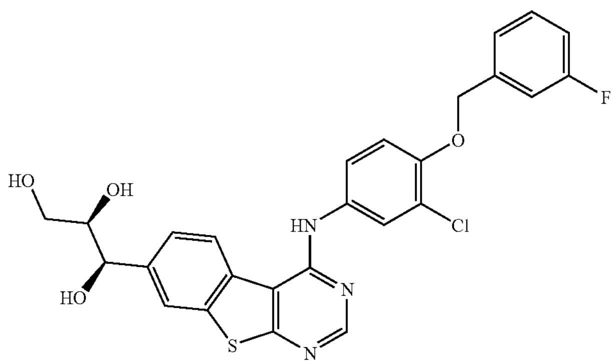 | 3.13 | 526.10 | (1R,2R)-1-[4-({3-chloro-4-[(3-fluorobenzyl)oxy]phenyl}amino)[1]benzothieno[2,3-d]pyrimidin-7-yl]propane-1,2,3-triol |
| 65 | 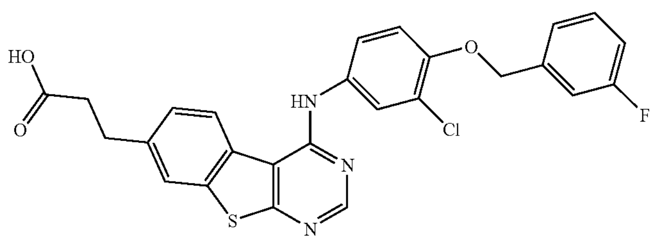 | 3.73 | 508.10 | 3-[4-({3-chloro-4-[(3-fluorobenzyl)oxy]phenyl}amino)[1]benzothieno[2,3-d]pyrimidin-7-yl]propanoic acid |
| 66 | 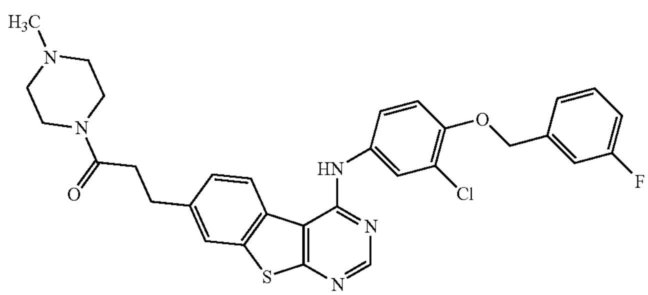 | 2.87 | 590.20 | N-{3-chloro-4-[(3-fluorobenzyl)oxy]phenyl}-7-[3-(4-methylpiperazin-1-yl)-3-oxopropyl][1]benzothieno[2,3-d]pyrimidin-4-amine |
| 67 | 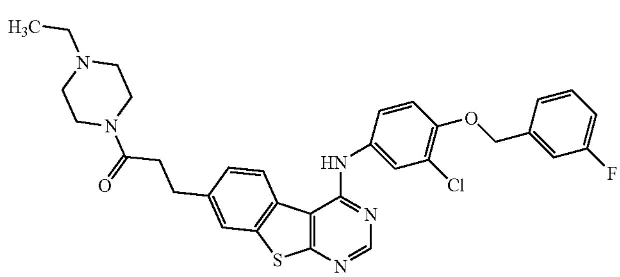 | 2.90 | 604.20 | N-{3-chloro-4-[(3-fluorobenzyl)oxy]phenyl}-7-[3-(4-ethylpiperazin-1-yl)-3-oxopropyl][1]benzothieno[2,3-d]pyrimidin-4-amine |
| 68 | 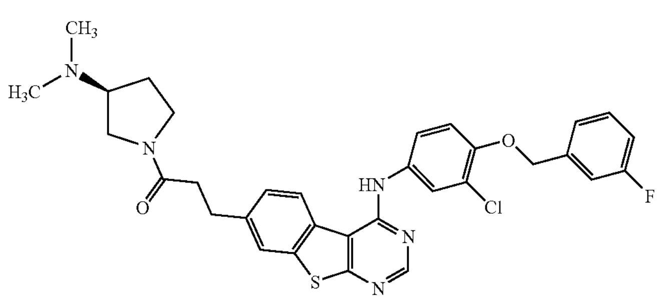 | 2.91 | 604.10 | N-{3-chloro-4-[(3-fluorobenzyl)oxy]phenyl}-7-{3-[(3S)-3-(dimethylamino)pyrrolidin-1-yl]-3-oxopropyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 69 | 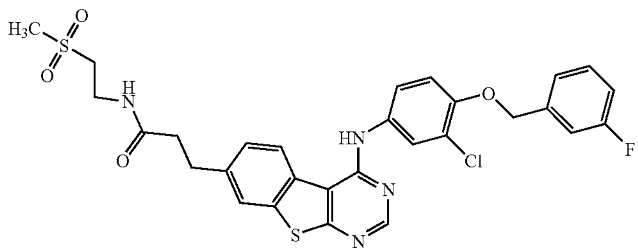 | 3.47 | 613.10 | 3-[4-({3-chloro-4-[(3-fluorobenzyl)oxy]phenyl}amino)[1]benzothieno[2,3-d]pyrimidin-7-yl]-N-[2-(methylsulfonyl)ethyl]propanamide |
| 70 | 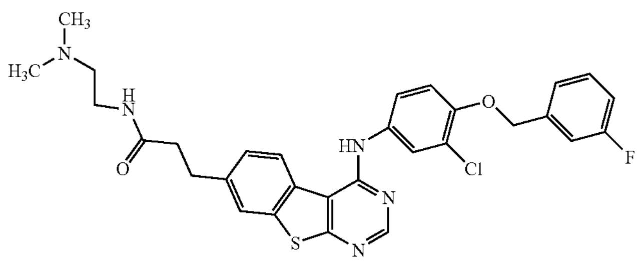 | 2.86 | 578.10 | 3-[4-({3-chloro-4-[(3-fluorobenzyl)oxy]phenyl}amino)[1]benzothieno[2,3-d]pyrimidin-7-yl]-N-[2-(dimethylamino)ethyl]propanamide |
| 71 | 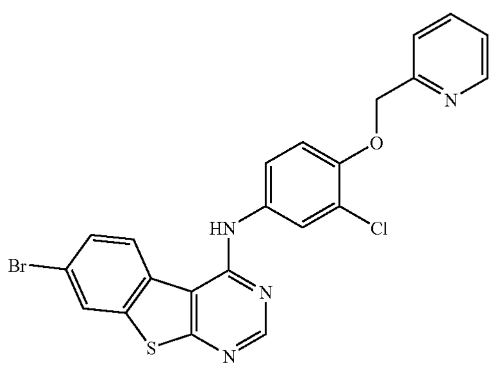 | 3.43 | 499.00 | 7-bromo-N-[3-chloro-4-(pyridin-2-ylmethoxy)phenyl][1]benzothieno[2,3-d]pyrimidin-4-amine |
| 72 | 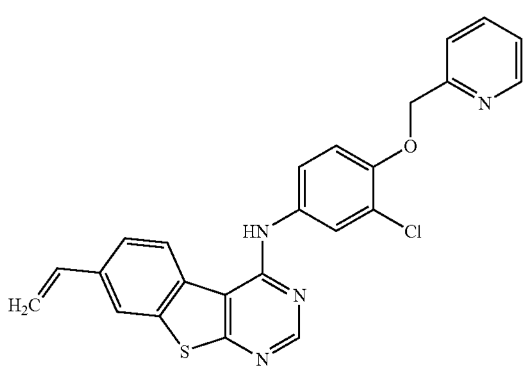 | 3.30 | 445.10 | N-[3-chloro-4-(pyridin-2-ylmethoxy)phenyl]-7-vinyl[1]benzothieno[2,3-d]pyrimidin-4-amine |

-continued

| Example | Structure | LCMS RT (min) | LCMS Ion [M + H]+ | IUPAC Name |
|---|---|---|---|---|
| 73 | 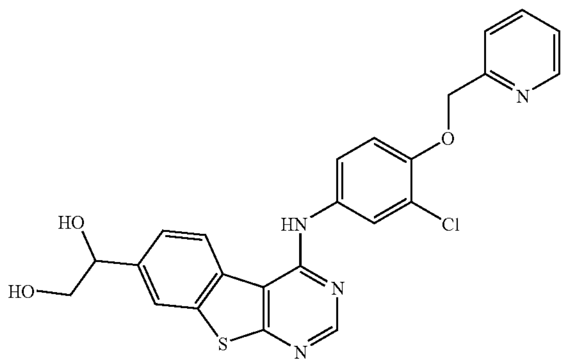 | 2.39 | 479.10 | 1-(4-{[3-chloro-4-(pyridin-2-ylmethoxy)phenyl]amino}[1]benzothieno[2,3-d]pyrimidin-7-yl)ethane-1,2-diol |
| 74 | 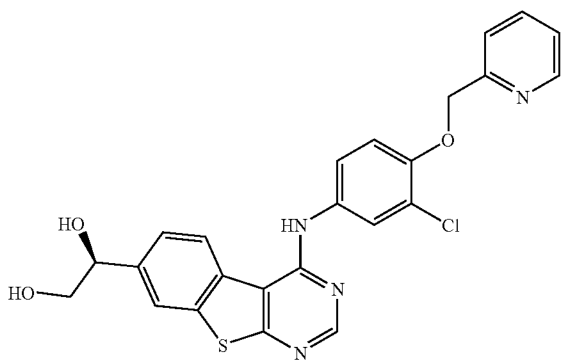 | 2.39 | 479.10 | (1S)-1-(4-{[3-chloro-4-(pyridin-2-ylmethoxy)phenyl]amino}[1]benzothieno[2,3-d]pyrimidin-7-yl)ethane-1,2-diol |
| 75 | 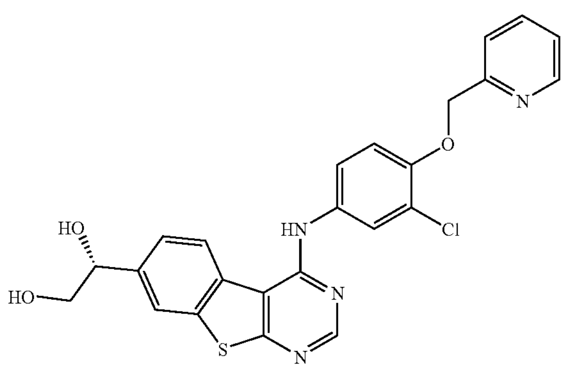 | 2.39 | 479.10 | (1R)-1-(4-{[3-chloro-4-(pyridin-2-ylmethoxy)phenyl]amino}[1]benzothieno[2,3-d]pyrimidin-7-yl)ethane-1,2-diol |
| 76 | 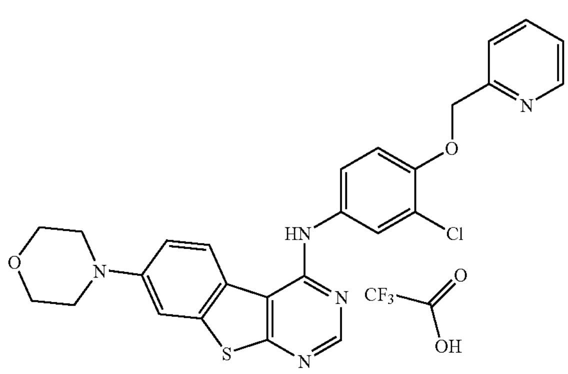 | 3.01 | 506.00 | N-[3-chloro-4-(pyridin-2-ylmethoxy)phenyl]-7-morpholin-4-yl[1]benzothieno[2,3-d]pyrimidin-4-amine trifluoroacetate |

-continued

| Example | Structure | LCMS RT (min) | LCMS Ion [M + H]+ | IUPAC Name |
|---|---|---|---|---|
| 77 | 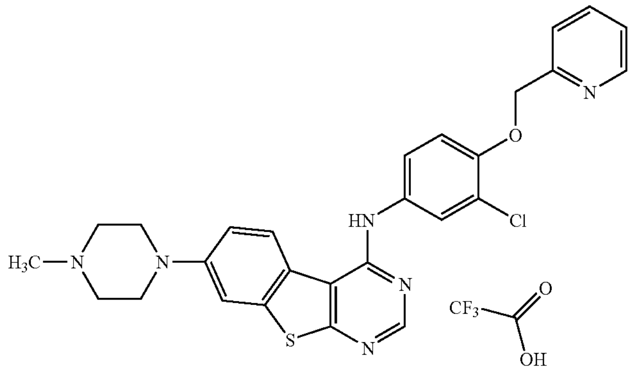 | 2.24 | 517.00 | N-[3-chloro-4-(pyridin-2-ylmethoxy)phenyl]-7-(4-methylpiperazin-1-yl)[1]benzothieno[2,3-d]pyrimidin-4-amine trifluoroacetate |
| 78 | 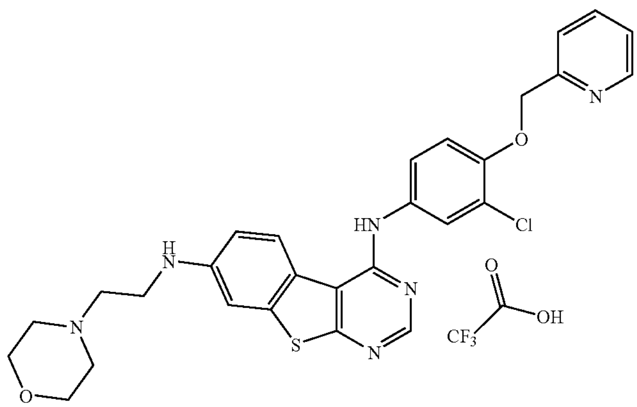 | 2.25 | 547.10 | N4-[3-chloro-4-(pyridin-2-ylmethoxy)phenyl]-N7-(2-morpholin-4-ylethyl)[1]benzothieno[2,3-d]pyrimidine-4,7-diamine trifluoroacetate |
| 79 | 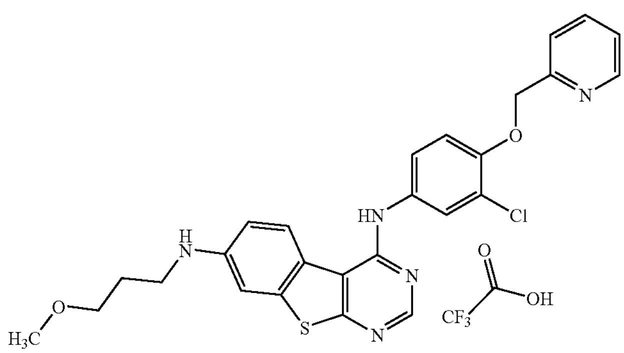 | 2.90 | 506.10 | N4-[3-chloro-4-(pyridin-2-ylmethoxy)phenyl]-N7-(3-methoxypropyl)[1]benzothieno[2,3-d]pyrimidine-4,7-diamine trifluoroacetate |
| 80 | 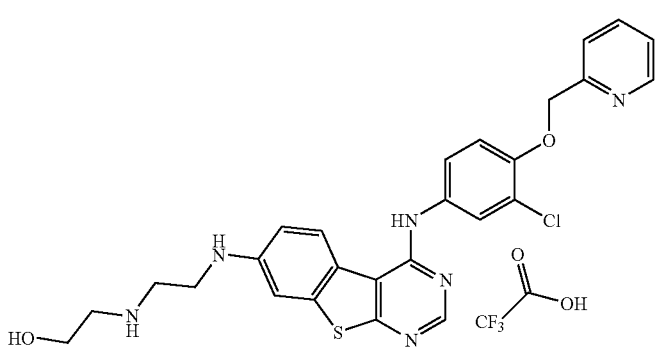 | 2.61 | 522.10 | 2-{2-[(4-{[3-chloro-4-(pyridin-2-ylmethoxy)phenyl]amino}[1]benzothieno[2,3-d]pyrimidin-7-yl)amino]ethoxy}ethanol trifluoroacetate (salt) |

-continued

| Example | Structure | LCMS RT (min) | LCMS Ion [M + H]+ | IUPAC Name |
|---|---|---|---|---|
| 81 | 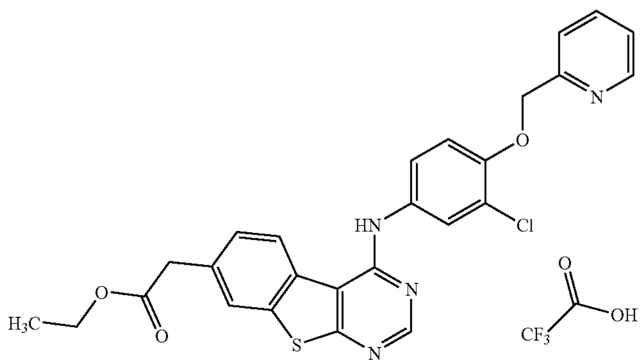 | 3.25 | 505.20 | ethyl {4-[3-Chloro-4-(pyridin-2-ylmethoxy)-phenylamino]-benzo[4,5]thieno[2,3-d]pyrimidin-7-yl}-acetate trifluoroacetate |
| 82 | 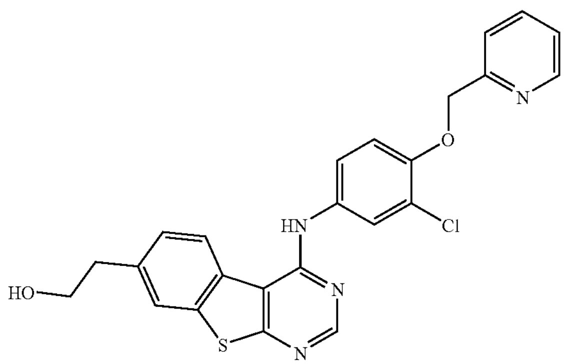 | 3.08 | 463.20 | 2-(4-{[3-chloro-4-(pyridin-2-ylmethoxy)phenyl]amino}[1]benzothieno[2,3-d]pyrimidin-7-yl)ethanol |
| 83 | 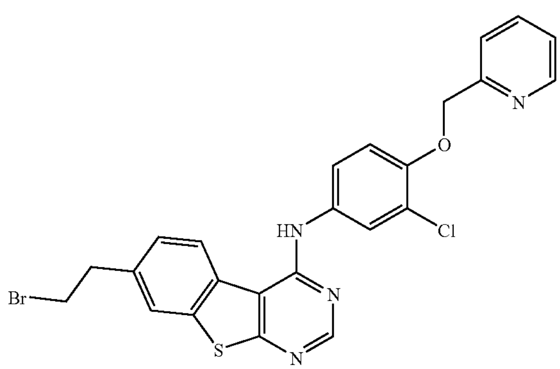 | 3.27 | 525.20 | 7-(2-bromoethyl)-N-[3-chloro-4-(pyridin-2-ylmethoxy)phenyl][1]benzothieno[2,3-d]pyrimidin-4-amine |
| 84 | 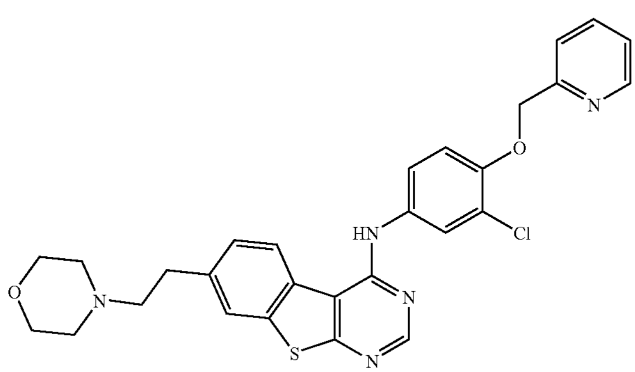 | 2.31 | 533.40 | N-[3-chloro-4-(pyridin-2-ylmethoxy)phenyl]-7-(2-morpholin-4-ylethyl)[1]benzothieno[2,3-d]pyrimidin-4-amine |

| Example | Structure | LCMS RT (min) | LCMS Ion [M + H]+ | IUPAC Name |
|---|---|---|---|---|
| 85 | 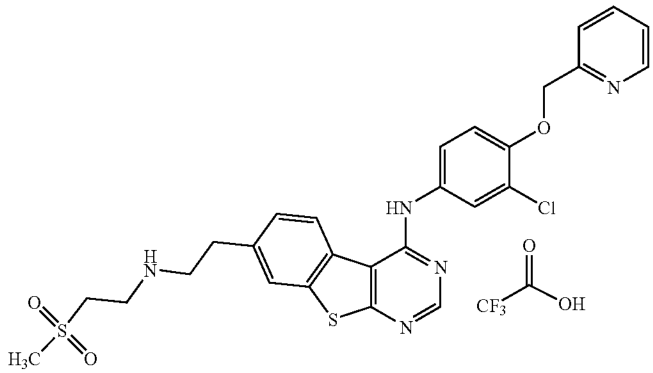 | 2.25 | 569.10 | N-[3-chloro-4-(pyridin-2-ylmethoxy)phenyl]-7-(2-{[2-(methylsulfonyl)ethyl]amino}ethyl)[1]benzothieno[2,3-d]pyrimidin-4-amine trifluoroacetate |
| 86 | 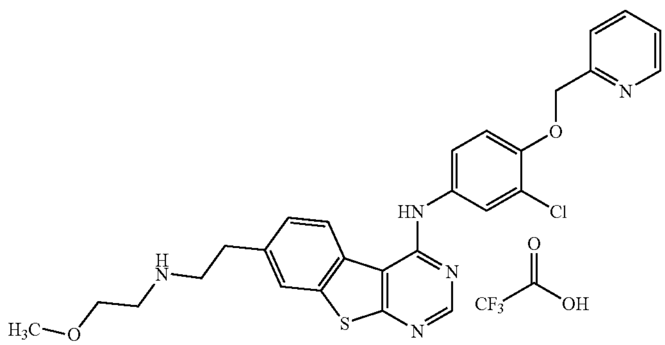 | 2.26 | 520.10 | N-[3-chloro-4-(pyridin-2-ylmethoxy)phenyl]-7-{2-[(2-methoxyethyl)amino]ethyl}[1]benzothieno[2,3-d]pyrimidin-4-amine trifluoroacetate |
| 87 | 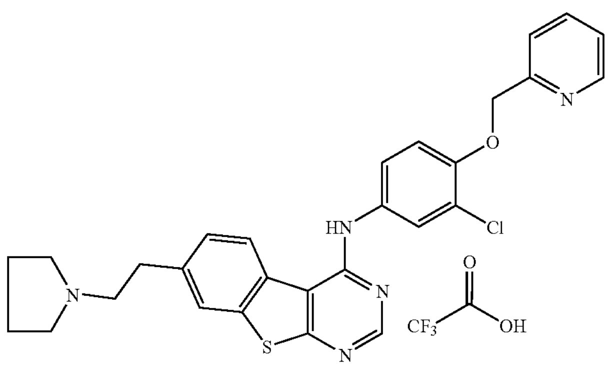 | 2.29 | 516.10 | N-[3-chloro-4-(pyridin-2-ylmethoxy)phenyl]-7-(2-pyrrolidin-1-ylethyl)[1]benzothieno[2,3-d]pyrimidin-4-amine trifluoroacetate |
| 88 | 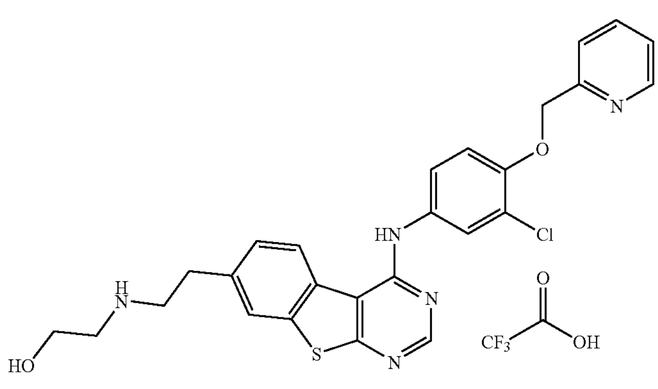 | 2.20 | 507.00 | 2-{[2-(4-{[3-chloro-4-(pyridin-2-ylmethoxy)phenyl]amino}[1]benzothieno[2,3-d]pyrimidin-7-yl)ethyl]amino}ethanol trifluoroacetate (salt) |

-continued

| Example | Structure | LCMS RT (min) | LCMS Ion [M + H]+ | IUPAC Name |
|---|---|---|---|---|
| 89 | 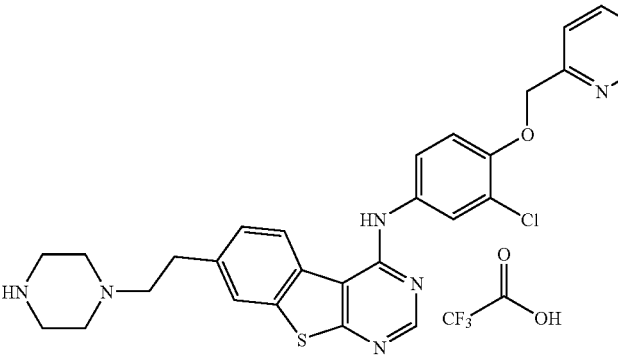 | 2.09 | 531.20 | N-[3-chloro-4-(pyridin-2-ylmethoxy)phenyl]-7-(2-piperazin-1-ylethyl)[1]benzothieno[2,3-d]pyrimidin-4-amine trifluoroacetate |
| 90 | 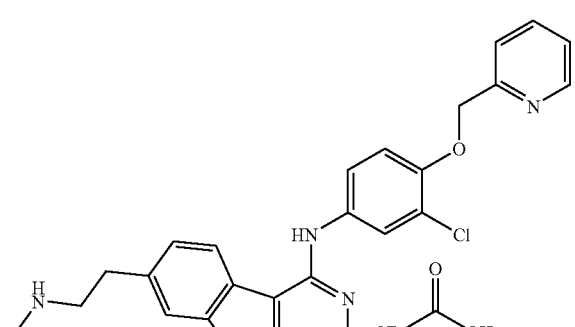 | 2.25 | 490.10 | N-[3-chloro-4-(pyridin-2-ylmethoxy)phenyl]-7-[2-(ethylamino)ethyl][1]benzothieno[2,3-d]pyrimidin-4-amine trifluoroacetate |
| 91 | 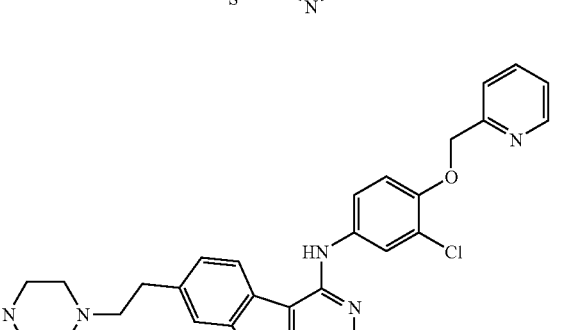 | 2.11 | 545.20 | N-[3-chloro-4-(pyridin-2-ylmethoxy)phenyl]-7-[2-(4-(methylpiperazin-1-yl)ethyl][1]benzothieno[2,3-d]pyrimidin-4-amine |
| 92 | 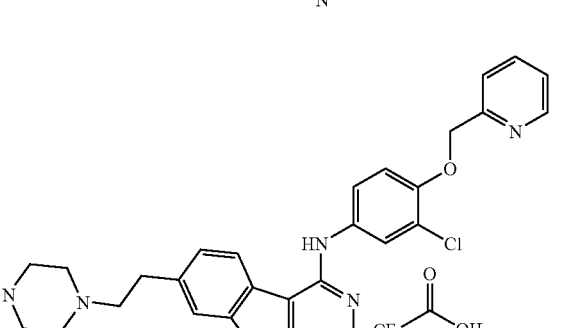 | 2.16 | 545.40 | N-[3-chloro-4-(pyridin-2-ylmethoxy)phenyl]-7-[2-(4-methylpiperazin-1-yl)ethyl][1]benzothieno[2,3-d]pyrimidin-4-amine trifluoroacetate |

-continued

| Example | Structure | LCMS RT (min) | LCMS Ion [M + H]+ | IUPAC Name |
|---|---|---|---|---|
| 93 | 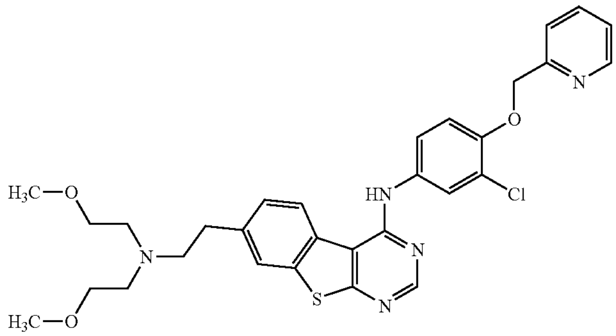 | 2.38 | 578.30 | 7-{2-[bis(2-methoxyethyl)amino]ethyl}-N-[3-chloro-4-(pyridin-2-ylmethoxy)phenyl][1]benzothieno[2,3-d]pyrimidin-4-amine trifluoroacetate |
| 94 | 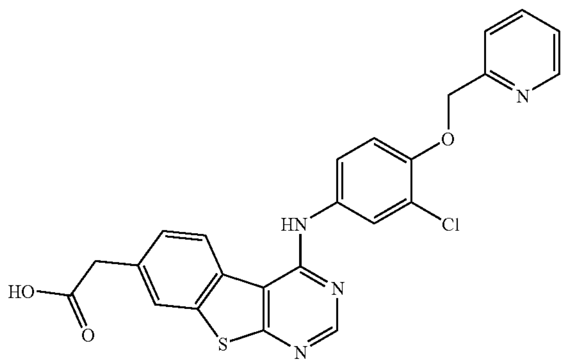 | 3.08 | 477.20 | (4-{[3-chloro-4-(pyridin-2-ylmethoxy)phenyl]amino}[1]benzothieno[2,3-d]pyrimidin-7-yl)acetic acid |
| 95 | 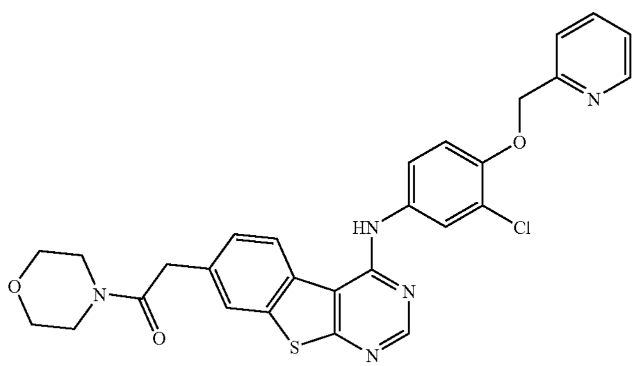 | 2.69 | 546.20 | N-[3-chloro-4-(pyridin-2-ylmethoxy)phenyl]-7-(2-morpholin-4-yl-2-oxoethyl)[1]benzothieno[2,3-d]pyrimidin-4-amine |
| 96 | 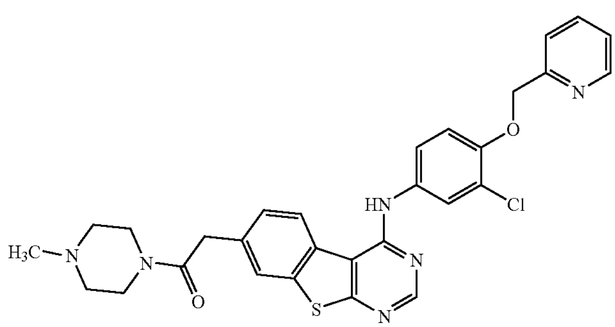 | 2.43 | 559.40 | N-[3-chloro-4-(pyridin-2-ylmethoxy)phenyl]-7-[2-(4-methylpiperazin-1-yl)-2-oxoethyl][1]benzothieno[2,3-d]pyrimidin-4-amine |

-continued

| Example | Structure | LCMS RT (min) | LCMS Ion [M+H]+ | IUPAC Name |
|---|---|---|---|---|
| 97 | 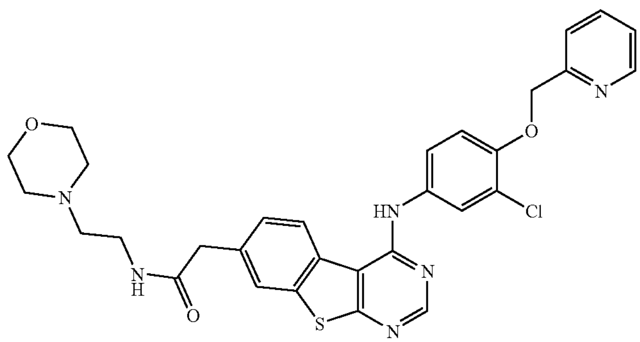 | 2.29 | 589.10 | 2-(4-{[3-chloro-4-(pyridin-2-ylmethoxy)phenyl]amino}[1]benzothieno[2,3-d]pyrimidin-7-yl)-N-(2-morpholin-4-ylethyl)acetamide |
| 98 | 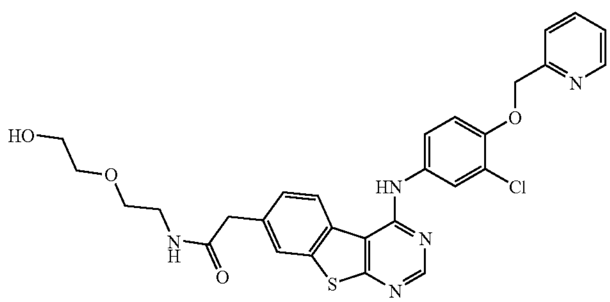 | 2.48 | 564.10 | 2-(4-{[3-chloro-4-(pyridin-2-ylmethoxy)phenyl]amino}[1]benzothieno[2,3-d]pyrimidin-7-yl)-N-[2-(2-hydroxyethoxy)ethyl]acetamide |
| 99 | 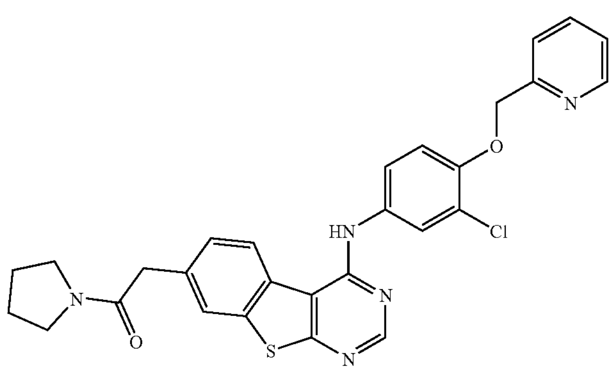 | 2.83 | 530.10 | N-[3-chloro-4-(pyridin-2-ylmethoxy)phenyl]-7-(2-oxo-2-pyrrolidin-1-ylethyl)[1]benzothieno[2,3-d]pyrimidin-4-amine |
| 100 | 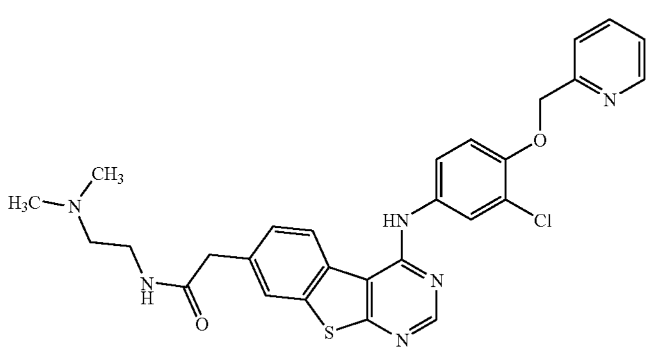 | 2.27 | 547.10 | 2-(4-{[3-chloro-4-(pyridin-2-ylmethoxy)phenyl]amino}[1]benzothieno[2,3-d]pyrimidin-7-yl)-N-[(2-dimethylamino)ethyl]acetamide |

-continued

| Example | Structure | LCMS RT (min) | LCMS Ion [M + H]+ | IUPAC Name |
|---|---|---|---|---|
| 101 | 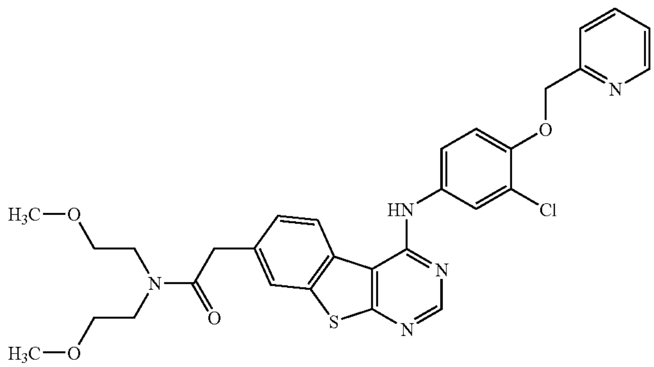 | 2.91 | 592.10 | 2-(4-{[3-chloro-4-(pyridin-2-ylmethoxy)phenyl]amino}[1]benzothieno[2,3-d]pyrimidin-7-yl)-N,N-bis (2-methoxyethyl)acetamide |
| 102 | 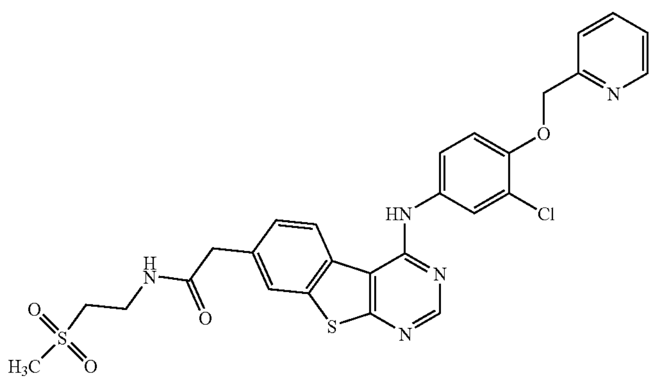 | 2.58 | 604.10 | 2-(4-{[3-chloro-4-(pyridin-2-ylmethoxy)phenyl]amino}[1]benzothieno[2,3-d]pyrimidin-7-yl)-N-[2-(methylsulfonyl)ethyl]acetamide |
| 103 | 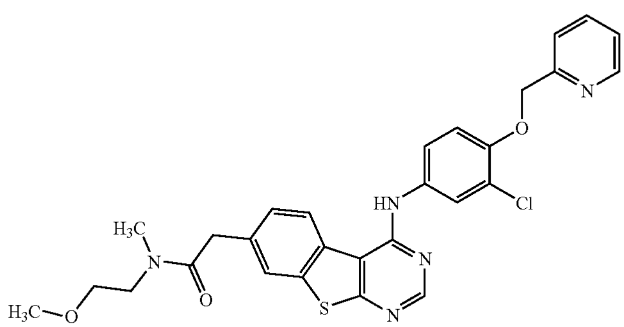 | 2.79 | 548.00 | 2-(4-{[3-chloro-4-(pyridin-2-ylmethoxy)phenyl]amino}[1]benzothieno[2,3-d]pyrimidin-7-yl)-N-(2-methoxyethyl)-N-methylacetamide |
| 104 | 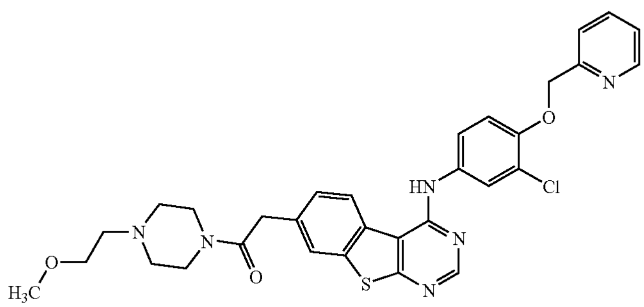 | 2.29 | 603.00 | N-[3-chloro-4-(pyridin-2-ylmethoxy)phenyl]-7-{2-[4-(2-methoxyethyl)piperazin-1-yl]-2-oxoethyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 105 | 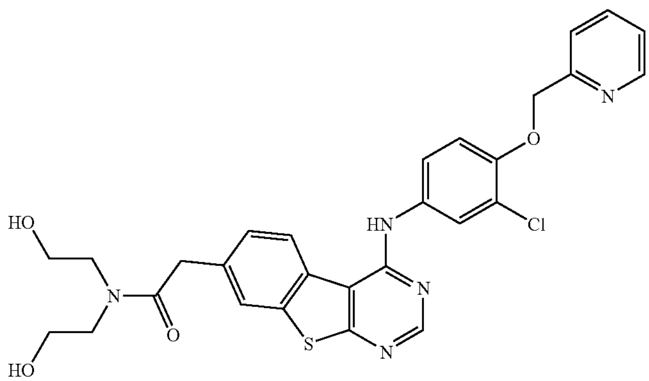 | 2.44 | 586.90 | 2(4-{[3-chloro-4-(pyridin-2-ylmethoxy)phenyl]amino}[1]benzothieno[2,3-d]pyrimidin-7-yl)-N,N-bis-(2-hydroxyethyl)acetamide |
| 106 | 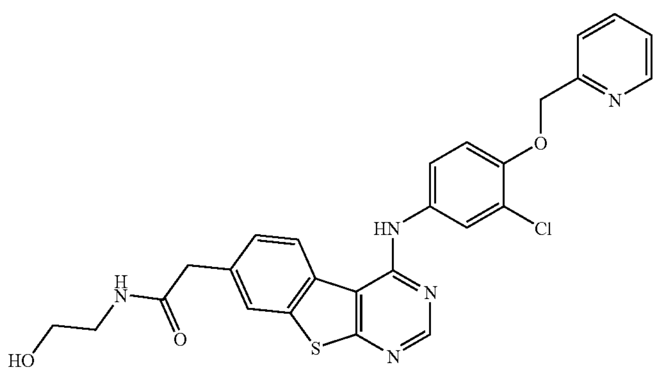 | 2.47 | 520.20 | 2(4-{[3-chloro-4-(pyridin-2-ylmethoxy)phenyl]amino}[1]benzothieno[2,3-d]pyrimidin-7-yl)-N-(2-hydroxyethyl)acetamide |
| 107 | 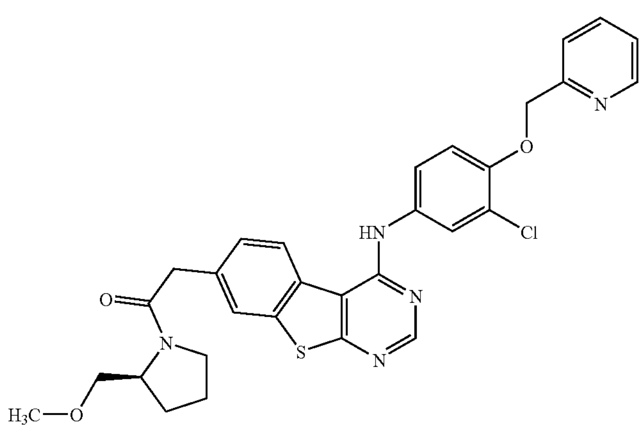 | 2.95 | 574.10 | N-[3-chloro-4-(pyridin-2-ylmethoxy)phenyl]-7-{2-[2-(methoxymethyl)pyrrolidin-1-yl]-2-oxoethyl}[1]benzothieno[2,3-d]pyrimidin-4-amine |

-continued

| Example | Structure | LCMS RT (min) | LCMS Ion [M + H]+ | IUPAC Name |
|---|---|---|---|---|
| 108 | 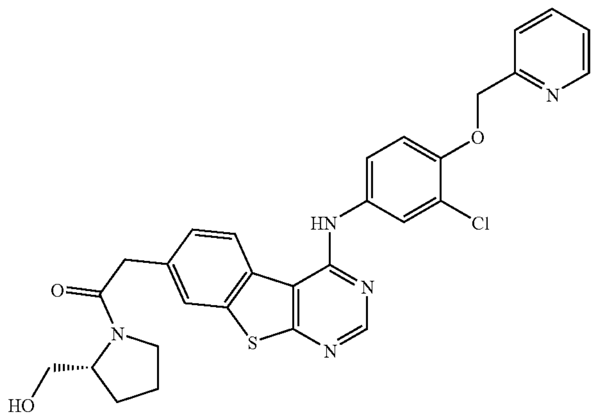 | 2.66 | 560.10 | {1-[(4-{[3-chloro-4-(pyridin-2-ylmethoxy)phenyl]amino}[1]benzothieno[2,3-d]pyrimidin-7-yl)acetyl]pyrrolidin-2-yl}methanol |
| 109 | 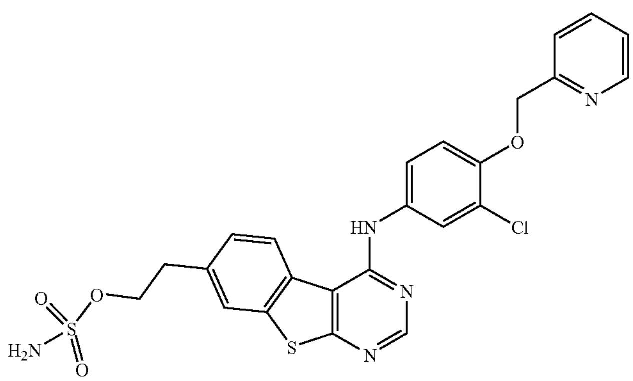 | 3.08 | 542.10 | 2(4-{[3-chloro-4-(pyridin-2-ylmethoxy)phenyl]amino}[1]benzothieno[2,3-d]pyrimidin-7-yl)ethyl sulfamate |
| 110 | 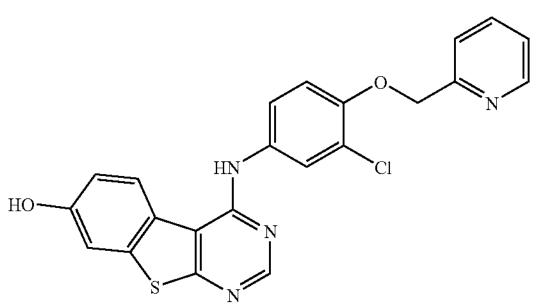 | 2.65 | 435.10 | 4-{[3-chloro-4-(pyridin-2-ylmethoxy)phenyl]amino}[1]benzothieno[2,3-d]pyrimidin-7-ol |
| 111 | 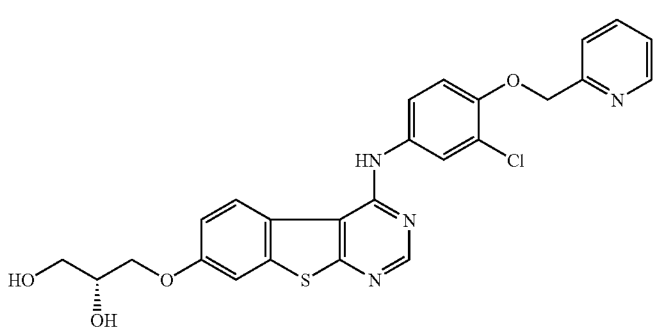 | 2.59 | 511.10 | (2R)-3-[(4-{[3-chloro-4-(pyridin-2-ylmethoxy)phenyl]amino}[1]benzothieno[2,3-d]pyrimidin-7-yl)oxy]propane-1,2-diol |

-continued

| Example | Structure | LCMS RT (min) | LCMS Ion [M + H]+ | IUPAC Name |
| --- | --- | --- | --- | --- |
| 112 | 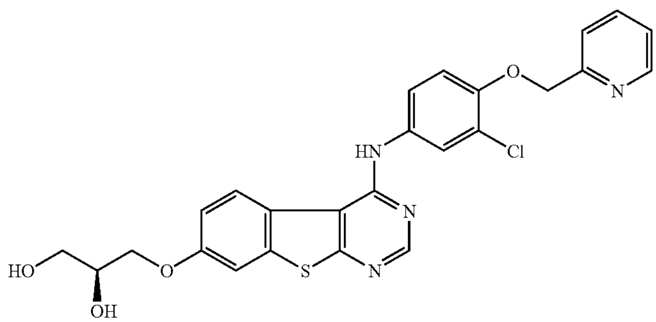 | 2.64 | 511.10 | (2S)-3-[(4-{[3-chloro-4-(pyridin-2-ylmethoxy)phenyl]amino}[1]benzothieno[2,3-d]pyrimidin-7-yl)oxy]propane-1,2-diol |
| 113 | 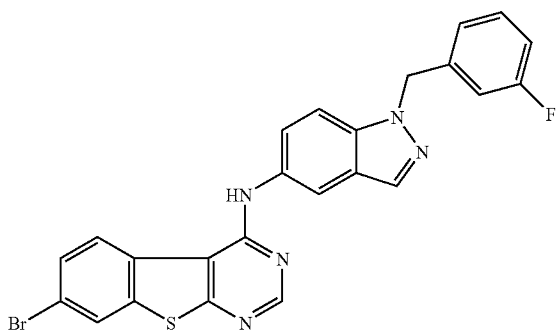 | 3.91 | 507.20 | 7-bromo-N-[1-(3-fluorobenzyl)-1H-indazol-5-yl][1]benzothieno[2,3-d]pyrimidin-4-amine |
| 114 | 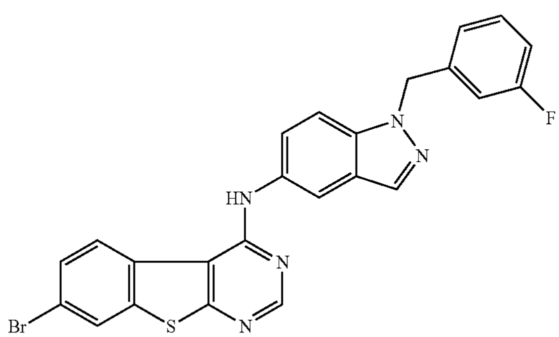 | 3.78 | 452.20 | N-[1-(3-fluorobenzyl)-1H-indazol-5-yl]-7-vinyl[1]benzothieno[2,3-d]pyrimidin-4-amine |
| 115 | 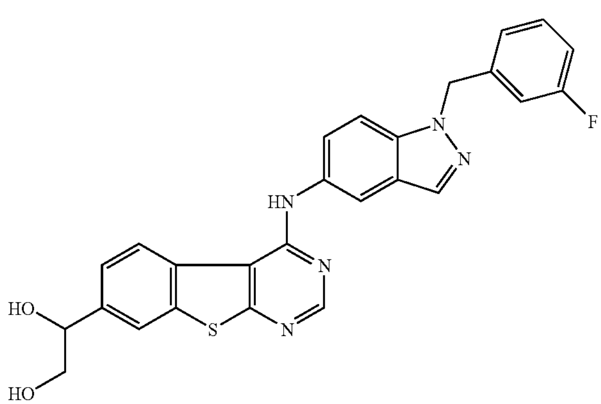 | 2.81 | 486.30 | 1-(4-{[1-(3-fluorobenzyl)-1H-indazol-5-yl]amino}[1]benzothieno[2,3-d]pyrimidin-7-yl)ethane-1,2-diol |

-continued

| Example | Structure | LCMS RT (min) | LCMS Ion [M + H]+ | IUPAC Name |
|---|---|---|---|---|
| 116 | 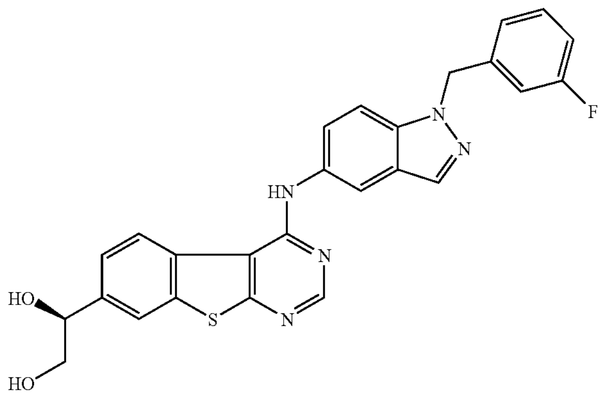 | 2.84 | 487.20 | (1S)-1-(4-{[1-(3-fluorobenzyl)-1H-indazol-5-yl]amino}[1]benzothieno[2,3-d]pyrimidin-7-yl)ethane-1,2-diol |
| 117 | 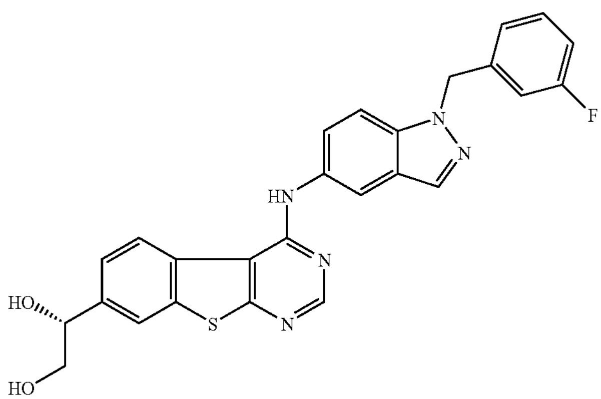 | 2.84 | 487.20 | (1R)-1-(4-{[1-(3-fluorobenzyl)-1H-indazol-5-yl]amino}[1]benzothieno[2,3-d]pyrimidin-7-yl)ethane-1,2-diol |
| 118 | 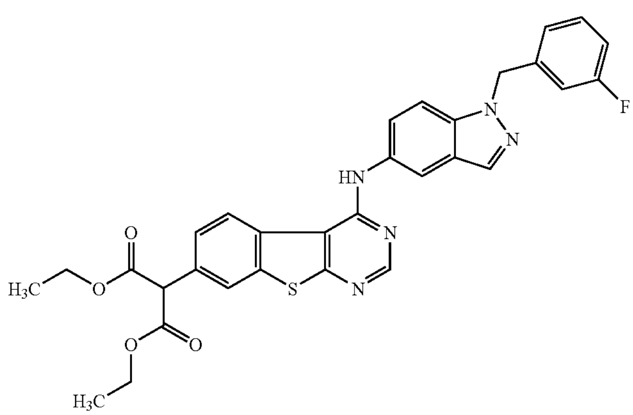 | 3.78 | 584.10 | diethyl (4-{[1-(3-fluorobenzyl)-1H-indazol-5-yl]amino}[1]benzothieno[2,3-d]pyrimidin-7-yl)malonate |

-continued

| Example | Structure | LCMS RT (min) | LCMS Ion [M + H]+ | IUPAC Name |
|---|---|---|---|---|
| 119 | 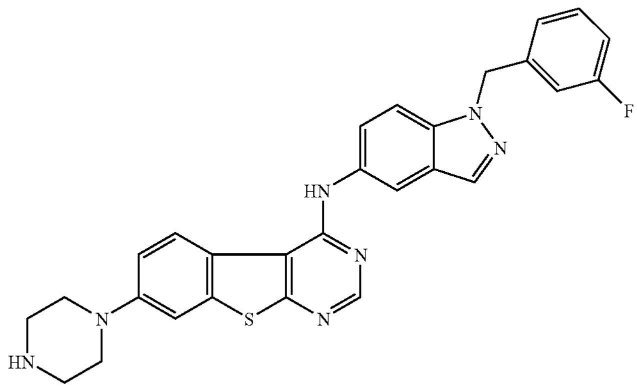 | 2.55 | 510.30 | N-[1-(3-fluorobenzyl)-1H-indazol-5-yl]-7-piperazin-1-yl[1]benzothieno[2,3-d]pyrimidin-4-amine |
| 120 | 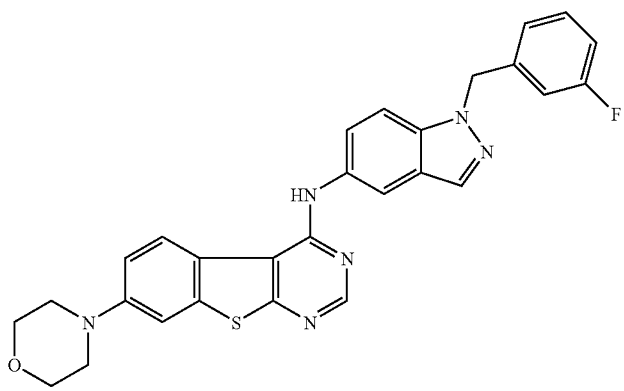 | 3.43 | 511.20 | N-[1-(3-fluorobenzyl)-1H-indazol-5-yl]-7-morpholin-4-yl[1]benzothieno[2,3-d]pyrimidin-4-amine |
| 121 | 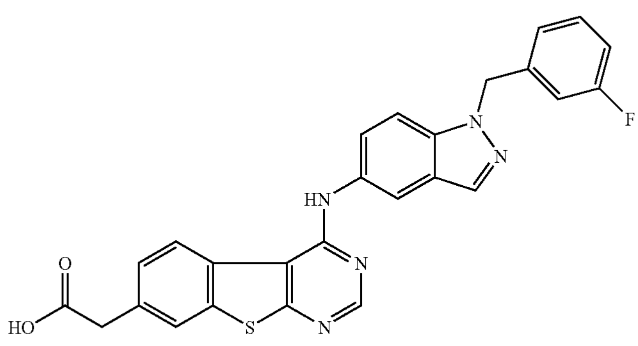 | 2.91 | 484.30 | (4-{[1-(3-fluorobenzyl)-1H-indazol-5-yl]amino}[1]benzothieno[2,3-d]pyrimidin-7-yl)acetic acid |
| 122 | 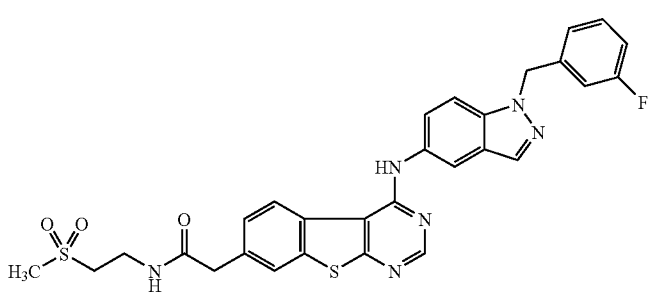 | 3.25 | 589.30 | 2-(4-{[1-(3-fluorobenzyl)-1H-indazol-5-yl]amino}[1]benzothieno[2,3-d]pyrimidin-7-yl)-N-[2-(methylsulfonyl)ethyl]acetamide |

-continued

| Example | Structure | LCMS RT (min) | LCMS Ion [M + H]+ | IUPAC Name |
|---|---|---|---|---|
| 123 | 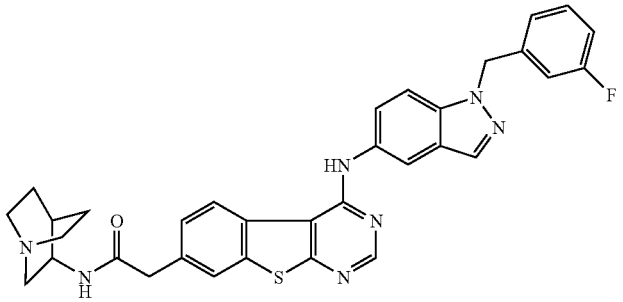 | 2.47 | 592.30 | N-1-azabicyclo[2.2.2]oct-3-yl-2-(4-{[1-(3-fluorobenzyl)-1H-indazol-5-yl]amino}[1]benzothieno[2,3-d]pyrimidin-7-yl)acetamide |
| 124 | 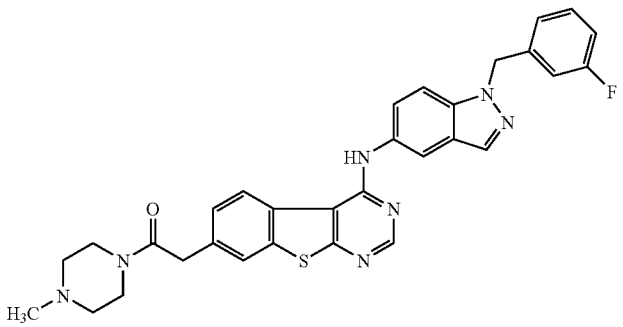 | 2.89 | 566.50 | N-[1-(3-fluorobenzyl)-1H-indazol-5-yl]-7-[2-(4-methylpiperazin-1-yl)-2-oxoethyl][1]benzothieno[2,3-d]pyrimidin-4-amine |
| 125 | 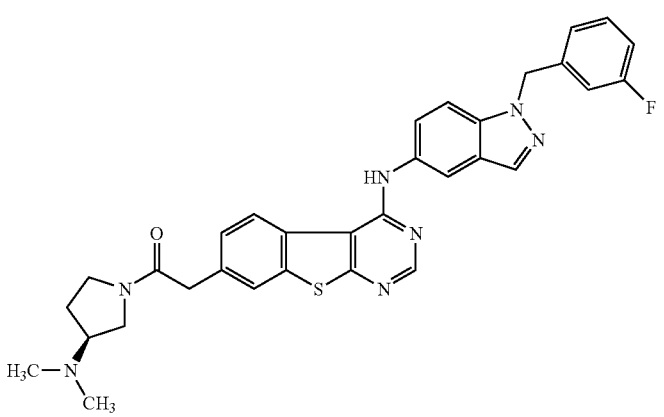 | 2.84 | 580.50 | 7-{2-[3-(dimethylamino)pyrrolidin-1-yl]-2-oxoethyl}-N-[1-(3-fluorobenzyl)-1H-indazol-5-yl][1]benzothieno[2,3-d]pyrimidin-4-amine |
| 126 | 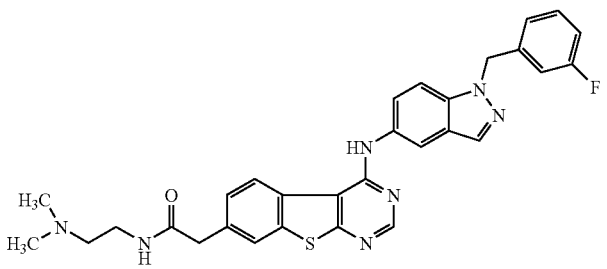 | 2.92 | 554.20 | N-[2-(dimethylamino)ethyl]-2-(4-{[1-(3-fluorobenzyl)-1H-indazol-5-yl]amino}[1]benzothieno[2,3-d]pyrimidin-7-yl)acetamide |

-continued

| Example | Structure | LCMS RT (min) | LCMS Ion [M + H]+ | IUPAC Name |
|---|---|---|---|---|
| 127 | 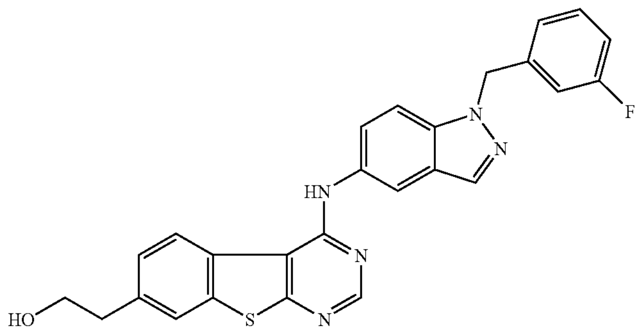 | 3.02 | 470.30 | 2-(4-{[1-(3-fluorobenzyl)-1H-indazol-5-yl]amino}[1]benzothieno[2,3-d]pyrimidin-7-yl)ethanol |
| 128 | 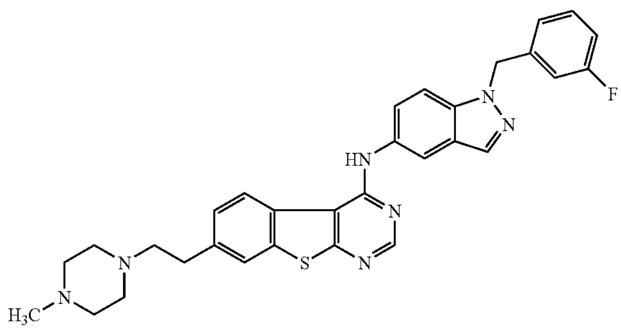 | 2.35 | 552.30 | N-[1-(3-fluorobenzyl)-1H-indazol-5-yl]-7-[2-(4-methylpiperazin-1-yl)ethyl][1]benzothieno[2,3-d]pyrimidin-4-amine |
| 129 | 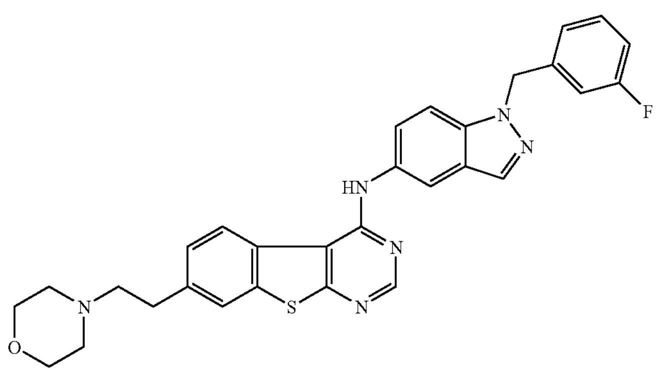 | 2.52 | 539.20 | N-[1-(3-fluorobenzyl)-1H-indazol-5-yl]-7-(2-morpholin-4-ylethyl)[1]benzothieno[2,3-d]pyrimidin-4-amine |
| 130 | 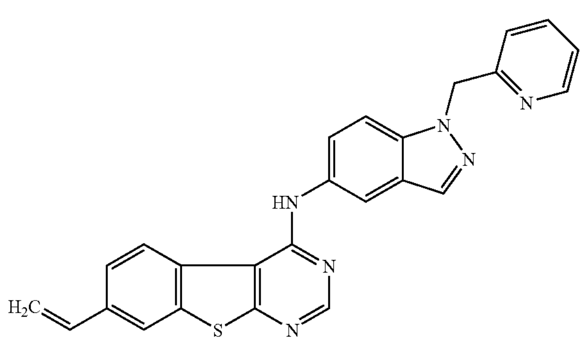 | 2.97 | 435.20 | N-[1-(pyridin-2-ylmethyl)-1H-indazol-5-yl]-7-vinyl[1]benzothieno[2,3-d]pyrimidin-4-amine |

-continued

| Example | Structure | LCMS RT (min) | LCMS Ion [M + H]+ | IUPAC Name |
|---|---|---|---|---|
| 131 | 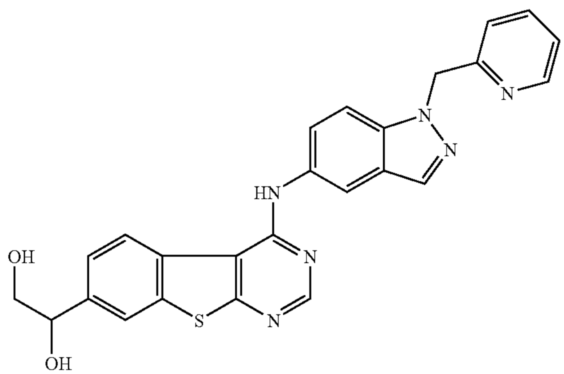 | 1.75 | 469.30 | 1-(4-{[1-(pyridin-2-ylmethyl)-1H-indazol-5-yl]amino}[1]benzothieno[2,3-d]pyrimidin-7-yl)ethane-1,2-diol |
| 132 | 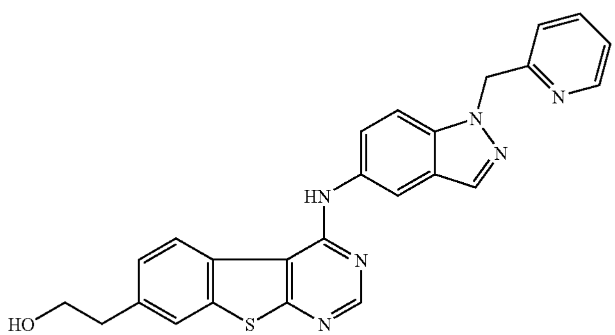 | 2.48 | 452.30 | 2-(4-{[1-(pyridin-2-ylmethyl)-1H-indazol-5-yl]amino}[1]benzothieno[2,3-d]pyrimidin-7-yl)ethanol |
| 133 | 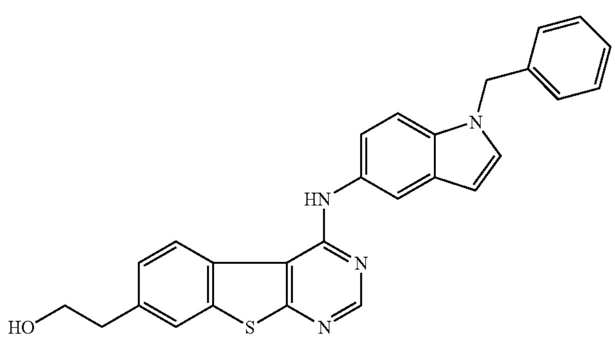 | 3.20 | 451.30 | 2-{4-[(1-benzyl-1H-indol-5-yl)amino][1]benzothieno[2,3-d]pyrimidin-7-yl}ethanol |
| 134 | 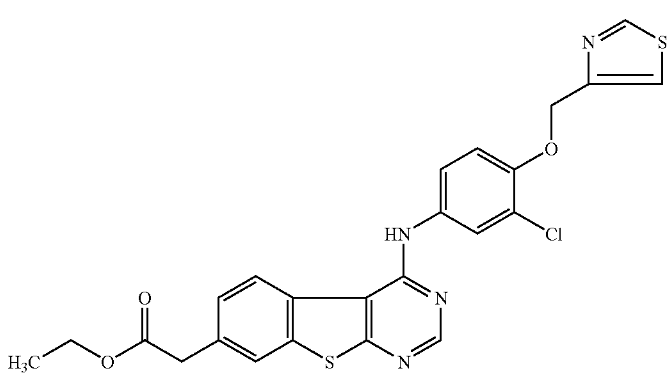 | 3.59 | 511.10 | ethyl (4-{[3-chloro-4-(1,3-thiazol-4-ylmethoxy)phenyl]amino}[1]benzothieno[2,3-d]pyrimidin-7-yl)acetate |

-continued

| Example | Structure | LCMS RT (min) | LCMS Ion [M + H]+ | IUPAC Name |
|---|---|---|---|---|
| 135 | 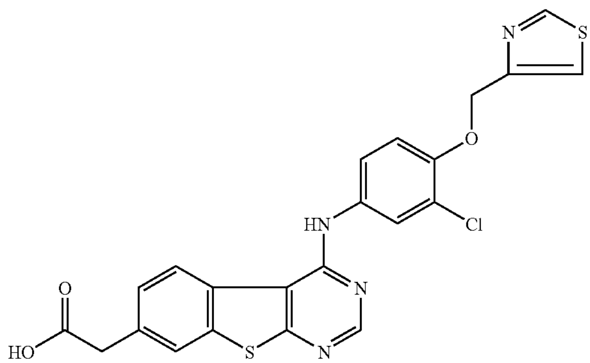 | 3.08 | 483.10 | (4-{[3-chloro-4-(1,3-thiazol-4-ylmethoxy)phenyl]amino}[1]benzothieno[2,3-d]pyrimidin-7-yl)acetic acid |
| 136 | 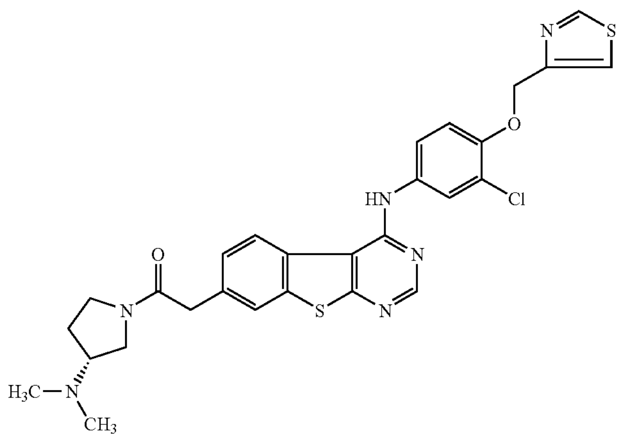 | 2.42 | 579.10 | N-[3-chloro-4-(1,3-thiazol-4-ylmethoxy)phenyl]-7-{2-[(3R)-3-(dimethylamino)pyrrolidin-1-yl]-2-oxoethyl}[1]benzothieno[2,3-d]pyrimidin-4-amine |
| 137 | 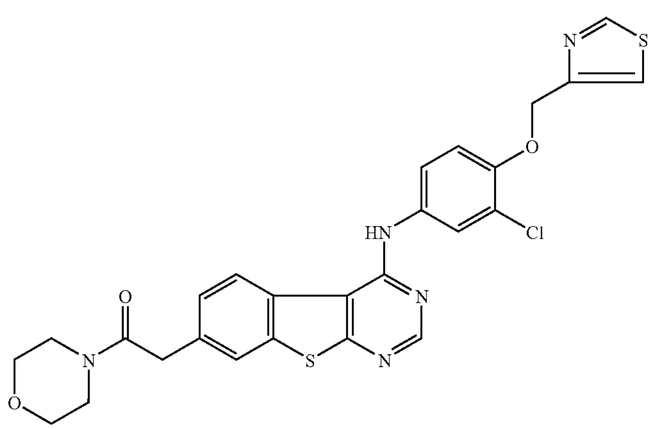 | 2.99 | 552.10 | N-[3-chloro-4-(1,3-thiazol-4-ylmethoxy)phenyl]-7-(2-morpholin-4-yl-2-oxoethyl)[1]benzothieno[2,3-d]pyrimidin-4-amine |

-continued

| Example | Structure | LCMS RT (min) | LCMS Ion [M + H]+ | IUPAC Name |
|---|---|---|---|---|
| 138 | 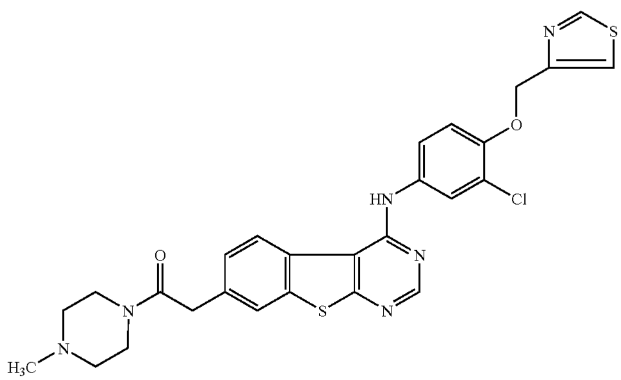 | 2.40 | 565.10 | N-[3-chloro-4-(1,3-thiazol-4-ylmethoxy)phenyl]-7-[2-(4-methylpiperazin-1-yl)-2-oxoethyl][1]benzothieno[2,3-d]pyrimidin-4-amine |
| 139 | 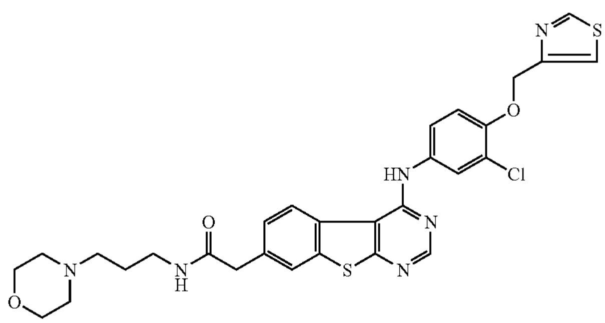 | 2.44 | 609.10 | 2-(4-{[3-chloro-4-(1,3-thiazol-4-ylmethoxy)phenyl]amino}[1]benzothieno[2,3-d]pyrimidin-7-yl)-N-(3-morpholin-4-ylpropyl)acetamide |
| 140 | 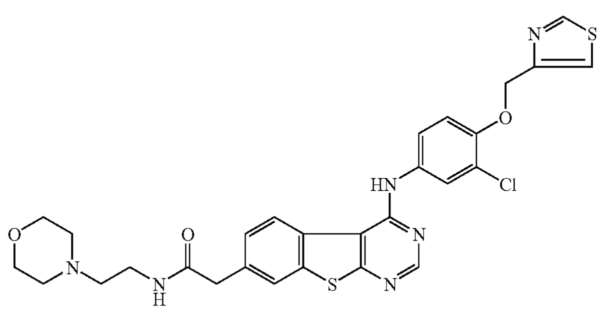 | 2.43 | 595.00 | 2-(4-{[3-chloro-4-(1,3-thiazol-4-ylmethoxy)phenyl]amino}[1]benzothieno[2,3-d]pyrimidin-7-yl)-N-(2-morpholin-4-ylethyl)acetamide |
| 141 | 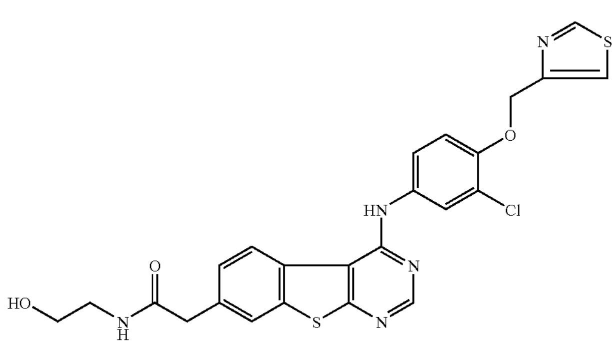 | 2.74 | 526.10 | 2-(4-{[3-chloro-4-(1,3-thiazol-4-ylmethoxy)phenyl]amino}[1]benzothieno[2,3-d]pyrimidin-7-yl)-N-(2-hydroxyethyl)acetamide |

-continued

| Example | Structure | LCMS RT (min) | LCMS Ion [M + H]+ | IUPAC Name |
|---|---|---|---|---|
| 142 | 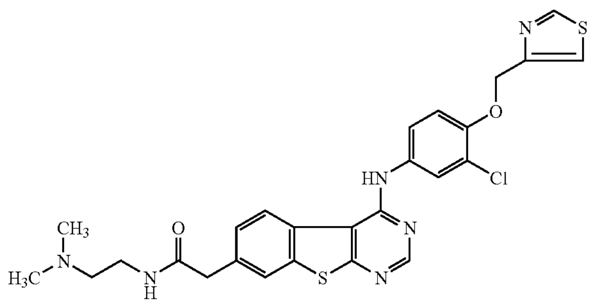 | 2.42 | 553.00 | 2-(4-{[3-chloro-4-(1,3-thiazol-4-ylmethoxy)phenyl]amino}[1]benzothieno[2,3-d]pyrimidin-7-yl)-N-[2-(dimethylamino)ethyl]acetamide |
| 143 | 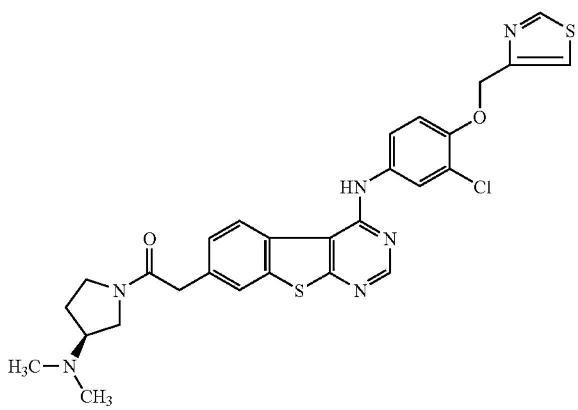 | 2.43 | 579.10 | N-[3-chloro-4-(1,3-thiazol-4-ylmethoxy)phenyl]-7-{2-[(3S)-3-(dimethylamino)pyrrolidin-1-yl]-2-oxoethyl}[1]benzothieno[2,3-d]pyrimidin-4-amine |
| 144 | 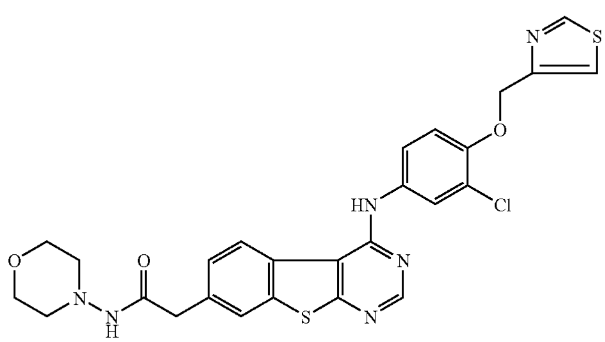 | 2.82 | 567.00 | 2-(4-{[3-chloro-4-(1,3-thiazol-4-ylmethoxy)phenyl]amino}[1]benzothieno[2,3-d]pyrimidin-7-yl)-N-morpholin-4-ylacetamide |
| 145 | 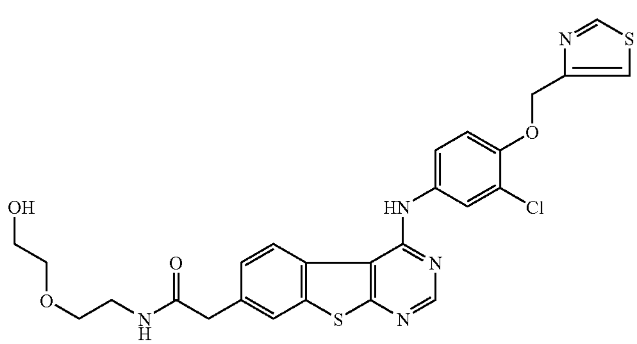 | 2.75 | 570.10 | 2-(4-{[3-chloro-4-(1,3-thiazol-4-ylmethoxy)phenyl]amino}[1]benzothieno[2,3-d]pyrimidin-7-yl)-N-[2-(2-hydroxyethoxy)ethyl]acetamide |

-continued

| Example | Structure | LCMS RT (min) | LCMS Ion [M+H]+ | IUPAC Name |
|---|---|---|---|---|
| 146 | 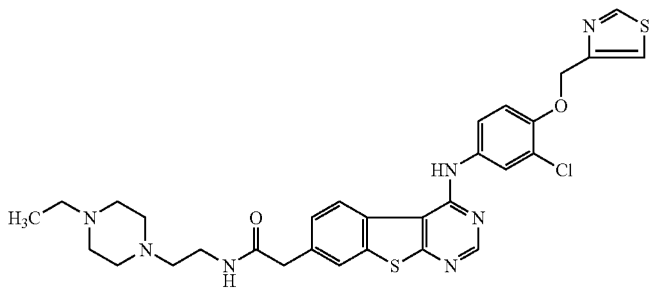 | 2.35 | 622.10 | 2-(4-{[3-chloro-4-(1,3-thiazol-4-ylmethoxy)phenyl]amino}[1]benzothieno[2,3-d]pyrimidin-7-yl)-N-[2-(4-ethylpiperazin-1-yl)ethyl]acetamide |
| 147 | 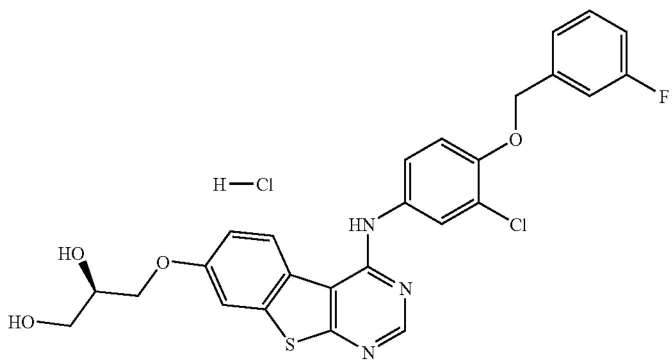 | 3.32 | 526.10 | (2R)-3-{[4-({3-chloro-4-[(3-fluorobenzyl)oxy]phenyl}amino)[1]benzothieno[2,3-d]pyrimidin-7-yl]oxy}propane-1,2-diol hydrochloride |
| 148 | 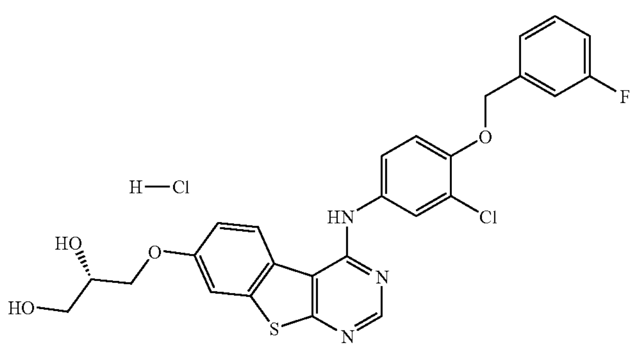 | | | (2S)-3-{[4-({3-chloro-4-[(3-fluorobenzyl)oxy]phenyl}amino)[1]benzothieno[2,3-d]pyrimidin-7-yl]oxy}propane-1,2-diol hydrochloride |
| 149 | 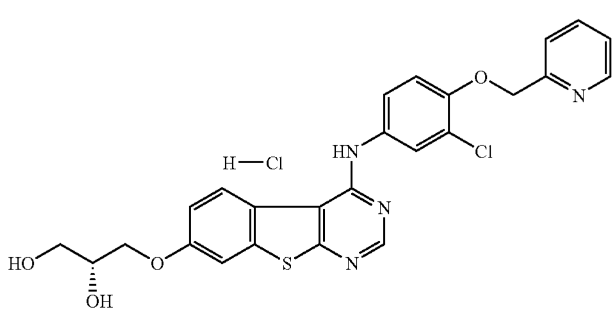 | | | (2R)-3-[(4-{[3-chloro-4-(pyridin-2-ylmethoxy)phenyl]amino}[1]benzothieno[2,3-d]pyrimidin-7-yl)oxy]propane-1,2-diol hydrochloride |

| Example | Structure | LCMS RT (min) | LCMS Ion [M+H]+ | IUPAC Name |
|---------|-----------|---------------|-----------------|------------|
| 150 | 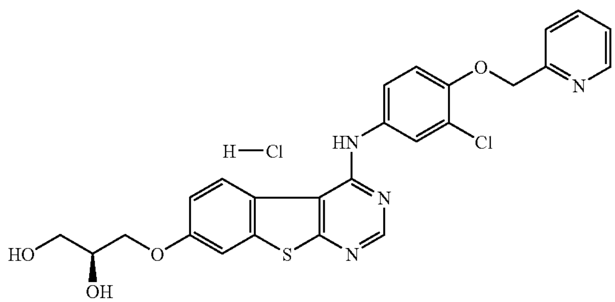 | | | (2S)-3-[(4-{[3-chloro-4-(pyridin-2-ylmethoxy)phenyl]amino}[1]benzothieno[2,3-d]pyrimidin-7-yl)oxy]propane-1,2-diol hydrochloride |

B. PHYSIOLOGICAL ACTIVITY

The utility of the compounds of the present invention can be illustrated, for example, by their activity in vitro in the in vitro tyrosin kinase inhibition assay described below.

In Vitro Tyrosin Kinase Inhibition Assay

The ability of compounds in the present invention to inhibit the tyrosine kinase activities of EGFR (erbB1) and HER2 (erbB2) in cellular systems was measured using ELISA (Enzyme-Linked Immunosorbent Assay) shown below.

Inhibition of Tyrosine Phosphorylation of HER1 in A431 Cells

Materials:

Essentially fatty acid free Bovine Albumin: SIGMA #A9205 30% solution 96-well tissue culture treated plate 96-well EIA/RIA plates: Corning Costar #9018

BSA for blocking Kirkegaard & Perry: #50-61-00

DPBS w/o calcium and magnesium: Gibco/Invitrogen #14190

Wash Buffer: TBS/0.05% Tween

RhEGF: Gibco/Invitrogen 313427-051

Her-1 Ab: Upstate Anti-EGF receptor (neutralizing) mouse monoclonal IgG clone

LA1 #05-101.

Biosource phospho-specific Anti-EFG receptor (pY1068): #44-788G

Amersham Biosciences ECL Anti-rabbit IgG peroxidase-linked antibody: #NA934

TMB Substrate:Sigma #T-8665

Lysis Buffer (Kept on Ice):

TBS

1% Triton X-100

1 mM EDTA 1 mM Sodium orthovanadate 10 mM Beta glycerol phosphate 1 mM Sodium Fluoride 10 μg/ml Aprotinin 1× Roche Complete EDTA-free protease inhibitor cocktail (1 tablet/2 mL $H_2O$=25×)

Method: Note: All antibody plate washes were performed with plate washer. EGF was performed using a Zymark auto liquid handler unit.

Day 1

Plate 30K A431 cells/well in serum-containing media in 96-well plate.

Incubate at 37° C.

Antibody Plates Dilute Her-1 neutralizing antibody in PBS to a final concentration of 1 ug/mL.

Add 100 μL/well to 96-well EIA/RIA plates. Incubate overnight at 4° C. on rotator.

Day 2

BSA block antibody plates: Make stock of TBST containing 3% KPL BSA. Wash plates 3×200 μL/well with TBST. Add 100 μL/well TBST/3% BSA.

Incubate at 37° C. for at least one hour.

Make stock of basal media containing 0.1% BSA and sterile filter.

Wash plates 2×100 μL/well with basal media and add 100 μL/well basal media/0.1% BSA.

Incubate at 37° C. for 2 h.

Create master compound dilution plate at concentrations 3-fold final concentrations. Initial concentration is in 0.1% BSA/Media. Subsequent dilutions performed in 0.1% BSA/Media containing 0.3% DMSO to match that found in the initial drug concentration. Keep two columns without drug for drug free comparison These columns should contain media/0.1% BSA/DMSO only. Transfer 50 μL/well to cell plate containing 0.1% BSA/Media.

Incubate at 37° C. for 2 hrs.

EGF Stimulation: Make 500 ng/ml stock of rhEGF (10×) in 0.1% BSA/Media. Keeping one drug-free column unstimulated, add 15 μL/well to rest of cell plate (50 ng/ml final). For each compound, add to entire series of drug concentration at same time to insure equal stimulation time for all concentrations for that compound. Incubate 5 min at r.t. with periodic swirling. Immediately place on ice 5 min.

Remove media and wash plate 2×150 μL/well with cold DPBS. Add 150 μL/well cold Lysis Buffer containing protease inhibitors. Incubate on ice 30 min rotating.

Antibody coated plates: wash plates 3×200 μL/well with TBST. Transfer 100 μL/well lysate to antibody coated plate. Incubate 4° C. overnight rotating.

Day 3

Wash plate 3×200 μL/well with TBST and add 100 μL/well EGFR phospho specific Ab diluted to Ab100 ng/ml diluted/ml TBS/3% BSA. Incubate on rotator r.t. 1 h.

Wash plate 3×200 μL/well with TBST and add 100 μL/well Anti-rabbit IgG Ab diluted 1:9000

Incubate on rotator at r.t. for 1 h.

Wash plate 3×200 uL/well with TBST and add 50 μL/well TMB substrate. Incubate r.t. till developed (blue, while maintaining dose response). Stop with 100 μL/well 1M HCL and read at 450 nm.

Inhibition of Tyrosine Phosphorylation of HER2 in BT474 Cells

Materials:

BT474 Cells grown in RPMI 1640 Gibco #11875-093, 10% FCS

Essentially fatty acid free Bovine: Albumin SIGMA #A9205 30% solution 96-well tissue culture treated plate EIA/RIA 96-well plates: Corning, Inc #9018

HER2/ab-2: NeoMarkers, Inc. c-erbB-2/HER-2/neu Oncoprotein/Ab-2 (Clone 9G6.10)
    #MS-229-PABX HER2/Ab-18: NeoMarkers, Inc. c-erbB-2/HER-2/neu biotin-tagged (Phospho-specific)
    Ab-18 (Clone PN2A): #MS-1072-BO Amersham Pharmacia Biotech Streptavidin-Horseradish Peroxidase Conjugate:
    #RPN 1231

TMB Substrate: Sigma #T-8665

Wash Buffer: TBS/0.05% Tween

Lysis Buffer:

TBS

1% Triton X-100

1 mM EDTA
    1 mM Sodium orthovanadate
    10 mM Beta glycerol phosphate 1 mM Sodium Fluoride 10 ug/ml Aprotinin 1× Roche Complete EDTA-free protease inhibitor cocktail (1 tablet/2 mls H$_2$O)

Method:

Day 1

Plate 30K BT474 cells/well (RPMI/10% FCS) in tissue culture treated 96-well dish columns 2-12.

Add 100 μL growth media to column one to act as signal to noise factor.

Incubate at 37° C.

Coat Antibody Plates: Dilute Her-2 Ab-2 in PBS to a final concentration of 2 μg/ml.

Add 100 μL/well to 96-well EIA/RIA plates. Incubate o.n. at 4 degrees C. on rotator.

Day 2

Block antibody plates: Wash plates 3×200 μL/well with TBST. Add 100 μL/well TBST/3% BSA.

Incubate 37° C. at least one hour.

Make stock of basal media containing 0.1% BSA and sterile filter.

Wash cell plates 2×100 μL/well with basal media and add 100 μL/well basal media/0.1% BSA.

Incubate 37° C. Incubate at 37° C. for 2 h.

Create master compound dilution plate at concentrations 3-fold desired final concentrations.

Initial concentration is in 0.1% BSA/Media. Subsequent dilutions performed in 0.1% BSA/Media containing 0.3% DMSO to match that found in the initial drug concentration. Keep two columns without drug for drug-free comparison These columns should contain media/0.1% BSA/DMSO only. Transfer 50 μL/well to cell plate containing 0.1% BSA/Media.

Incubate at 37° C. for 2 h.

Remove media and wash plate 2×150 μL/well with cold DPBS. Add 150 uL/well cold Lysis Buffer containing protease inhibitors. Incubate on ice 30 min rotating.

Wash blocked antibody coated plate 3×200 μL/well with TBST. Transfer 100 μL/well lysate to antibody coated plate. Incubate on rotator at 4° C. overnight.

Day 3

Wash plate 3×200 μL/well with TBST and add 100 μL/well Biotin-tagged phospho-Her-2 antibody diluted to 20 ng/mL in TBS/3% BSA. Incubate on rotator at r.t. for 1 h.

Wash plate 3×200 uL/well with TBST and add 100 uL/well Streptavidin-Horseradish Peroxidase Conjugate diluted to 100 ng/mL in TBS/3% BSA. Incubate on rotator at r.t. for 1 h.

Wash plate 3×200 μL/well with TBST and add 50 μL/well TMB substrate. Incubate r.t. till developed (blue, while maintaining dose response). Stop with 100 μL/well 1M HCL and read at 450 nm.

In Vitro Tumor Cell Proliferation Assay

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays.

Many of the compounds and compositions described herein, exhibit anti-proliferative activity with $IC_{50} \leq 50$ μM in either of the following specified cell lines and are thus useful to prevent or treat the disorders associated with hyper-proliferation. The following assay is one of the methods by which compound activity relating to treatment of the disorders identified herein can be determined.

The tumor cell proliferation assay used to test the compounds of the present invention involves a readout called Cell Titer-Glow® Luminescent Cell Viability Assay developed by Promega® (Cunningham, B A "A Growing Issue: Cell Proliferation Assays, Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

A431 cells [human epidermoid carcinoma, ATCC # HTB-20, overexpressing HER1 (EGFR, ErbB1)] and BT474 [human breast carcinoma, ATCC # CRL-1555, overexpressing HER2 (ErbB2)] were plated at a density of $2.5 \times 10^3$ cells/well in 96 well black-clear bottom tissue culture plates in RPMI media with 10% Fetal Bovine Serum and incubated at 37° C. Twenty-four hours later, test compounds are added at a final concentration range from as high 100 μm to as low 64 pM depend on the activities of the tested compounds in serial dilutions at a final DMSO concentration of 0.1%. Cells were incubated for 72 hours at 37° C. in complete growth media after addition of the test compound. After 72 hours of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR 2 using Luminescence protocol, and analyzed with Analyze5 software to generate $IC_{50}$ values. Representative compounds of this invention showed inhibition of tumor cell proliferation in this assay.

For determination of $IC_{50}$'s, a linear regression analysis can be used to determine drug concentration which results in a 50% inhibition of cell proliferation using this assay format. The anti-proliferative activities of selective sets of compounds are listed below. In A431 cells, Examples 2, 3, 5, 6, 8, 9, 11, 12, 15, 17, 20-32, 35, 36, 38, 39, 41, 46, 47, 49, 51, 52, 55, 62-64, 68-70, 73, 77, 82, 83, 85, 86, 90, 91, 101, 107-109, 112, 115-117, 119, 122-129, 132, 136, 138, 143, and 147 have $IC_{50}$'s≦5 μM; whereas examples 1, 4, 7, 10, 13, 14, 16, 18, 19, 33, 34, 37, 40, 42-45, 48, 50, 53, 54, 56-61, 65-67, 71, 72, 74-76, 78-81, 84, 87-89, 92-100, 102-106, 110, 111, 113, 114, 118, 120, 121, 130, 131, 133-135, 137, 139-142, and 144-146 have $IC_{50}$'s≦50 μM. In BT474 cells, examples 3-6, 8-12, 14-18, 20-23, 25-39, 41, 43, 44, 46, 50, 53, 55, 60-64, 69, 73-77, 80, 82-86, 88-93, 96, 97, 100, 102, 104, 109, 111, 112, 114, 115-117, 119, 120, 122-133, 136, 142, 143, 146, and 147 have $IC_{50}$'s≦500 nM; whereas examples 1, 2, 7, 13, 19, 24, 40, 42, 45, 47, 48, 49, 51, 52, 54, 52-59, 65-68, 70-72, 78-81, 87, 94, 95, 98, 99, 101, 103, 105-108, 110, 113, 118, 121, 134, 135, 137-141, 144, and 145 have $IC_{50}$'s≦5 μM.

C. OPERATIVE EXAMPLES RELATING TO PHARMACEUTICAL COMPOSITIONS

The compounds according to the invention can be converted into pharmaceutical preparations as follows:

Tablet:

Composition:
100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:
The mixture of active component, lactose and starch is granulated with a 5% solution (m/m) of the PVP in water. After drying, the granules are mixed with magnesium stearate for 5 min. This mixture is molded using a customary tablet press (tablet format, see above). The molding force applied is typically 15 kN.

Suspension for Oral Administration:

Composition:
1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:
The Rhodigel is suspended in ethanol and the active component is added to the suspension. The water is added with stirring. Stirring is continued for about 6 h until the swelling of the Rhodigel is complete.

Solution for Intravenous Administration 1:

Composition: 100-200 mg of the compound of Example 1, 15 g polyethylenglykol 400 and 250 g water optionally with up to 15% Cremophor EL (BASF, Germany), and optionally up to 15% ethyl alcohol, and optionally up to 2 equivalents of a pharmaceutically suitable acid such as citric acid or hydrochloric acid.

Preparation:
The compound of Example 1 and the polyethylenglykol 400 are dissolved in the water with stirring. The solution is sterile filtered (pore size 0.22 μm) and filled into heat sterilized infusion bottles under aseptical conditions. The infusion bottles are being sealed with rubber seals.

Solution for Intravenous Administration 2:

Composition: 100-200 mg of the compound of Example 1, saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid.

Preparation:
The compound of Example 1 is dissolved in the saline solution with stirring. Optionally Cremophor EL, ethyl alcohol or acid are added. The solution is sterile filtered (pore size 0.22 μm) and filled into heat sterilized infusion bottles under aseptical conditions. The infusion bottles are being sealed with rubber seals.

The invention claimed is:
1. A compound of formula (I)

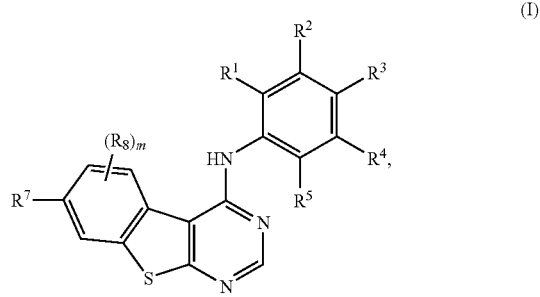

wherein
- m is 0, 1 or 2;
- $R^1$ is selected from the group consisting of hydrogen, alkyl, and halo;
- $R^2$ is selected from the group consisting of hydrogen, alkyl, and halo; and
- $R^3$ is *—O(CH$_2$)$_n$Ar, wherein Ar is phenyl, thienyl, furyl, pyrrolyl, thiazolyl, oxazolyl, imidazolyl, pyridyl, pyrimidyl or pyridazinyl, wherein Ar can optionally be substituted with 0, 1 or 2 substituents independently selected from the group consisting of halo, cyano, amino, methyl, ethyl, propyl, hydroxy, methoxy, ethoxy, propoxy, trifluoromethyl and trifluoromethoxy, and wherein n is 0 or 1, or
- $R^2$ and $R^3$, together with the carbon atoms to which they are attached, form a pyrrole or pyrazole ring, wherein said pyrrole or pyrazole ring can optionally be substituted with 0, 1 or 2 substituents independently selected from the group consisting of alkyl, benzyl, halogenated benzyl, pyridylmethyl, pyridylmethoxy, and halogenated pyridylmethoxy;
- $R^4$ is selected from the group consisting of hydrogen, methyl, ethyl, and halo;
- $R^5$ is selected from the group consisting of hydrogen, methyl, and halo;
- $R^7$ is selected from the group consisting of halo, hydroxy, alkyl, and alkenyl; or
- $R^7$ is alkoxy, wherein said alkoxy can optionally be substituted with 0, 1 or 2 substituents independently selected from the group consisting of hydroxy, alkoxy, alkoxycarbonyl, amino, alkylamino, morpholinyl, piperidinyl, pyrrolidinyl, piperazinyl, and alkylpiperazinyl, or
- $R^7$ is alkylamino, wherein said alkylamino can optionally be substituted with 0, 1 or 2 substituents independently selected from the group consisting of hydroxy, alkoxy, hydroxyalkylamino, alkoxyalkylamino, and morpholinyl, piperidinyl, pyrrolidinyl, piperazinyl, and alkylpiperazinyl, or
- $R^7$ is alkyl selected from the group consisting of methyl, ethyl, n-propyl, i-propyl, n-butyl, i-butyl and t-butyl, wherein said alkyl is substituted with 1, 2, 3 or 4 independently selected substituents $R^{7-1}$,
- wherein $R^{7-1}$ is selected from the group consisting of halo, oxo, hydroxy, alkoxy, amino, hydroxycarbonyl, and alkoxycarbonyl, or
- $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
- $R^{7-1}$ is alkoxy, wherein said alkoxy can optionally be substituted with 0, 1 or 2 substituents independently selected from the group consisting of hydroxy, alkoxy, amino, alkoxycarbonyl, morpholinyl, pyrrolyl, and pyrrolidinyl, or
- $R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, oxo, hydroxy, alkoxy, amino, alkylamino, hydroxyalkyl, alkoxyalkyl, carboxyl, and alkoxycarbonyl, or
- $R^{7-1}$ is a group *—C(O)NR$^{7-2}$R$^{7-3}$, wherein R$^{7-2}$ is morpholinyl azabicyclo[2.2.2]oct-3-yl or alkyl, wherein alkyl can optionally be substituted with 0, 1 or 2 substituents selected from the group consisting of hydroxy, alkoxy, hydroxyalkyloxy, alkylamino, methylsulfonyl, piperidinyl and morpholinyl, and wherein R$^{7-3}$ is hydrogen or alkyl, or
- $R^{7-1}$ is a group *—C(O)NR$^{7-2}$R$^{7-3}$, wherein R$^{7-2}$ and R$^{7-3}$, together with the nitrogen atom to which they are attached, form a heterocycle selected from the group consisting of pyrrolidinyl, piperazinyl, and morpholinyl, wherein said heterocycle can optionally be substituted with 0, 1 or 2 substituents independently selected from the group consisting of alkyl, hydroxyalkyl, alkoxyalkyl, and alkylamino, or
- $R^7$ is alkenyl selected from the group consisting of ethenyl, propenyl, or n-butenyl, wherein said alkenyl is substituted with 1, 2 or 3 independently selected substituents $R^{7-4}$,
- wherein $R^{7-4}$ is selected from the group consisting of halo, hydroxy, oxo, hydroxycarbonyl, alkoxycarbonyl, and alkylamino, wherein alkylamino can be substituted with alkoxy, methylsulfonyl, or alkylamino, or
- $R^{7-4}$ is a heterocycle selected from the group consisting of pyrrolidinyl, piperazinyl, and morpholinyl, wherein said heterocycle can optionally be substituted with 0, 1 or 2 substituents independently selected from the group consisting of hydroxy, alkoxy, alkyl and alkylamino, or
- $R^7$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of methyl, ethyl, propyl, halo, oxo, hydroxy, methoxy, ethoxy, propoxy, hydroxyalkyl, alkoxyalkyl, amino and alkylamino;
- $R^8$ is selected from the group consisting of halo, cyano, amino, methyl, ethyl, propyl, hydroxy, methoxy, ethoxy, propoxy, trifluoromethyl and trifluoromethoxy;
- with the proviso that at least one of $R^1$, $R^2$, $R^4$, and $R^5$ must be other than hydrogen;

or a pharmaceutically acceptable salt thereof.

2. The compound of claim 1, wherein
- m is 0;
- $R^1$ hydrogen;
- $R^2$ is hydrogen;
- $R^3$ is selected from the group consisting of benzyloxy, halogenated benzyloxy, methylated benzyloxy, pyridylmethoxy and thiazolylmethoxy; or
- $R^2$ and $R^3$, together with the carbon atoms to which they are attached, form a pyrazole ring, wherein said pyrazole ring can optionally be substituted with 0 or 1 substituents independently selected from the group consisting of benzyl and halogenated benzyl;
- $R^4$ is fluoro, chloro or bromo;
- $R^5$ hydrogen;
- $R^7$ is methoxy, ethoxy or propoxy, wherein said methoxy, ethoxy or propoxy can optionally be substituted with 0, 1 or 2 substituents independently selected from the group consisting of hydroxy, methoxy, ethoxy, propoxy, methoxycarbonyl, ethoxycarbonyl, amino, methylamino, dimethylamino ethylamino, methylethylamino, diethylamino, morpholinyl, piperidinyl, pyrrolidinyl, piperazinyl, and methylpiperazinyl, or
- $R^7$ is alkyl selected from the group consisting of methyl, ethyl, n-propyl, and n-butyl, wherein said alkyl is substituted with 1 or 2 substituents $R^{7-1}$,
- wherein $R^{7-1}$ is selected from the group consisting of fluoro, chloro, bromo, hydroxy, methoxy, methoxycarbonyl, and ethoxycarbonyl, or $R^{7-1}$ is ethylamino, methylethylamino, dimethylamino or diethylamino, wherein said ethylamino, methylethylamino, dimethylamino or diethylamino can optionally be substituted with 0, 1 or 2 substituents independently selected from the group consisting of hydroxy, methoxy, ethoxy, methylsulfonyl, and morpholinyl, or $R^{7-1}$ is a heterocycle selected from the group consisting of pyrrolidinyl, imidazolyl, morpholinyl, piperidinyl, piperazinyl, and thiomorpholinyl, wherein said heterocycle can optionally be substituted with 0, 1 or 2 substituents independently selected from the group consisting of methyl, oxo, hydroxy, amino, methylamino, ethylamino, methylethylamino, dimethylamino, diethylamino, hydroxymethyl, hydroxyethyl, methoxymethyl, methoxyethyl, and ethoxyethyl, or $R^{7-1}$ is a group *—$C(O)NR^{7-2}R^{7-3}$, wherein $R^{7-2}$ is morpholinyl, methyl, ethyl or propyl, wherein methyl, ethyl or propyl can optionally be substituted with 0, 1 or 2 substituents selected from the group consisting of hydroxy, alkoxy, hydroxyalkyloxy, alkylamino, methylsulfonyl, piperidinyl and morpholinyl, and wherein $R^{7-3}$ is hydrogen, methyl, ethyl or propyl, or $R^{7-1}$ is a group *—$C(O)NR^{7-2}R^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0, 1 or 2 substituents independently selected from the group consisting of methyl, ethyl, propyl, methoxymethyl, methoxyethyl, ethoxyethyl, methylamino, methylethylamino, dimethylamino, and diethylamino, or $R^7$ is alkenyl selected from the group consisting of ethenyl, propenyl, or n-butenyl, wherein said alkenyl is substituted with 1, 2 or 3 independently selected substituents $R^{7-4}$, wherein $R^{7-4}$ is selected from the group consisting of halo, hydroxy, oxo, hydroxycarbonyl, methoxycarbonyl, ethoxycarbonyl, methylamino, ethylamino, methylethylamino, dimethylamino, and diethylamino, wherein ethylamino, methylethylamino, and diethylamino can be substituted with methoxy, ethoxy, methylsulfonyl, methylamino, ethylamino, methylethylamino, dimethylamino, or diethylamino, or $R^{7-4}$ is a heterocycle selected from the group consisting of pyrrolidinyl, piperazinyl, and morpholinyl, wherein said heterocycle can optionally be substituted with 0, 1 or 2 substituents independently selected from the group consisting of hydroxy, alkoxy, alkyl and alkylamino;

or a pharmaceutically acceptable salt thereof.

3. The compound of claim 1, wherein m is 0;

$R^1$ is hydrogen;

$R^2$ is hydrogen;

$R^3$ is selected from the group consisting of benzyloxy, 3-fluorobenzyloxy, 3-chlorobenzyloxy, 3-bromobenzyloxy, and 3-methylbenzyloxy;

$R^4$ is chloro;

$R^5$ hydrogen;

$R^7$ is propoxy, wherein said propoxy can optionally be substituted with 0, 1 or 2 substituents independently selected from the group consisting of hydroxy, methoxy, ethoxy, amino, dimethylamino, or diethylamino or $R^7$ is alkyl selected from the group consisting of methyl and ethyl, wherein said alkyl is substituted with 1 or 2 substituents $R^{7-1}$, wherein $R^{7-1}$ is selected from the group consisting of hydroxy, and methoxycarbonyl, or $R^{7-1}$ is ethylamino, methylethylamino, dimethylamino or diethylamino, wherein said ethylamino, methylethylamino, dimethylamino or diethylamino can optionally be substituted with 1 or 2 substituents independently selected from the group consisting of hydroxy, methoxy, ethoxy, methylsulfonyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0, 1 or 2 substituents independently selected from the group consisting of methyl, oxo, hydroxy, amino, dimethylamino, hydroxymethyl, methoxymethyl, and methoxyethyl, or $R^{7-1}$ is a group *—$C(O)NR^{7-2}R^{7-3}$, wherein $R^{7-2}$ is morpholinyl or ethyl, wherein ethyl can optionally be substituted with 0 or 1 substituents selected from the group consisting of hydroxy, methoxy, ethoxy, hydroxymethyloxy, hydroxyethyloxy, dimethylamino, methylsulfonyl, piperidinyl and morpholinyl, and wherein $R^{7-3}$ is hydrogen or methyl, or $R^{7-1}$ is a group *—$C(O)NR^{7-2}R^{7-3}$, wherein $R^{7-2}$ and $R^{7-3}$, together with the nitrogen atom to which they are attached, form a heterocycle selected from the group consisting of pyrrolidinyl, piperazinyl, and morpholinyl, wherein said heterocycle can optionally be substituted with 0 or 1 substituents independently selected from the group consisting of methyl, ethyl, propyl, methoxymethyl, methoxyethyl, ethoxyethyl, methylamino, and dimethylamino, or $R^7$ is propenyl, wherein said propenyl is substituted with 1 or 2 independently selected substituents $R^{7-4}$, wherein $R^{7-4}$ is selected from the group consisting of fluoro, chloro, oxo, hydroxycarbonyl, methoxycarbonyl, methylamino, and ethylamino, wherein ethylamino can be substituted with methylsulfonyl, dimethylamino, or diethylamino;

or a pharmaceutically acceptable salt thereof.

4. A process for preparing a compound of claim 1, wherein a compound of formula (III)

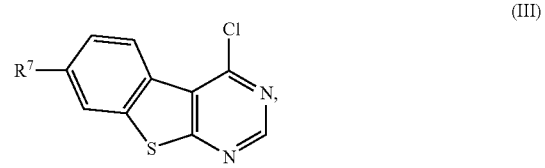

(III)

wherein $R^7$ has the meaning indicated in claim 1, is reacted with a compound of formula (7)

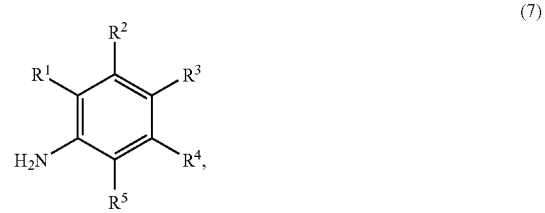

(7)

wherein $R^1$ to $R^5$ the meaning indicated in claim 1.

5. A process for preparing a compound of formula (I) according to claim 1, wherein $R^7$ is alkoxy, comprising reacting a compound of formula (40)

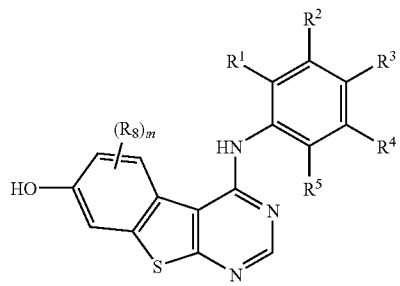

(40)

wherein m and $R^1$ to $R^8$ have the meaning indicated in claim 1,
with an electrophile.

6. A pharmaceutical composition comprising a compound of claim 1 in combination with at least one pharmaceutically acceptable, pharmaceutically safe carrier or excipient.

7. A process for preparing a pharmaceutical composition according to claim 6, comprising combining the compound with at least one pharmaceutically acceptable, pharmaceutically safe carrier or excipient, mixing the combination and bringing the combination into a suitable administration form.

8. The compound of claim 1, wherein $R^7$ is hydroxy.

9. A method of treating epidermoid cancer or breast cancer in a mammal, comprising administering to a mammal in need thereof an effective amount of a compound of claim 1.

10. A packaged pharmaceutical composition comprising a container comprising the pharmaceutical composition of claim 6 and instructions for using the pharmaceutical composition to treat epidermoid cancer or breast cancer in a mammal.

* * * * *